(12) United States Patent
Kanamori

(10) Patent No.: US 9,307,159 B2
(45) Date of Patent: Apr. 5, 2016

(54) POLARIZATION IMAGE PROCESSING APPARATUS

(71) Applicant: Panasonic Intellectual Property Management Co., Ltd., Osaka (JP)

(72) Inventor: Katsuhiro Kanamori, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/616,998

(22) Filed: Feb. 9, 2015

(65) Prior Publication Data

US 2015/0256733 A1 Sep. 10, 2015

(30) Foreign Application Priority Data

Mar. 4, 2014 (JP) .................................. 2014-041456

(51) Int. Cl.

| | |
|---|---|
| H04N 5/225 | (2006.01) |
| H04N 5/235 | (2006.01) |
| G02F 1/01 | (2006.01) |
| G01N 21/21 | (2006.01) |
| G02B 27/28 | (2006.01) |
| G01N 21/17 | (2006.01) |
| B60S 1/08 | (2006.01) |

(52) U.S. Cl.
CPC ............. *H04N 5/2354* (2013.01); *G01N 21/21* (2013.01); *G02F 1/0136* (2013.01); *B60S 1/0844* (2013.01); *G01N 2021/177* (2013.01); *G02B 27/286* (2013.01)

(58) Field of Classification Search
USPC .................................................. 348/370, 371
See application file for complete search history.

(56) References Cited

U.S. PATENT DOCUMENTS

| | | | | |
|---|---|---|---|---|
| 2007/0280669 | A1* | 12/2007 | Karim .................... | G03B 11/00 396/155 |
| 2009/0141027 | A1* | 6/2009 | Sato ...................... | G01B 11/002 345/426 |
| 2010/0157082 | A1* | 6/2010 | Katerberg ............. | G02B 27/281 348/222.1 |
| 2010/0245823 | A1* | 9/2010 | Chhibber .............. | A61B 5/0059 356/366 |
| 2010/0253820 | A1 | 10/2010 | Kanamori et al. | |
| 2010/0283883 | A1* | 11/2010 | Sato ...................... | G02B 27/283 348/335 |

(Continued)

FOREIGN PATENT DOCUMENTS

| | | |
|---|---|---|
| JP | 2013-117519 | 6/2013 |
| WO | 2009/072260 | 6/2009 |

*Primary Examiner* — Jason Flohre
*Assistant Examiner* — Dwight C Tejano
(74) *Attorney, Agent, or Firm* — Wenderoth, Lind & Ponack, L.L.P.

(57) ABSTRACT

A polarization image processing apparatus includes an illumination unit, a splitter, first and second polarization imaging devices, and a processing unit. The illumination unit illuminates a first surface of a transparent or translucent object with first illumination light polarized in a first direction and second illumination light polarized in a second direction, which crosses the first direction, alternately. Illumination axes of the first illumination light and second illumination light substantially coincide with an imaging axis of the polarization image processing apparatus. The splitter divides returning light into at least two light components. The first and second polarization imaging devices receive the light components. The processing unit detects a condition of a second surface of the object on the basis of first and second polarization images obtained by the first polarization imaging device and third and fourth polarization images obtained by the second polarization imaging device.

21 Claims, 46 Drawing Sheets

(56) References Cited

U.S. PATENT DOCUMENTS

2011/0267483 A1* 11/2011 Kanamori ............... G06T 1/00
348/220.1

2012/0206581 A1* 8/2012 Kanamori ............ H04N 5/2354
348/68

2014/0303853 A1 10/2014 Itoh et al.

* cited by examiner

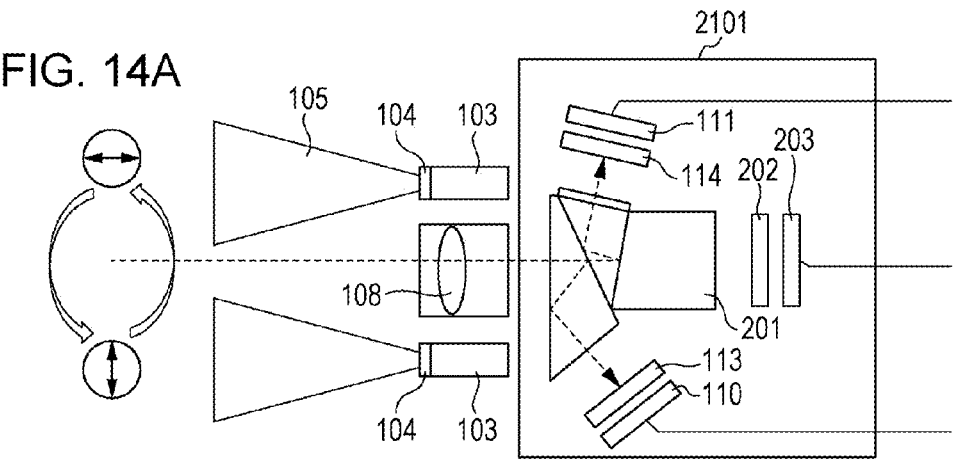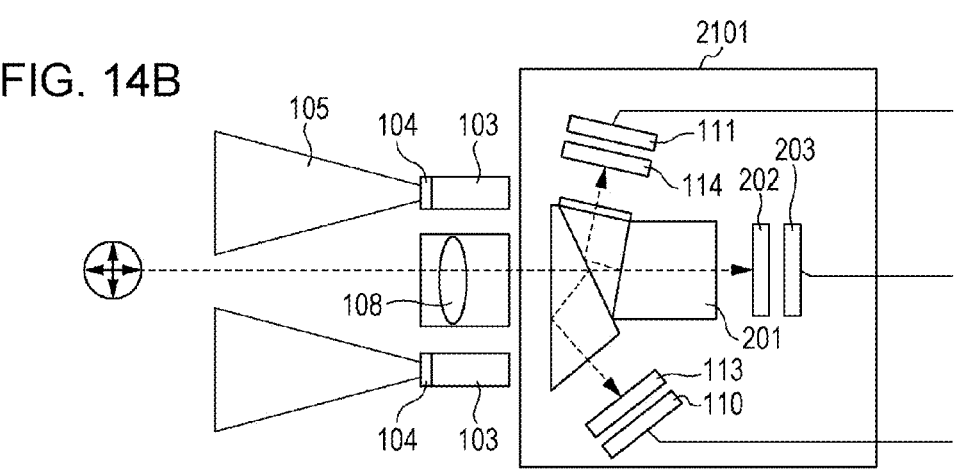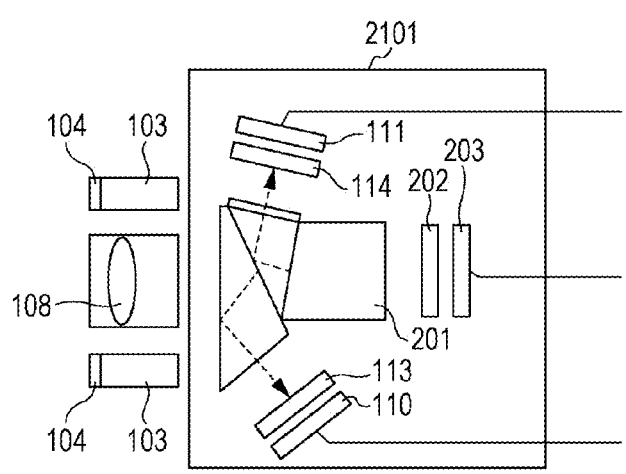

FIG. 16
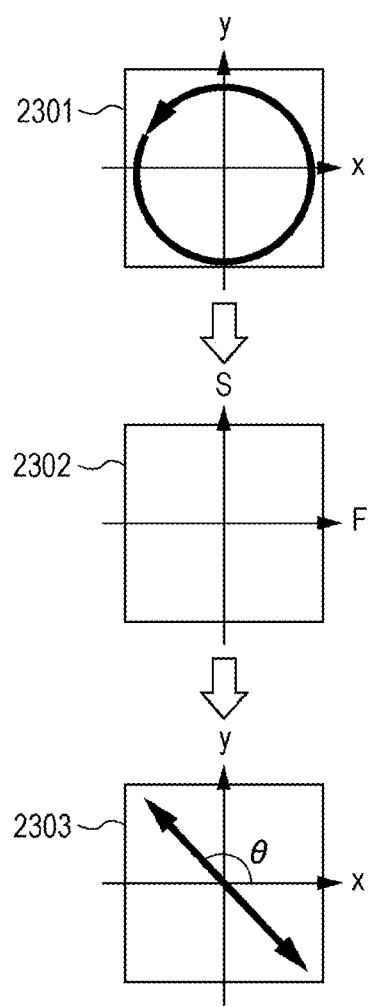
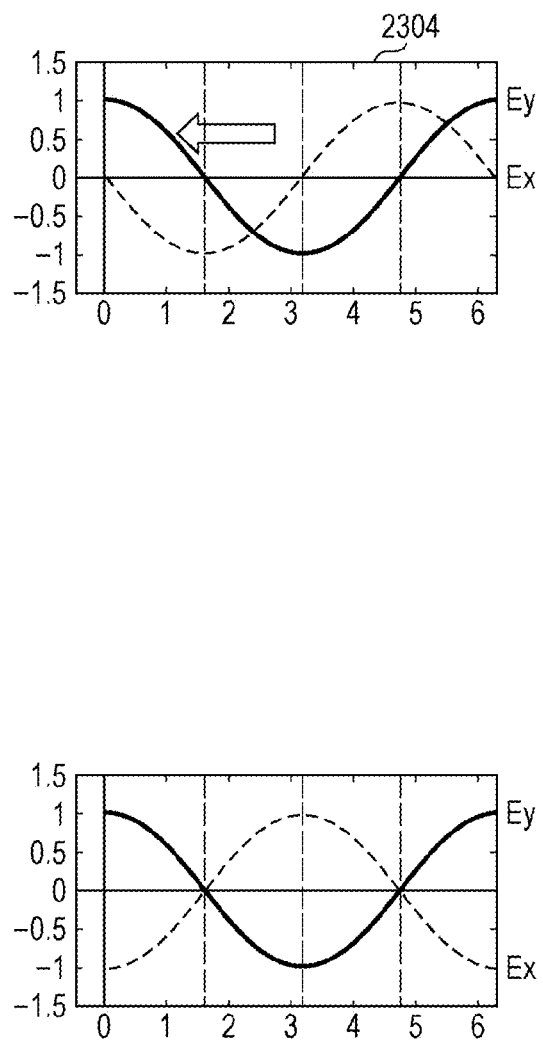

POLARIZATION IMAGE PROCESSING APPARATUS

BACKGROUND

1. Technical Field

The present disclosure relates to a polarization image processing apparatus that performs a polarization illumination process and a polarization imaging process on a transparent or translucent object.

2. Description of the Related Art

Technologies for detecting raindrops on a windshield of a vehicle with an image sensor have been proposed. If the raindrops on the windshield can be optically detected, the operation of wipers can be automatically controlled. However, since glass and raindrops are both transparent, it is difficult to detect the raindrops on the basis of color and brightness of objects.

Japanese Unexamined Patent Application Publication No. 2013-117519 discloses a technology for detecting the raindrops on the windshield by polarization imaging. With this technology, the windshield is irradiated with non-polarized infrared light emitted from the inside of the vehicle, and an image of the raindrops on the outer surface of the windshield is captured by an on-board camera. The camera includes an image sensor including an infrared narrow band filter made of a photonic crystal and a polarizing filter made of a metal wire grid. Image processing is performed to separate the image of the raindrops on the windshield from an image of the scene outside the vehicle by polarization imaging.

With the technology described in Japanese Unexamined Patent Application Publication No. 2013-117519, the windshield is irradiated with non-polarized illumination light. Therefore, it is necessary that an optical axis of the illumination light and an optical axis of the imaging system form the Brewster's angle. The inclination and curvature of the windshield vary depending on the type of the vehicle. Therefore, the angle of the transmission axis of the polarizing filter included in the image sensor and the installation position of the camera need to be adjusted in accordance with the type of the vehicle.

SUMMARY

One non-limiting and exemplary embodiment provides a polarization image processing apparatus capable of detecting the state of a transparent or translucent surface.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature a polarization image processing apparatus including an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus; a splitter that splits returning light that returns from the object into at least two returning light components; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of a second surface of the object on the basis of a difference between a sum of the first polarization image and the fourth polarization image and a sum of the second polarization image and the third polarization image, the second surface being at a side opposite to a side of the first surface.

The image processing apparatus according to the present disclosure performs polarization imaging with one or more polarization imaging devices by performing switching of illumination light or temporal switching of polarization characteristics of the returning light. The image processing apparatus according to the present disclosure is capable of simultaneously capturing an image of a windshield and an image of an external scene and removing the image of the external scene by a polarization difference process. Thus, the condition of the windshield (for example, the presence of raindrops) can be detected.

BRIEF DESCRIPTION OF THE DRAWINGS

FIGS. 14A to 14C illustrate another structure according to the modification of the first embodiment of the present disclosure;

FIG. 16 illustrates the manner in which counterclockwise circularly polarized returning light is converted into linearly polarized light;

DETAILED DESCRIPTION

Figure 1:
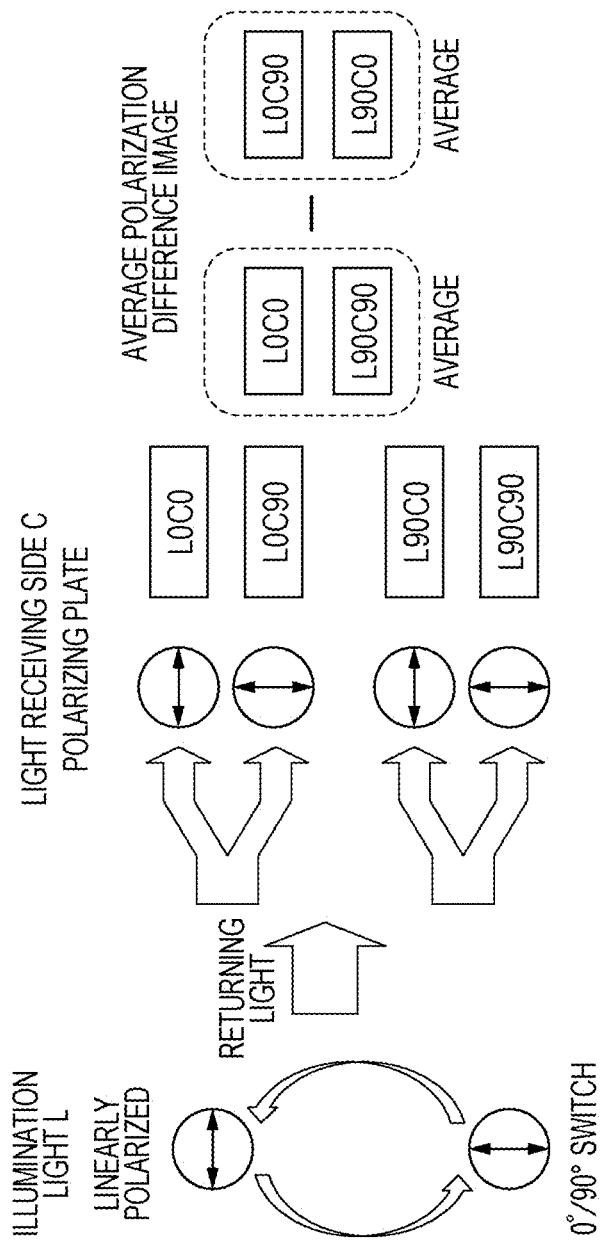
FIG. 1 illustrates a polarization imaging method according to a first embodiment of the present disclosure.

First, various aspects of the present disclosure will be described.

A polarization image processing apparatus according to an aspect of the present disclosure includes an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus; a splitter that splits returning light that returns from the object into at least two returning light components; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of a second surface of the object on the basis of a difference between a sum of the first polarization image and the fourth polarization image and a sum of the second polarization image and the third polarization image, the second surface being at a side opposite to a side of the first surface.

In one embodiment, the processing unit performs a first process of taking an average of the first polarization image and the fourth polarization image to generate an average parallel-Nicols image, a second process of taking an average of the second polarization image and the third polarization image to generate an average crossed-Nicols image, and a third process of determining the difference by performing a subtraction between the average parallel-Nicols image and the average crossed-Nicols image.

In one embodiment, the processing unit generates a brightness image by adding the first, second, third, and fourth polarization images.

In one embodiment, the illumination unit includes a plurality of the first light sources that emit the first illumination light and a plurality of the second light sources that emit the second illumination light.

In one embodiment, an imaging unit including the illumination unit, the splitter, and the first and second polarization imaging devices is provided, and the processing unit is connected to the imaging unit.

In one embodiment, the processing unit includes a droplet detecting unit that detects a droplet on the second surface of the object.

A polarization image processing apparatus according to another aspect of the present disclosure includes an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus; a splitter that splits returning light that returns from the object into first, second, and third light components; a first polarization imaging device that receives the first light component, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives the second light component, the second polarization imaging device obtaining a third polarization image polarized in the second direction while the object is being illuminated with the first illumination light and obtaining a fourth polarization image polarized in the second direction while the object is being illuminated with the second illumination light; a third polarization imaging device that receives the third light component, the third polarization imaging device obtaining a fifth polarization image polarized in a third direction, which differs from the first and second directions, while the object is being illuminated with the first illumination light and obtaining a sixth polarization image polarized in the third direction while the object is being illuminated with the second illumination light; and a processing unit that receives the second, third, fifth, and sixth polarization images from the first, second, and third polarization imaging devices and detects a condition of a second surface the object on the basis of a difference between a sum of the fifth polarization image and the sixth polarization image and a sum of the second polarization image and the third polarization image, the second surface being at a side opposite to a side of the first surface.

In one embodiment, the first direction and the second direction are orthogonal to each other, and the third direction is at an angle in the range of 10 degrees or more and 60 degrees or less with respect to the first direction.

In one embodiment, the processing unit performs a first process of taking an average of the fifth polarization image and the sixth polarization image to generate an average oblique-Nicols image, a second process of taking an average of the second polarization image and the third polarization image to generate an average crossed-Nicols image, and a third process of determining the difference by performing a subtraction between the average oblique-Nicols image and the average crossed-Nicols image.

In one embodiment, the processing unit generates a brightness image by adding the first, second, third, and fourth polarization images.

In one embodiment, the illumination unit includes a plurality of the first light sources that emit the first illumination light and a plurality of the second light sources that emit the second illumination light.

In one embodiment, an imaging unit including the illumination unit, the splitter, and the first and second polarization imaging devices is provided, and the processing unit is connected to the imaging unit.

In one embodiment, the processing unit includes a droplet detecting unit that detects a droplet on the second surface of the object.

A polarization image processing apparatus according to another aspect of the present disclosure includes an illumination unit that illuminates a first surface of a transparent or translucent object with first illumination light and second illumination light alternately, the first illumination light being in a first state of polarization and the second illumination light being in a second state of polarization that differs from the first state of polarization, an illumination axis of the first illumination light and an illumination axis of the second illumination light substantially coinciding with an imaging axis of the polarization image processing apparatus; a splitter that splits returning light that returns from the object into at least two returning light components; a phase shift element arranged so as to allow the returning light that returns from the object to pass therethrough, the phase shift element converting clockwise polarized light into light polarized in a first direction and counterclockwise polarized light into light polarized in a second direction that is orthogonal to the first direction; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of a second surface of the object on the basis of a difference between a sum of the first polarization image and the fourth polarization image and a sum of the second polarization image and the third polarization image, the second surface being at a side opposite to a side of the first surface.

In one embodiment, one of the first state of polarization and the second state of polarization is clockwise circular or elliptical polarization, and the other one of the first state of polarization and the second state of polarization is counterclockwise circular or elliptical polarization.

In one embodiment, the phase shift element is a quarter wave plate.

A polarization image processing apparatus according to another aspect of the present disclosure includes an illumination unit that illuminates a first surface of a transparent or translucent object with circularly polarized light or elliptically polarized light, an illumination axis of the circularly polarized light or elliptically polarized light substantially coinciding with an imaging axis of the polarization image processing apparatus; a splitter that splits returning light that returns from the object into at least two returning light components; a variable phase shift element arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction; a first polarization imaging device that receives one of the at least two returning light components, the first polarization imaging device obtaining a first polarization image polarized in the first direction while the variable phase shift element is operating in the first mode and obtaining a second polarization image polarized in the first direction while the variable phase shift element is operating in the second mode; a second polarization imaging device that receives another one of the at least two returning light components, the second polarization imaging device obtaining a third polarization image polarized in the second direction while the variable phase shift element is operating in the first mode and obtaining a fourth polarization image polarized in the second direction while the variable phase shift element is operating in the second mode; and a processing unit that receives the first, second, third, and fourth polarization images from the first and second polarization imaging devices and detects a condition a second surface of the object on the basis of a difference between a sum of the first polarization image and the fourth polarization image and a sum of the second polarization image and the third polarization image, the second surface being at a side opposite to a side of the first surface.

A polarization image processing apparatus according to another aspect of the present disclosure includes an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus; a polarization imaging device that receives returning light that returns from the object, the polarization imaging device obtaining a first polarization image polarized in the first direction and a second polarization image polarized in a second direction while the object is being illuminated with the first illumination light and obtaining a third polarization image polarized in the first direction and a fourth polarization image polarized in the second direction while the object is being illuminated with the second illumination light; and a processing unit that receives the first, second, third, and fourth polarization images from the polarization imaging device and detects a condition of a second surface of the object on the basis of a difference between a sum of the first polarization image and the fourth polarization image and a sum of the second polarization image and the third polarization image, the second surface being at a side opposite to a side of the first surface.

In one embodiment, the processing unit includes a droplet detecting unit that detects a droplet on the second surface of the object.

In one embodiment, the polarization imaging device includes an image sensor, and a polarizing plate disposed between an imaging plane of the image sensor and the object, the polarizing plate including at least one first polarizer that transmits light polarized in the first direction and at least one second polarizer that transmits light polarized in the second direction.

A polarization image processing apparatus according to another aspect of the present disclosure includes an illumination unit disposed such that an illumination axis substantially coincides with an imaging axis, the illumination unit illuminating an object with circularly polarized illumination light obtained by combining first linearly polarized light and second linearly polarized light with a phase difference provided therebetween, the first linearly polarized light and the second linearly polarized light being respectively polarized in a first direction and a second direction orthogonal to the first direction; a polarization imaging device that receives returning light including circularly polarized light reflected by the object, the polarization imaging device including a light dividing unit that divides the returning light into four light components, the polarization imaging device simultaneously obtaining a first polarization image, a second polarization image, a third polarization image, and a fourth polarization image, the first polarization image being obtained by causing the returning light to successively pass through a phase shifter that causes a phase shift for changing a state of the returning light to a state of linear polarization in the first direction and a polarizer whose direction of polarization is the first direction, the second polarization image being obtained by causing the returning light to successively pass through a phase shifter that causes a phase shift for changing a state of the returning light to a state of linear polarization in the first direction and a polarizer whose direction of polarization is the second direction, the third polarization image being obtained by causing the returning light to successively pass through a phase shifter that causes a phase shift for changing a state of the returning light to a state of linear polarization in the second direction and a polarizer whose direction of polarization is the first direction, and the fourth polarization image being obtained by causing the returning light to successively pass through a phase shifter that causes a phase shift for changing a state of the returning light to a state of linear polarization in the second direction and a polarizer whose direction of polarization is the second direction; and a processing unit that performs image processing on the basis of a difference between a sum of the first polarization image and the fourth polarization image and a sum of the second polarization image and the third polarization image.

An example of the basic structure of a non-limiting and exemplary embodiment of the present disclosure will now be described.

A polarization image processing apparatus according to an aspect of the present disclosure includes an illumination unit arranged such that an illumination axis substantially coincides with an imaging axis. Here, "substantially coincides" means that the angle between the axes is in the range of 0° to 30°. The illumination unit illuminates an object with first illumination light and second illumination light alternately, the first illumination light being polarized in a first direction and the second illumination light being polarized in a second direction that crosses the first direction. Here, "an illumination axis substantially coincides with an imaging axis" means that "an illumination axis of the first illumination light and an illumination axis of the second illumination light substantially coincide with the imaging axis". The angle between the first and second directions may be set in the range of, for example, 45° to 135°, and is typically 90° or about 90°. In the present disclosure, the illumination of the object with the first illumination light and the second illumination light "alternately" does not exclude the case where illumination with another illumination light (third illumination light) is performed between the illuminations with the first illumination light and the illumination with the second illumination light.

According to this aspect, the polarization image processing apparatus includes a splitter that splits returning light that returns from the object into at least two returning light components, a first polarization imaging device that receives one of the returning light components, and a second polarization imaging device that receives the other one of the returning light components. The first polarization imaging device obtains a first polarization image (L0C0) polarized in the first direction while the object is being illuminated with the first illumination light, and obtains a second polarization image (L90C0) polarized in the first direction while the object is being illuminated with the second illumination light. The second polarization imaging device obtains a third polarization image (L0C90) polarized in the second direction while the object is being illuminated with the first illumination light, and obtains a fourth polarization image (L90C90) polarized in the second direction while the object is being illuminated with the second illumination light.

The polarization image processing apparatus further includes a processing unit that detects a condition of the object. The processing unit receives the first, second, third, and fourth polarization images from the first and second polarization imaging devices, and detects the condition of the object on the basis of a difference between the sum of the first polarization image (L0C0) and the fourth polarization image (L90C90) and the sum of the second polarization image (L90C0) and the third polarization image (L0C90). More specifically, a condition of a surface of a transparent or translucent object at a side opposite to a light incident side of the object is detected.

Here, L0 denotes illumination light with a polarization direction that is at an angle of 0 degrees with respect to a certain direction, and L90 denotes illumination light with a polarization direction that is at an angle of 90 degrees with respect to the certain direction. Thus, LX denotes illumination light with a polarization direction that is at an angle of X degrees with respect to the certain direction.

L0C0 represents the observed state, the observed brightness, or the observed image obtained by using a polarizer (analyzer) with a polarization direction at an angle of 0 degrees with respect to the certain direction when the illumination light with a polarization direction at an angle of 0 degrees with respect to the certain direction is emitted.

L0C90 represents the observed state, the observed brightness, or the observed image obtained by using a polarizer (analyzer) with a polarization direction at an angle of 90 degrees with respect to the certain direction when the illumination light with a polarization direction at an angle of 0 degrees with respect to the certain direction is emitted.

L90C0 represents the observed state, the observed brightness, or the observed image obtained by using a polarizer (analyzer) with a polarization direction at an angle of 0 degrees with respect to the certain direction when the illumination light with a polarization direction at an angle of 90 degrees with respect to the certain direction is emitted.

L90C90 represents the observed state, the observed brightness, or the observed image obtained by using a polarizer (analyzer) with a polarization direction at an angle of 90 degrees with respect to the certain direction when the illumination light with a polarization direction at an angle of 90 degrees with respect to the certain direction is emitted.

Thus, LXCY represents the observed state, the observed brightness, or the observed image obtained by using a polarizer (analyzer) with a polarization direction at an angle of Y degrees with respect to the certain direction when the illumination light with a polarization direction at an angle of X degrees with respect to the certain direction is emitted.

In the above-described example of the polarization image processing apparatus, the illumination unit is configured to illuminate the object with the first illumination light and the second illumination light alternately, the first illumination light being polarized in the first direction and the second illumination light being polarized in the second direction that crosses the first direction. However, as described below, the object may instead be illuminated with circularly or elliptically polarized light in which a component polarized in the first direction and a component polarized in the second direction that crosses the first direction are combined together with a certain phase therebetween. The illumination unit may have various structures, and the structure thereof is not limited to those described in the embodiments described below.

Embodiments of the present disclosure will be described in detail with reference to the drawings. However, unnecessarily detailed descriptions may be omitted. For example, detailed descriptions of well-known items and repetition of descriptions of components having the same structures may be omitted to avoid unnecessarily redundant descriptions and facilitate understanding for persons skilled in the art.

The accompanying drawings and the following description are provided to allow persons skilled in the art to fully understand the present disclosure, and are not intended to limit the subject matter described in the claims.

First Embodiment

FIG. 1 illustrates the procedure of an image processing method according to a first embodiment of the present disclosure.

An object is illuminated with illumination light L, which is linearly polarized light having an electric field oscillation plane at a polarization angle that is temporally alternately switched between 0° (horizontal) and 90° (vertical) on a plane perpendicular to the travelling direction of the light. For simplicity, in the following description, the state of polarization in which the electric field oscillation plane is at a polarization angle of 0° (horizontal) on the plane perpendicular to the travelling direction of the light may be referred to as "0°", and the state of polarization in which the electric field oscillation plane is at a polarization angle of 90° (vertical) on the plane perpendicular to the travelling direction of the light may be referred to as "90°". A receiving camera C receives returning light, divides the returning light into two light components, and performs two types of polarization imaging processes in parallel by using linear polarizing filters having polarization transmission axes in the directions of 0° (horizontal) and 90° (vertical) on a plane, similar to the illumination light. Thus, when the state of polarization of the illumination light L is 0°, a parallel-Nicols image L0C0 and a crossed-Nicols image L0C90 are obtained. When the state of polarization of the illumination light L is 90°, a crossed-Nicols image L90C0 and a parallel-Nicols image L90C90 are obtained.

In the case where two polarization images are captured from two light components into which the returning light is divided while the state of polarization of the linearly polarized illumination light L is fixed to 0° or 90°, the two polarization images are captured by two imaging systems having different imaging characteristics. Therefore, when a polarization difference image is obtained by determining the difference between the two images, the obtained image includes the difference in imaging characteristics.

Accordingly, two polarization images may be captured from linearly polarized illumination light L whose state of polarization is 0° and linearly polarized illumination light L whose state of polarization is 90° by using only one of the two different imaging systems. In this case, the two polarization images are captured by using two illumination systems having different illumination characteristics such as illuminance distributions and spectrums. Therefore, when a polarization difference image is obtained by determining the difference between the two images, the obtained image includes the difference in illumination characteristics.

According to the present embodiment, an average polarization difference image is generated by using four images in total, the four images being obtained by switching the polarization direction of the illumination light L. When the polarization direction of the illumination light L is switched, the roles of the two imaging systems of the camera C switch between parallel-Nicols and crossed-Nicols. Therefore, the averages of the images obtained by using the two different imaging systems and the two different illumination systems can be determined. More specifically, images Iav, which include an average parallel-Nicols image Iav(∥) and an average crossed-Nicols image Iav(⊥), can be generated as images captured by a virtual imaging system having intermediate characteristics between the characteristics of the two different imaging systems.

$$Iav(\|)=[L0C0+L90C90]/2$$

$$Iav(\perp)=[L0C90+L90C0]/2 \quad (1)$$

An average polarization difference image Idif is calculated from the images Iav.

$$Idif=Iav(\|)-Iav(\perp) \quad (2)$$

In the thus-generated average polarization difference image, the difference between the characteristics of the two imaging systems and the difference between the characteristics of the two different illumination systems are canceled. Therefore, satisfactory image quality can be maintained even when the gain-up process or the like is performed in the following step of image processing.

In this specification, "average" means that pixel values of a plurality of images are added in units of pixels, and it is not necessary to divide the sum by the number of images. In the example of Equations (1), the sum is divided by 2, which is the number of images. However, it is not necessary to divide the sum by 2.

In the above-described examples of Equations (1) and (2), the difference is calculated after the averages are determined. However, differences may be calculated first, and then the average of the differences may be determined. More specifically, the average of the difference "L0C0−L0C90" and the difference "L90C0−L90C90" may be determined by adding the differences.

Thus, according to the present embodiment, the first, second, third, and fourth polarization images are obtained by two polarization imaging devices, and the condition of the object (shape of irregularities on the surface) can be detected on the basis of the difference between the sum of the polarization image L0C0 and the polarization image L90C90 and the sum of the polarization image L90C0 and the polarization image L0C90.

When the average of the images Iav is determined, a brightness image according to the related art obtained by brightness imaging in which non-polarized illumination light is used can be obtained. This is because an image in which the influences of polarizations of the illumination light L and the imaging systems C are all canceled can be obtained, as is clear from the following equation:

$$Iad=[Iav(\|)+Iav(\perp)]/2=[L0C0+L0C90+L90C0+L90C90]/4$$

The structure of a polarization image processing apparatus according to the present embodiment will now be described.

Figure 2A:
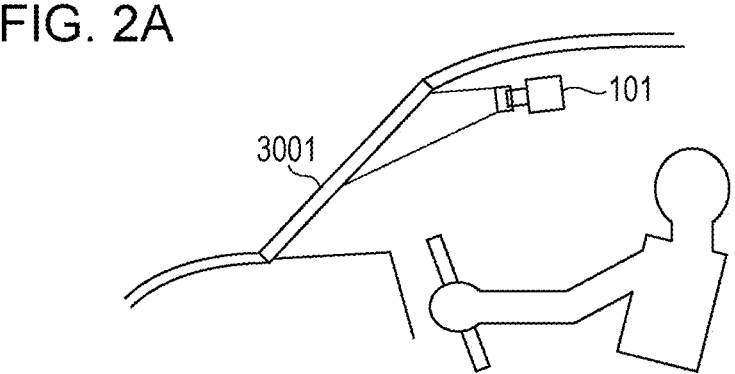
FIGS. 2A to 2C illustrate an imaging unit that serves as a polarization imaging apparatus according to the first embodiment of the present disclosure.

FIG. 2A illustrates an example of a position at which an imaging unit 101 according to the present embodiment is installed. The imaging unit 101 is installed in a vehicle, and captures an image of an external scene through a windshield 3001. The imaging unit 101 functions as an on-board camera. The "external scene" includes objects located outside the vehicle whose images can be captured through the windshield 3001. For example, a road surface, a vehicle on the opposing lane, a traffic signal, etc., may be included in the external scene. The image of the external scene captured by the imaging unit 101 is subjected to known processes and used to provide assistance to the driver. The imaging unit 101 according to the present embodiment is capable of not only capturing the image of the external scene, but also monitoring the condition of the windshield 3001 and detecting the surface condition of the windshield 3001. More specifically, raindrops on the outer surface of the windshield 3001 (surface at the side opposite to the light incident side) can be detected.

Figure 2B:
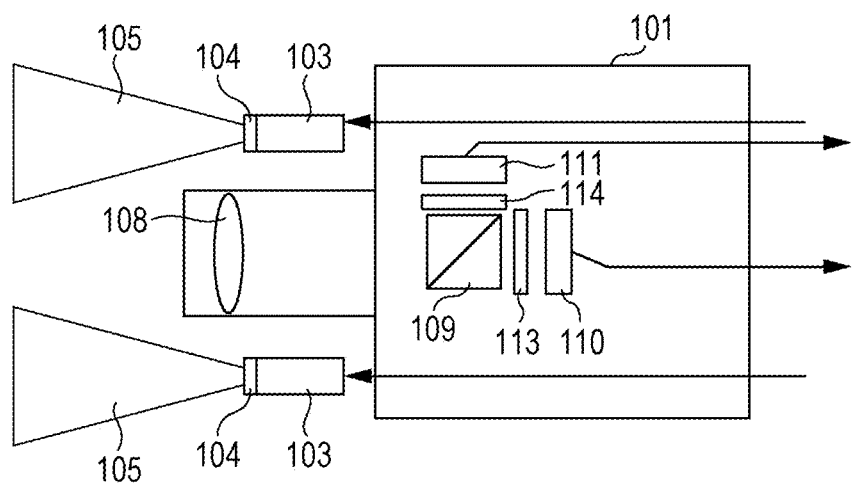

FIG. 2B illustrates an example of the structure of the imaging unit 101 according to the present embodiment. The imaging unit 101 is connected to an image processing unit, which will be described below. A portion of the processing unit or the entirety of the processing unit may be disposed outside the vehicle and connected to the imaging unit (on-board camera) 101 disposed in the vehicle through a network.

Illumination light has a wavelength selected from an infrared band (for example, about 900 nm to 1000 nm), so that the driver or the vehicle on the opposing lane is not affected. Alternatively, white light may be used as the illumination light. A lens suitable for capturing the image of the external scene in a range from infinity to several meters from the lens may be used as an objective lens 108.

Figure 2C:
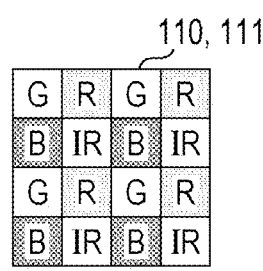

FIG. 2C is a schematic diagram illustrating a portion of a pixel array provided on each of light-receiving surfaces of imaging devices 110 and 111 used in the present embodiment. The imaging devices 110 and 111 are single-plate color imaging devices. Pixels arranged in rows and columns on an imaging plane include not only R, G, and B pixels for a visible-light band but also IR pixels for an infrared band. When the imaging unit 101 is operated in a mode for capturing the image of the external scene to prove assistance to the driver, the illumination light is turned off and a normal full-color image is generated by the R, G, and B pixels. When the imaging unit 101 is operated in a mode for monitoring the condition of the windshield, polarized light in the infrared band is emitted and an infrared image is generated by the IR pixels.

Figure 3:
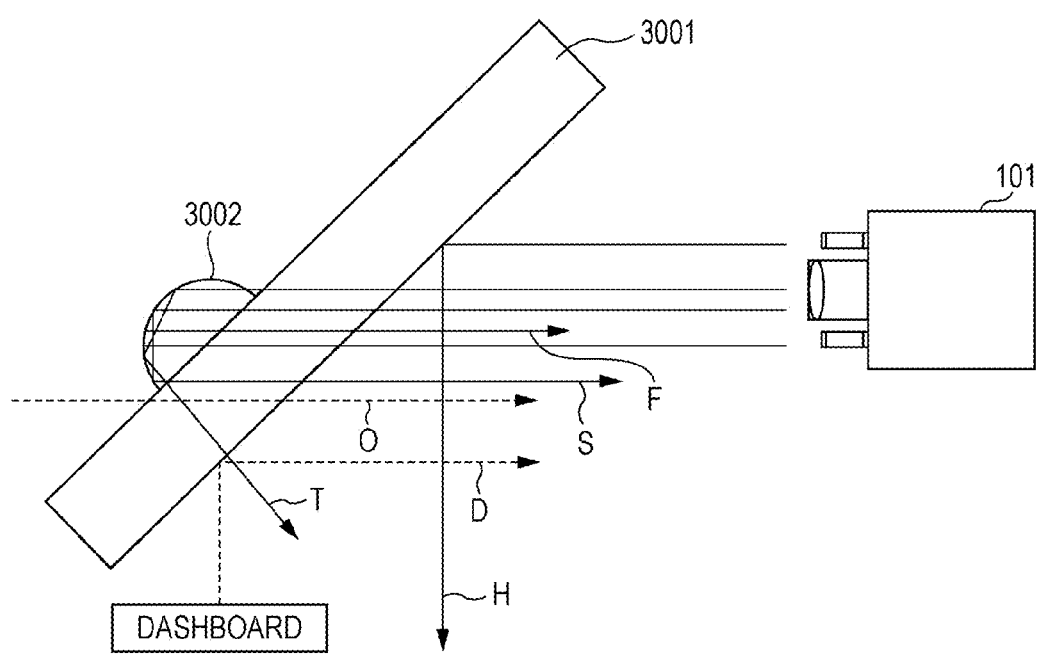
FIG. 3 illustrates paths of light rays that are incident on the imaging unit.

FIG. 3 is a schematic diagram illustrating light rays that are reflected by the windshield 3001 when the windshield 3001 is illuminated with the polarized illumination light. A raindrop 3002 is retained on the windshield 3001. As illustrated in FIG. 3, rays of the polarized illumination light are reflected by the surface of the windshield 3001 or the raindrop 3002. A part of the reflected light is incident on the camera.

In the present embodiment, coaxial illumination is realized, so that an imaging axis of the camera and an optical axis of the polarized illumination light are substantially parallel. The windshield 3001 is inclined with respect to the optical axis of the polarized illumination light. Therefore, a light ray (H), which is included in the polarized illumination light, is regularly reflected with respect to the light source and cause halation, and does not return to the camera. Light that is reflected and refracted by the raindrop 3002 can return to the camera.

A light ray (F) which is emitted from the illumination light source, passes through the windshield 3001, is regularly reflected by the raindrop 3002, and returns to the camera maintains the state of polarization. In other words, the light reflected by the raindrop 3002 is linearly polarized light that is polarized in the same direction as the direction of polarization of the linearly polarized light emitted from the illumination light source. A light ray (S) which passes through the windshield 3001, is reflected twice by the raindrop 3002, and returns to the camera is also linearly polarized light that is polarized in the same direction as the direction of polarization of the linearly polarized light emitted from the illumination light source. A light ray (T) does not return to the camera by being reflected once or twice.

Most of light (O) from the external scene is not polarized. Light (D), which is external light that passes through the windshield 3001, is reflected by the dashboard, and then is reflected by the windshield 3001 may have an angle close to the Brewster's angle. Therefore, the light (D) is often polarized in the horizontal direction (0°).

Figure 4:
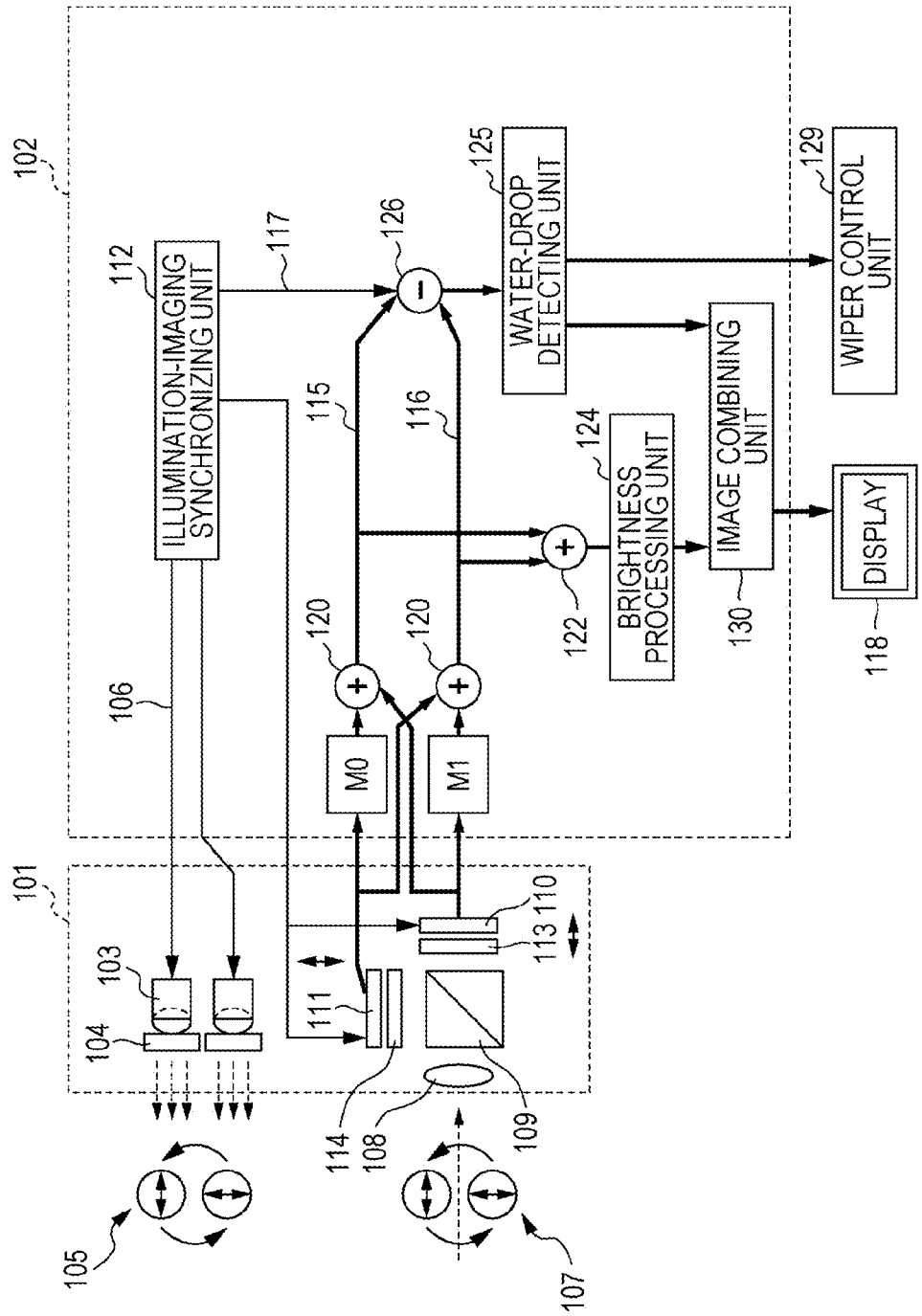
FIG. 4 illustrates a polarization imaging apparatus according to the first embodiment of the present disclosure.

FIG. 4 is a schematic diagram illustrating the overall structure of a polarization image processing apparatus according to the present embodiment.

In the present embodiment, in a rain-drop detection mode, two types of linearly polarized infrared light 105, in which the direction of the electric field oscillation plane is 0° and 90°, are temporally alternately emitted toward an object, and returning light 107 that is reflected by the object is divided into two components along two optical paths by a beam splitter 109. The two components into which the returning light 107 has been divided are received by two single-plate color imaging devices 110 and 111 through polarizing plates 113 and 114, respectively, and are subjected to color imaging.

In FIG. 4, polarization imaging is performed at a polarization transmission angle of 0° by the color imaging device 110 and at a polarization transmission angle of 90° by the color imaging device 111. The polarizing plates 113 and 114 may be omitted when the beam splitter 109 is replaced with a polarizing beam splitter.

In the present embodiment, the polarized illumination light 105 is generated by light sources 103 and polarizing plates 104 arranged in an end portion of the imaging unit 101. The light sources 103 may be, for example, light emitting diodes (LEDs), lasers, or organic electroluminescent (EL) devices. The timing at which the state of polarization of the illumination light is switched and images are captured is controlled by an illumination-imaging synchronizing unit 112. The captured images are stored in image memories M0 and M1, and an average calculation process, a brightness generation process, and a polarization difference determination process are performed for the stored images and images captured at the next illumination switching time.

The average parallel-Nicols image Iav(||) and the average crossed-Nicols image Iav(⊥) are temporally alternately transmitted by an image signal 115 and an image signal 116. More specifically, when the polarization direction of the illumination light is 0°, the image signal 115 represents the average parallel-Nicols image Iav(||) and the image signal 116 represents the average crossed-Nicols image Iav(⊥). In the average polarization difference process, the image signal 116 is subtracted from the image signal 115. When the polarization direction of the illumination light is 90°, the image signal 116 represents the average parallel-Nicols image Iav(||) and the image signal 115 represents the average crossed-Nicols image Iav(⊥). In the average polarization difference process, the image signal 115 is subtracted from the image signal 116.

The switching control is performed on the basis of a difference direction signal 117. A brightness image generated by a brightness generating unit 122 is displayed on the display 118 as a color moving image of a normal imaging mode by a brightness generating unit 124. The average polarization difference image generated by a polarization difference generating unit 126 is transmitted to a droplet detecting unit 125. The droplet detecting unit 125 extracts high-brightness regions of raindrops by performing an image binarization process based on the average polarization difference image, and then performs a subsequent process to detect raindrop regions.

An image combining unit 130 may generate, for example, an image from which the detected droplets are removed and displays the generated image on the display 118 as a color image of a polarization imaging mode. A wiper control unit 129 may start the operation of wipers or adjust the operational speed of the wipers in accordance with the output from the droplet detecting unit 125.

Figure 5:
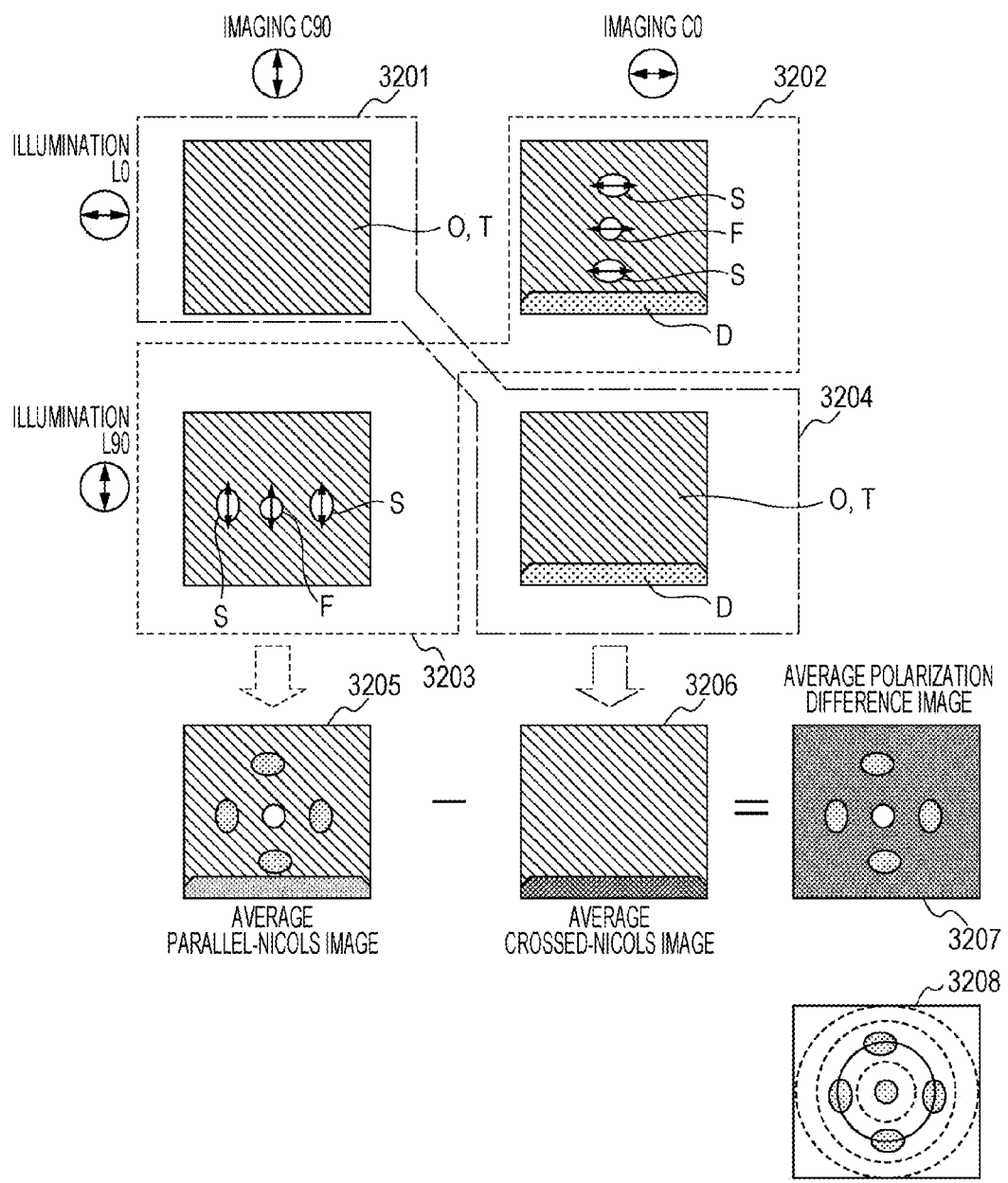
FIG. 5 illustrates images of a raindrop on a windshield and the result of a polarization difference process performed on the images.

FIG. 5 illustrates images of a raindrop on the windshield and the result of a polarization difference process thereof. Images 3201 and 3202 are obtained when the polarized light L is polarized in the direction of 0° and the polarization angles of the imaging systems C are 90° and 0°, respectively. Images 3203 and 3204 are obtained when the polarized light L is polarized in the direction of 90° and the polarization angles of the imaging systems C are 90° and 0°, respectively. The image 3202 shows three local elliptical regions (F) and (S) having a high brightness in the region corresponding to a single raindrop. In the regions (F) and (S), the brightness is high since a large amount of illumination light returns to the camera while a polarized component having a polarization angle of 0° is maintained. In contrast, background scenes (T) and (O) are images of non-polarized light corresponding to the external scene, and the brightness thereof is reduced to ½ of the original scene brightness. A region (D), which corresponds to the light reflected by the dashboard, shows halation due to the reflected light, which is polarized at the polarization angle of 0°. In the image 3201, the polarized returning light that returns from the raindrop is entirely blocked since the returning light of the illumination light is in the crossed-Nicols state. Therefore, only an image having a brightness that is ½ of the brightness of the non-polarized image of the external scene is captured, and the light reflected by the dashboard is also blocked.

The image 3203 shows three local elliptical regions (F) and (S) having a high brightness in the region corresponding to the single raindrop. The brightness is high in the regions (F) and (S) of the raindrop in which light returns to the camera while a polarized component having a polarization angle of 90° is maintained. However, the background scenes (T) and (O) are images of non-polarized light corresponding to the external scene, and therefore the brightness thereof is reduced to ½. In the region (D), which corresponds to the light reflected by the dashboard, the reflected light is polarized and is therefore blocked. In the image 3204, non-polarized images (O) and (T) of the external scene, whose brightness is reduced to ½, and an image (D) corresponding to the light reflected by the dashboard and having a polarization angle of 0°, are captured. All of these images are infrared images since the imaging devices have sensitivity in the infrared wavelength range and the images are captured by infrared pixels IR of polarization imaging devices.

An average parallel-Nicols image 3205 is obtained by taking the average of the images 3202 and 3203 among the above-described four types of images. Therefore, the regions (F) and (S), which are the high-brightness regions of the raindrop, the external scene (O) and (T) in which the brightness is reduced to ½, and the region (D) in which the brightness is reduced to ½ are captured. In an average crossed-Nicols image 3206, the external scene (O) and (T) in which the brightness is reduced to ½ and the region (D) in which the brightness is reduced to ½ are captured. In an average polarization difference image 3207, which is obtained by subtracting the image 3206 from the image 3205, the regions (O), (T), and (D), in which the external scene is captured, are eliminated and turn black, and only the high-brightness regions (F) and (S) of the raindrop are extracted. The droplet detecting unit performs image processing on the polarization difference image and estimates the regions to be integrated into a single raindrop while changing the radius from the high-brightness point at the center to the surrounding bright points. This process can be realized through a well-known binary image expansion process.

In the present embodiment, the average of the effects caused by temporally switching the illumination light emitted toward the windshield between two types of illumination light is determined, and the average of the parallel-Nicols and crossed-Nicols images is determined at the same time. Therefore, compared to the structure of the related art, the robustness and versatility are improved.

Figure 6:
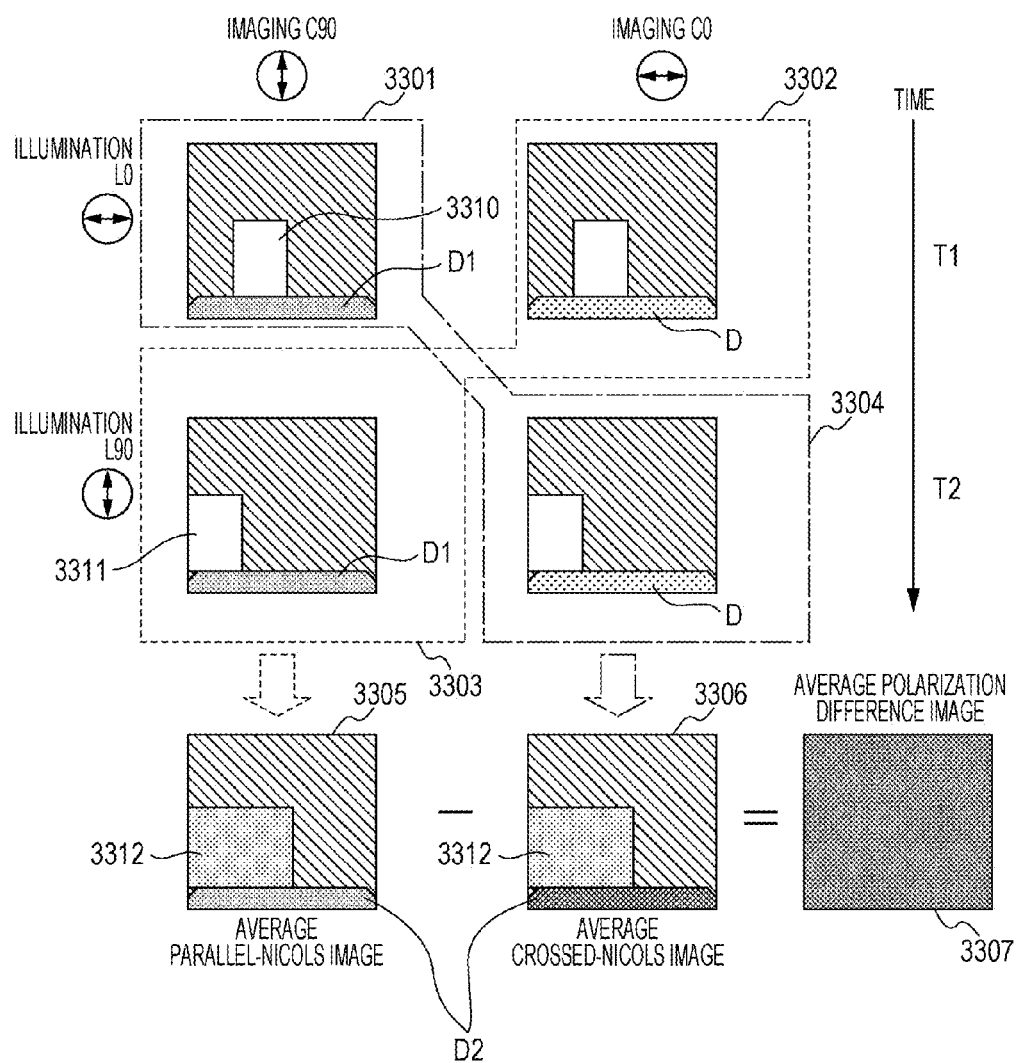
FIG. 6 illustrates the detailed process for removing an external scene and a reflection of a dashboard.

FIG. 6 illustrates this effect by using an example of elimination of the external scene and the reflection of the dashboard. When it is assumed that illumination and imaging using the illumination light L0 are performed at time T1 and illumination and imaging using the illumination light L90 are performed at time T2, the external scene may greatly vary during the period between T1 and T2 since the vehicle is moving.

Referring to FIG. 6, an external object 3310 is in a central region in each of two images 3301 and 3302 captured at time T1, and is moved to a region 3311 near the left end in each of images 3303 and 3304 captured at time T2.

With regard to an image of the reflection of the dashboard, there may be a case where the degree of polarization in the region (D) corresponding to the reflection of the dashboard is low, or no polarization occurs. Owing to the influence of the curvature of the windshield or the like, there is a possibility that the light reflected by the inner surface of the windshield will not be polarized in the horizontal direction (0°) and the angle of the polarization axis will vary depending on the position. In this case, the reflected light cannot be completely blocked by setting the angle of the polarization axis to 90° at the imaging side, and the brightness often remains. Regions (D1) in the images 3301 and 3303 show the reflection that has remained.

However, in the average parallel-Nicols image 3305 and the average crossed-Nicols image 3306, the images 3310 and 3311 are integrated as a sum region 3312 in which the average brightness is the average of the brightnesses of the object and the background. In addition, the region (D) corresponding to the reflection of the dashboard is also changed to a region (D2) having the same brightness as a result of the process of taking the average. Accordingly, the brightness is changed to zero in the average polarization difference image 3307. Thus, the temporal change in the external scene and the variation in the state of polarization depending on the position in the region corresponding to the reflection of the dashboard can both be cancelled and eliminated. In other words, the influence of movement of the external scene due to the movement of the vehicle and the influence of the reflection light from the dashboard in which the state of polarization is not uniform can be reliably eliminated. Thus, high robustness and versatility can be provided.

Figure 7:
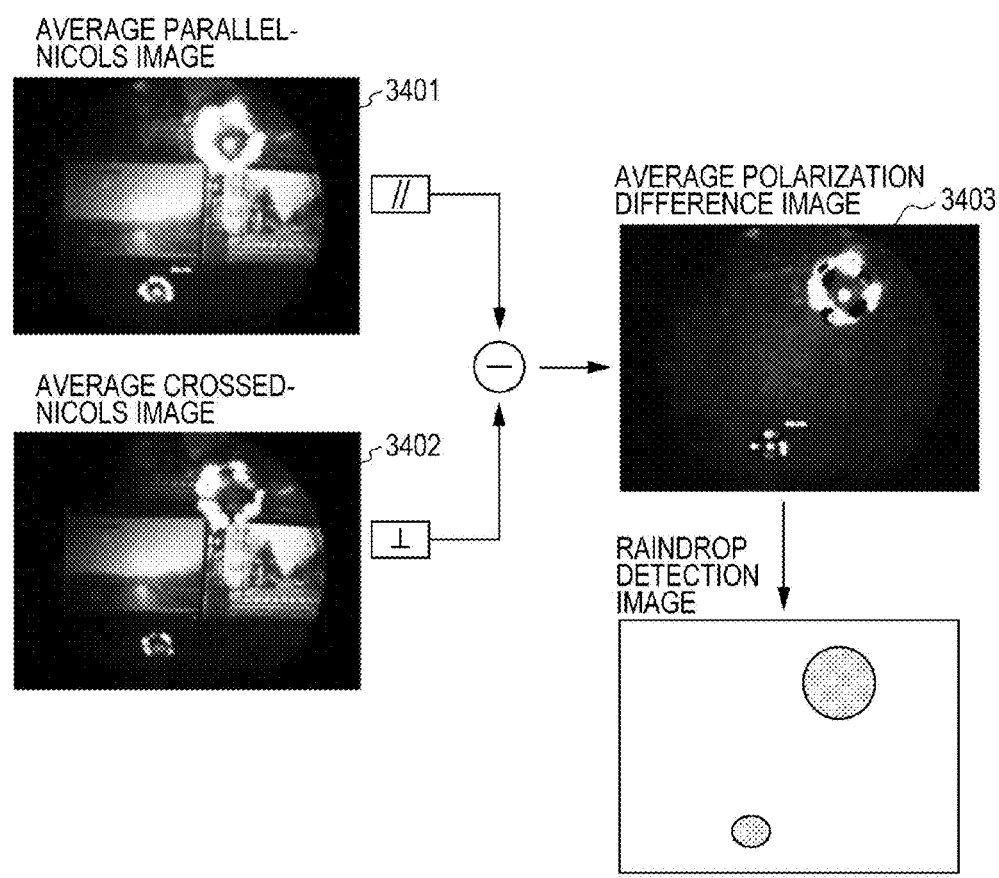
FIG. 7 illustrates the result of an experiment in which raindrops on an acrylic board were used.

FIG. 7 illustrates the result of polarization imaging and image processing for detecting raindrops. An experiment was performed in which polarized illumination light was emitted from a position on the camera side of a transparent acrylic board that was inclined at 45°, and an average parallel-Nicols image 3401 and an average crossed-Nicols image 3402 were obtained by capturing images of an external scene through droplets retained on the outer surface of the acrylic board. The measured value of the optical extinction ratio of the polarization imaging apparatus including the optical system was about 80:1, and was lower than 100:1. An average polarization difference image 3403 was obtained from the average parallel-Nicols image 3401 and the average crossed-Nicols image 3402. In the average polarization difference image 3403, the background scene is eliminated and is shown as a black region, and only high-brightness regions that correspond to the raindrops are extracted. Then, a raindrop detection process is performed. Finally, an evaluation value, such as the area of the raindrops, is calculated and transmitted to the wiper control unit 129.

As described above, according to the present embodiment, the raindrops can be detected even when the optical extinction ratio of the camera is 100:1 or less. In addition, compared to the structure of the related art, the degree of freedom with regard to the arrangement of the camera in the vehicle and the angle of the illumination light with respect to the windshield can be increased. In addition, it is not necessary to finely adjust the polarization camera in accordance with the variation in the state of polarization depending on the position due to the curvature of the windshield.

Figure 8A:
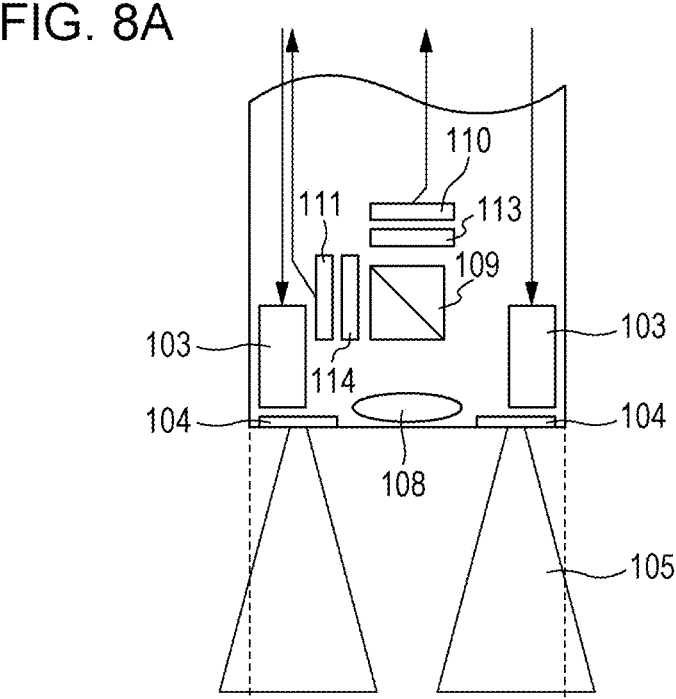
FIGS. 8A and 8B illustrate the structure of a camera according to the first embodiment of the present disclosure.
Figure 8B:
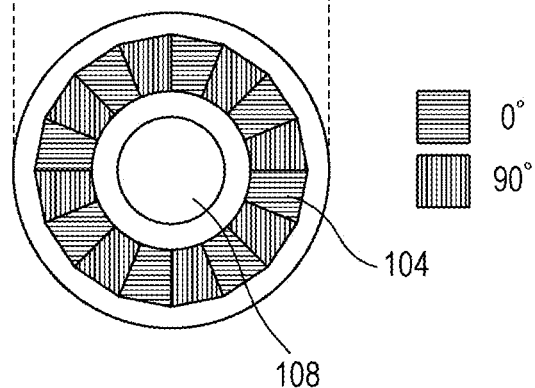

FIGS. 8A and 8B are a sectional view and a front view, respectively, illustrating an example of the structure of the imaging unit 101. The structure of the imaging unit 101 is not limited to this.

As illustrated in FIG. 8B, the light sources 103 and the polarizing plates 104 that cover the respective light sources 103 are arranged in a ring-like pattern at the end of the imaging unit. Each light source 103 and the corresponding polarizing plate 104 form a light source segment that can be turned on individually (the number of segments is 16 in FIG. 8B). In this example, the polarization transmission axes of the 16 polarizing plates 104 that are arranged in the ring-like pattern extend in the directions of 0° and 90° alternately. Accordingly, light emitted from the odd-numbered light sources counted from a reference light source is converted into linearly polarized light that is polarized in the direction of 0° by the corresponding polarizing plates 104. Similarly, light emitted from the even-numbered light sources counted from the reference light source is converted into linearly polarized light that is polarized in the direction of 90° by the corresponding polarizing plates 104. The number of light sources 103 (number of segments) is not limited to 16. In addition, the polarizing plates 104 having the polarization transmission axes extending in the direction of 0° and the polarizing plates 104 having the polarization transmission axes extending in the direction of 90° are not necessarily arranged alternately.

The returning light that returns from the object passes through an objective lens 108 that is located around the center of the ring-shaped pattern in which the light sources 103 are arranged, and is guided to a beam splitter 109. The returning light is divided by the beam splitter 109 along two optical paths into two light components, which are processed in parallel by two imaging systems.

In the present embodiment, two groups of light source segments, each group including eight light source segments of the same type that are not next to each other, are alternately selected and turned on, so that the two types of linearly polarized illumination light having orthogonal polarization directions are temporally alternately emitted. As described above, the number of segments and the arrangement of the polarizing plates are not limited. However, preferably, the positions of the light sources that emit light are not shifted by a large amount when the polarization direction of the linearly polarized light is changed.

Figure 9A:
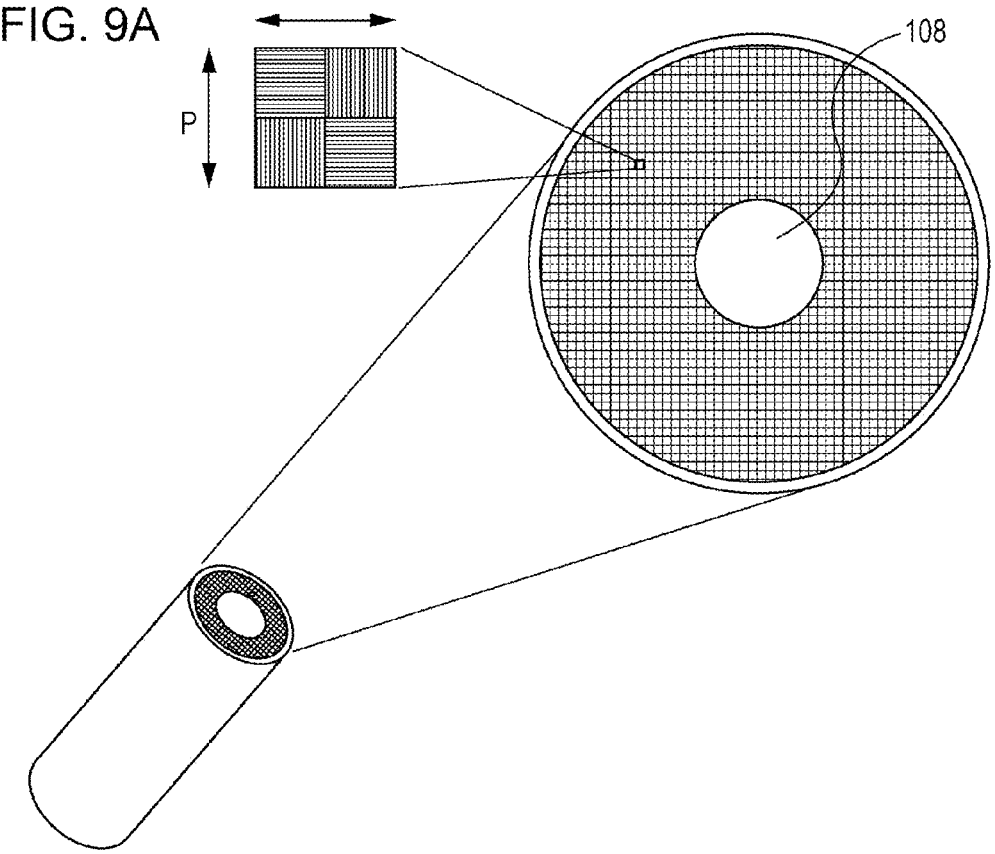
FIGS. 9A and 9B illustrate another example of polarization illumination.

FIG. 9A illustrates another example of an illumination unit that emits polarized illumination light. In this example, the size of illumination pixel units that are successively turned on is sufficiently small, and the number of illumination pixel units is sufficiently large. Thus, the displacement of the positions of light sources that emit light can be reduced to one pixel or less at the imaging side.

Figure 9B:
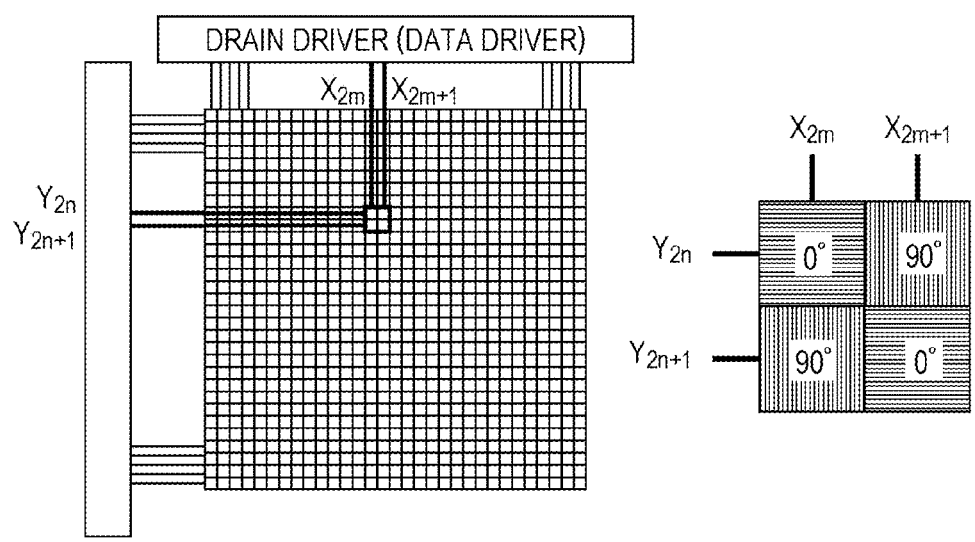

FIG. 9B illustrates the overall structure of the surface illumination unit. The surface illumination unit illustrated in FIG. 9B includes a plurality of pixels that are arranged two dimensionally. Each pixel is driven by an X-axis data driver and a Y-axis data driver. The pixels that are driven by both the X-axis data driver and the Y-axis data driver emit light.

For example, when signal lines of the X-axis data driver whose X coordinates are $X_{2m}$ and signal lines of the Y-axis data driver whose Y coordinates are $Y_{2m}$ are driven, pixels at coordinates $(X_{2m}, Y_{2m})$, where X and Y coordinates are both even numbers, simultaneously emit light. As a result, light having a polarization plane at 0° is emitted.

Similarly, when signal lines of the X-axis data driver whose X coordinates are $X_{2m+1}$ and signal lines of the Y-axis data driver whose Y coordinates are $Y_{2m+1}$ are driven, pixels at coordinates $(X_{2+1m}, Y_{2m+1})$, where X and Y coordinates are both odd numbers, simultaneously emit light. Also in this case, light having a polarization plane at 0° is emitted.

However, at pixels where the X coordinate of the signal line driven by the X-axis data driver and the Y coordinate of the signal line driven by the Y-axis data driver are an odd number and an even number, respectively, or an even number and an odd number, respectively, linearly polarized illumination light having a transmission polarization plane at 90° is emitted.

Such a surface illumination unit is advantageous in that the state of polarization of the illumination light can be changed without changing the illuminance and light distribution over the entire area. When the surface light source is used for illumination, the illumination light can be made uniform. As a result, extremely high regular reflection brightness on the transparent windshield can be reduced and the imaging process can be appropriately performed. The illumination unit in which the polarization plane is rotated is not limited to those including light source segments as described above, and a polarization phase shifter, such as a variable retarder, which utilizes the property of liquid crystal may instead be used.

Figure 10:
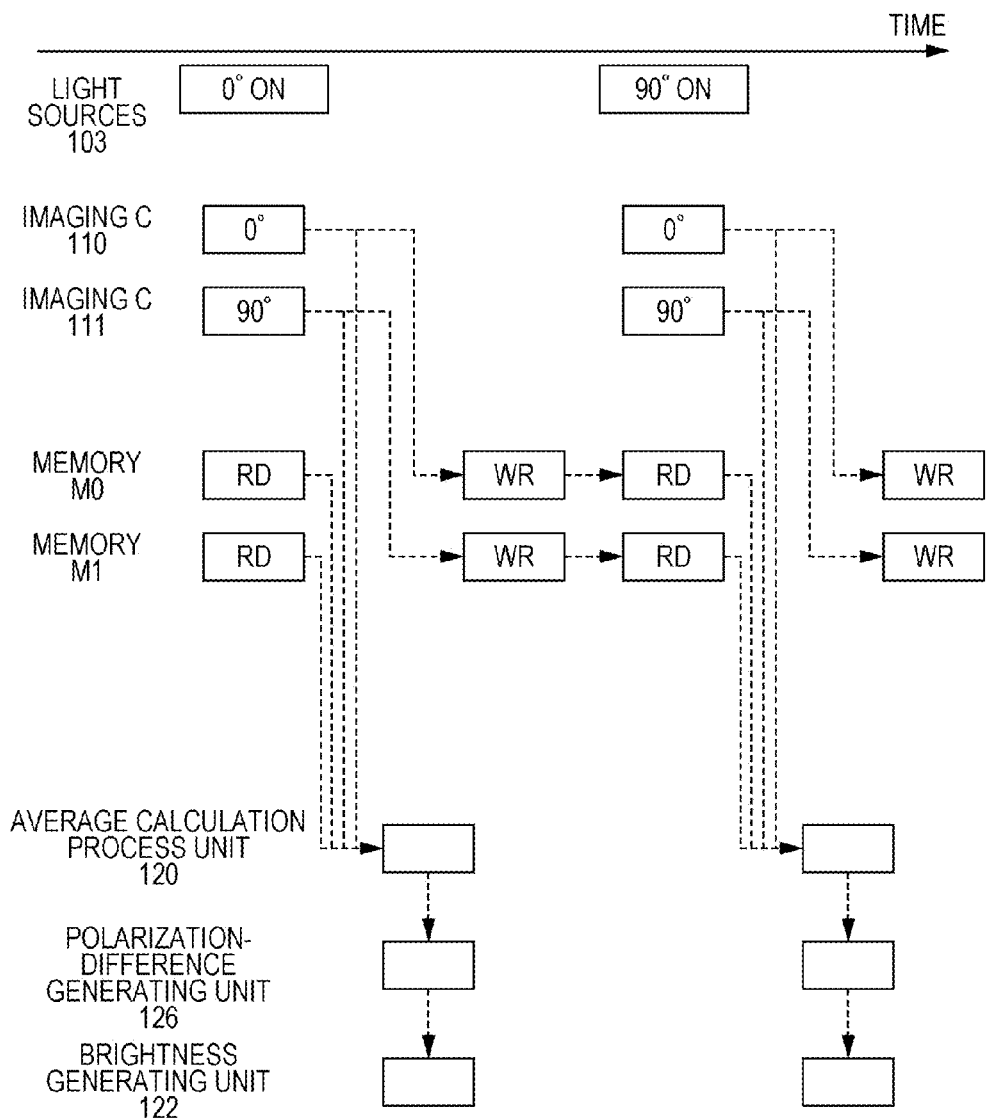
FIG. 10 is a timing chart illustrating the timing for capturing images and reading/writing the images from/to image memories in a polarization imaging mode.

In the above-described example, the light sources 103 are disposed in the imaging unit 101. However, the light sources 103 may instead be separated from the imaging unit 101 as long as the axis of the illumination light and the imaging axis substantially coincide with each other. FIG. 10 is a chart showing the timing of illumination and imaging in the polarization imaging mode according to the embodiment illustrated in FIG. 4. FIG. 10 also shows the timing for reading (RD) and writing (WR) image data from/to memories M0 and M1 capable of storing the image data.

The light sources 103 are turned on such that the angle of transmission axis of the linearly polarized light switches between 0° and 90°. During the time in which each type of light is emitted, the imaging device 110 and the imaging device 111 perform polarization imaging to capture images of a single frame with polarization transmission planes of 0° and 90° in parallel. The image data of the captured images is transmitted to an average calculation process unit 120. At the same time, image data of a previous frame that is read from the image memories M0 and M1 is also transmitted to the calculation process unit 120, and is subjected to an average calculation process together with the image data of the captured images.

The average parallel-Nicols image Iav(∥) and the average crossed-Nicols image Iav(⊥) are transmitted to calculation process units, such as the polarization difference generating unit 126 and the brightness generating unit 122. The generated average polarization difference image is transmitted to the droplet detecting unit 125. The droplet detecting unit 125 extracts high-brightness regions of raindrops by performing an image binarization process based on the average polarization difference image, and then performs a subsequent process to detect raindrop regions.

The image combining unit 130 may generate, for example, an image from which the detected droplets are removed and displays the generated image on the display 118 as a color image of a polarization imaging mode. The wiper control unit 129 may start the operation of wipers or adjust the operational speed of the wipers in accordance with the output from the droplet detecting unit 125.

Figure 11:
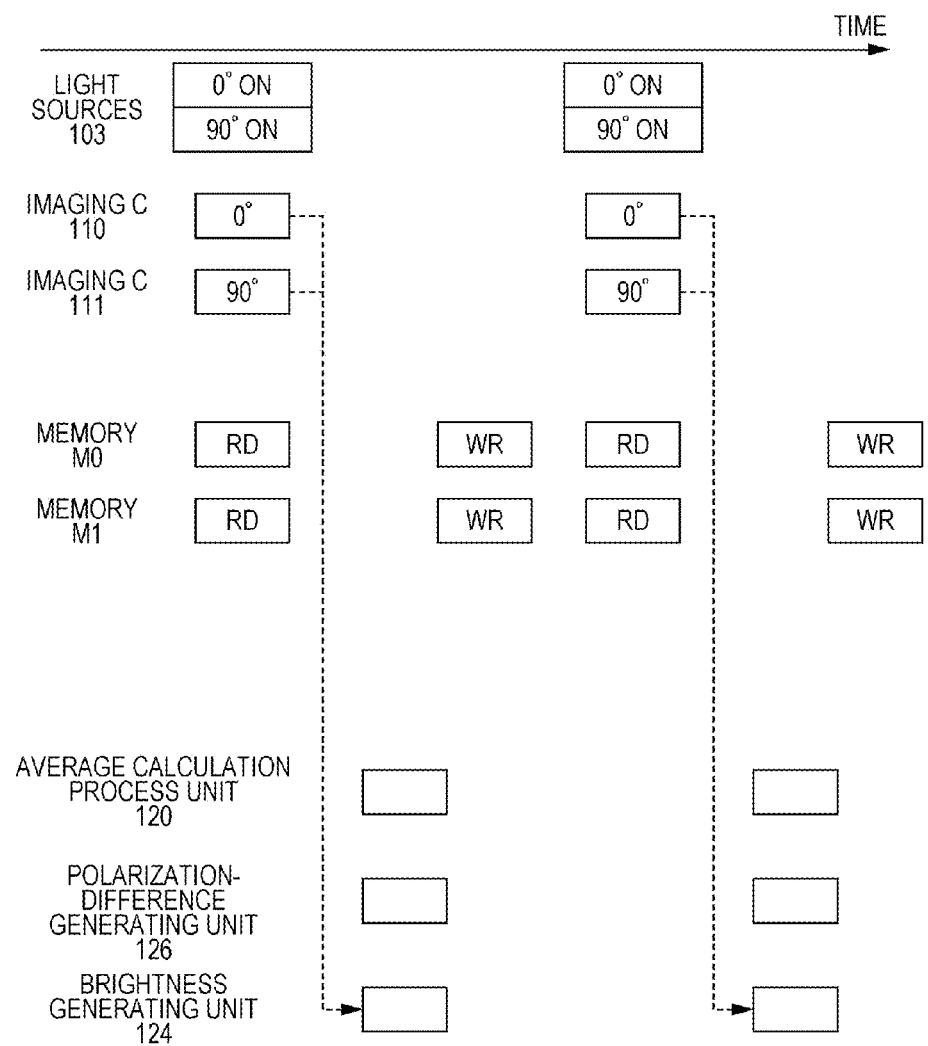
FIG. 11 is a timing chart illustrating the timing for capturing images and reading/writing the images from/to image memories in a normal imaging mode.

FIG. 11 is a chart showing the timing of illumination and imaging in the normal imaging mode according to the embodiment illustrated in FIG. 4. FIG. 11 also shows the timing for reading (RD) and writing (WR) image data from/to the image memories M0 and M1 capable of storing the image data.

The light sources 103 in which the transmission angles of the linearly polarized light are 0° and 90° are simultaneously turned on, so that the emitted light is equivalent to non-polarized light. During the time in which this light is emitted, the imaging device 110 and the imaging device 111 obtain data of images (polarization images) of a single frame with the polarization transmission planes of 0° and 90° in parallel. The obtained image data is transmitted to the brightness generating unit 124, and the average thereof is determined. As a result, polarization imaging is canceled and a normal brightness image is obtained. In this mode, it is not necessary to use the image memories M0 and M1 or the average calculation process unit 120. In addition, since light components having different polarization directions can be emitted at the same time, the amount of illumination light is increased, and the exposure time of the imaging devices is reduced. As a result, a moving image can be captured at a high speed.

According to the related art, it is necessary to eliminate, with a polarizing filter, halation of regularly reflected light that occurs when non-polarized infrared light is emitted toward the windshield. Therefore, the polarizing filter, which is made of a wire grid, is required to have a very high optical extinction ratio. According to the experiments conducted by the present inventor, the optical extinction ratio needs to be higher than or equal to about 100:1, which cannot be easily realized by a polarizing plate made of a wire grid. However, according to the present embodiment, a camera body with which an illumination unit is integrated can be arranged at any position where the camera body does not obstruct the driver, and sufficient performance can be achieved even when the optical extinction ratio is 100:1 or less.

Modification of First Embodiment

Figure 12:
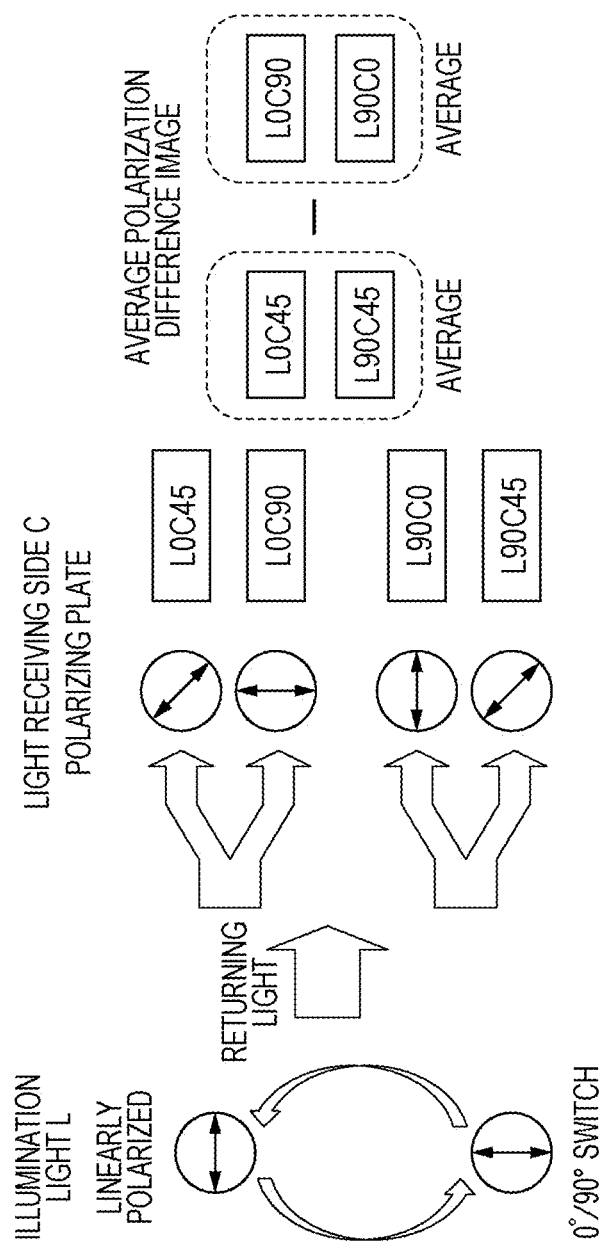
FIG. 12 illustrates a polarization imaging method according to a modification of the first embodiment of the present disclosure.

FIG. 12 illustrates a modification of the first embodiment of the present disclosure. In the embodiment described with reference to FIG. 1, the polarizing plates at the light receiving side C have transmission axes in two directions: 0° and 90°. This modification differs from the embodiment illustrated in FIG. 1 in that polarizing plates at the light receiving side C have transmission axes in three directions: 0°, 45°, and 90°. In other words, in the embodiment illustrated in FIG. 1, images L0C0 and L90C90 obtained while the polarizing directions (transmission axis directions) of the polarizing plates of the imaging systems are parallel to the polarizing direction of the illumination light are used as the parallel-Nicols images. In contrast, in the present modification, images L0C45 and L90C45 obtained while the polarizing directions of the polarizing plates are at an angle of 45° with respect to the polarizing direction of the illumination light are used. These images may be referred to as "oblique-Nicols image". Accordingly, in the polarization imaging mode, when halation of the parallel-Nicols images in the polarization difference images is too large due to inclination or smoothness of the surface of the object, the halation can be reduced.

Figure 13:
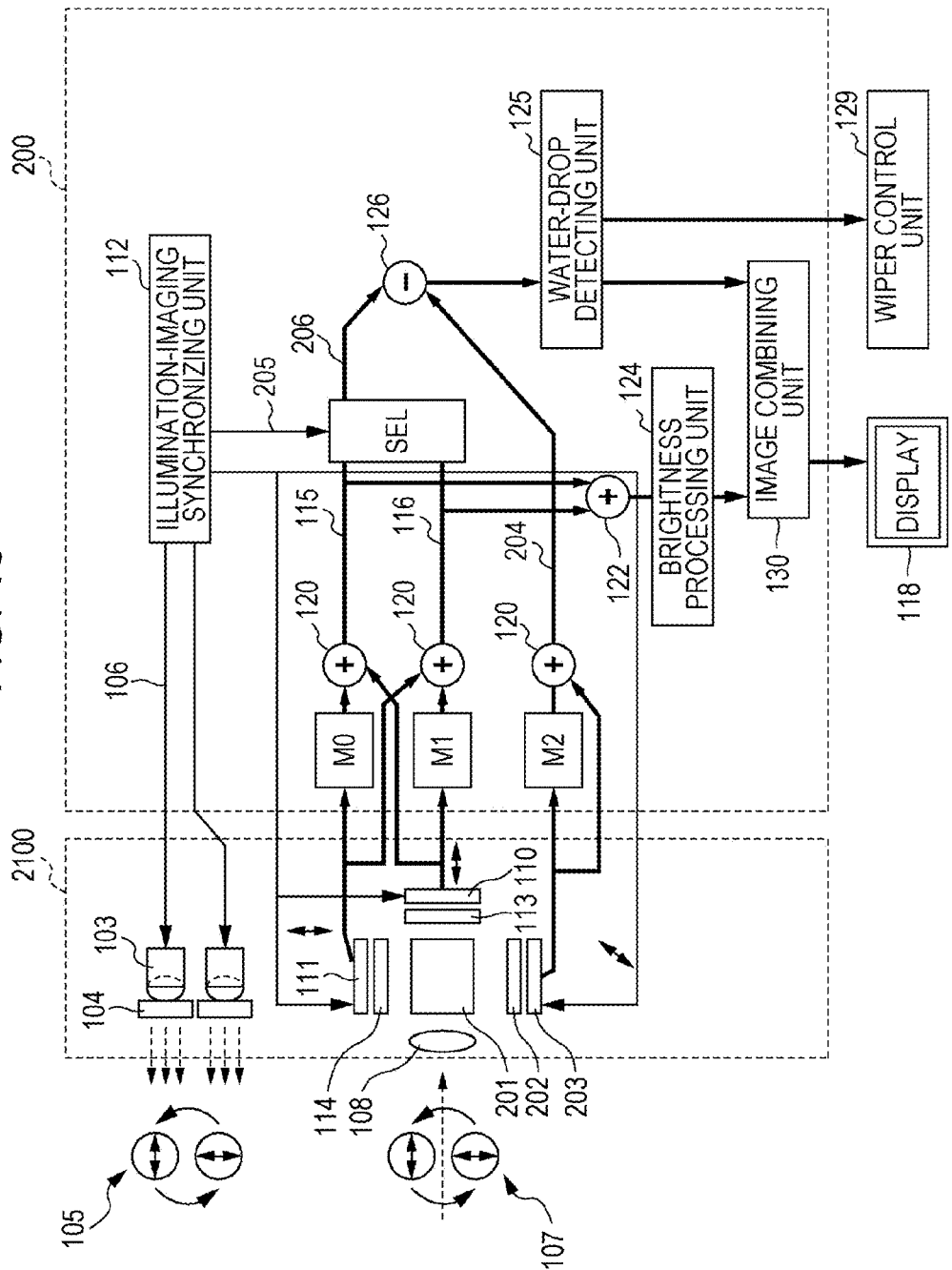
FIG. 13 illustrates the structure of a polarization imaging apparatus according to the modification of the first embodiment of the present disclosure.

FIG. 13 is a schematic diagram illustrating the overall structure of a polarization image processing apparatus according to the present modification. The polarization image processing apparatus according to the present modification includes an imaging unit 2100, a control device 200, and a display 118.

In the present modification, two types of linearly polarized infrared light 105, in which the direction of the electric field oscillation plane is 0° and 90°, are temporally alternately emitted. Returning light 107 that is reflected by an object is divided into three light components along three optical paths by a prism 201. The three light components are caused to pass through polarizing plates 113, 114, and 202, and are subjected to color imaging by three single-plate color imaging devices 110, 111, and 203. In the example illustrated in FIG. 13, polarization imaging is performed at a polarization transmission angle of 0° by the color imaging device 110, at a polarization transmission angle of 90° by the color imaging device 111, and at a polarization transmission angle of 45° by the color imaging device 203.

The timing at which the state of polarization of the illumination light is switched and images are captured is controlled by an illumination-imaging synchronizing unit 112. The captured images are stored in image memories M0, M1, and M2. These images and images captured at the next illumination switching time are subjected to an average calculation process, a brightness generation process, and a polarization difference determination process.

The average parallel-Nicols image Iav(∥) and the average crossed-Nicols image Iav(⊥) are temporally alternately represented by an image signal 115 and an image signal 116. More specifically, when the polarization direction of the illumination light is 0°, the image signal 116 represents the average crossed-Nicols image Iav(⊥). When the polarization direction of the illumination light is 90°, the image signal 115 represents the average crossed-Nicols image Iav(⊥). The selection between them is performed by a selecting unit SEL in accordance with a signal 205. An image corresponding to the average parallel-Nicols image (average oblique-Nicols image) is an average image of the image L0C45 and the image L90C45, and is therefore represented by an image signal 204 obtained as a result of an average calculation process performed by using the image read from the memory M2 and the image captured by the color imaging device 203.

An average polarization difference generating unit 126 subtracts an output 206 of the selecting unit SEL from the image signal 204. A brightness image generated by a polarization-difference brightness generating unit 122 is displayed on the display 118 as a color moving image of a normal imaging mode by a brightness generating unit 124. The average polarization difference image generated by the average polarization difference generating unit 126 is transmitted to a droplet detecting unit 125. The droplet detecting unit 125 extracts high-brightness regions of raindrops by performing an image binarization process based on the average polarization difference image, and then performs a subsequent process to detect raindrop regions.

An image combining unit 130 may generate, for example, an image from which the detected droplets are removed and displays the generated image on the display 118 as a color image of a polarization imaging mode. A wiper control unit 129 may start the operation of wipers or adjust the operational speed of the wipers in accordance with the output from the droplet detecting unit 125.

FIGS. 14A to 14C illustrate a polarization imaging apparatus according to the present modification. The polarization imaging apparatus includes three types of polarizing plates having transmission axes in directions of 0°, 45°, and 90°, and three single-plate color imaging devices.

In the present modification, the operation may be performed in three operation modes, which are an alternate illumination mode illustrated in FIG. 14A, a simultaneous illumination mode illustrated in FIG. 14B, and an illumination off mode illustrated in FIG. 14C. The operation mode may be switched by the driver or be switched automatically at a predetermined time period.

In the modes illustrated in FIGS. 14A and 14B, the light sources are turned on and detection of the condition of the windshield, that is, detection of raindrops, is performed. In the mode illustrated in FIG. 14C, image recognition based on the external scene is performed and drive assistance is activated.

In the alternate illumination mode illustrated in FIG. 14A, detection of raindrops is performed as described in the above-described embodiment. In this mode, of the three single-plate color imaging devices, only two types of images are captured by the imaging device 111, which corresponds to the polarizing plate having the polarization transmission axis in the direction of 0°, and the imaging device 110, which corresponds to the polarizing plate having the polarization transmission axis in the direction of 90°. In other words, no image is captured by the imaging device 203, which corresponds to the polarizing plate having the polarization transmission axis in the direction of 45°.

In the simultaneous illumination mode illustrated in FIG. 14B, two types of linearly polarized illumination light having the polarization directions at the angles of 0° and 90° are simultaneously emitted. Therefore, illumination light that is equivalent to non-polarized illumination light can be obtained.

In the illumination off mode illustrated in FIG. 14C, the polarization imaging camera is operated by using non-polarized illumination light of the scene. Therefore, the condition of the windshield, such as the presence of raindrops, is not detected and polarization imaging for recognition of the external scene is performed. In this mode, since the camera is provided with three types of polarizing plates having transmission axes in directions of 0°, 45°, and 90°, even when the state of polarization varies depending on the position due to, for example, the curvature of the windshield, an image of the external scene from which the influence of the reflected light from the dashboard is efficiently removed can be captured. For example, as described in Japanese Patent No. 4486703, with a polarization imaging apparatus including three types of polarization transmission planes having different angles, three pixel values can be obtained for each pixel position of an image. By optimally determining a sine function curve that passes through these three points and performing a process of subtracting the minimum value of brightness variation, an image from which the influence of variation in the state of polarization depending on the position is removed can be obtained.

Second Embodiment

Figure 15:
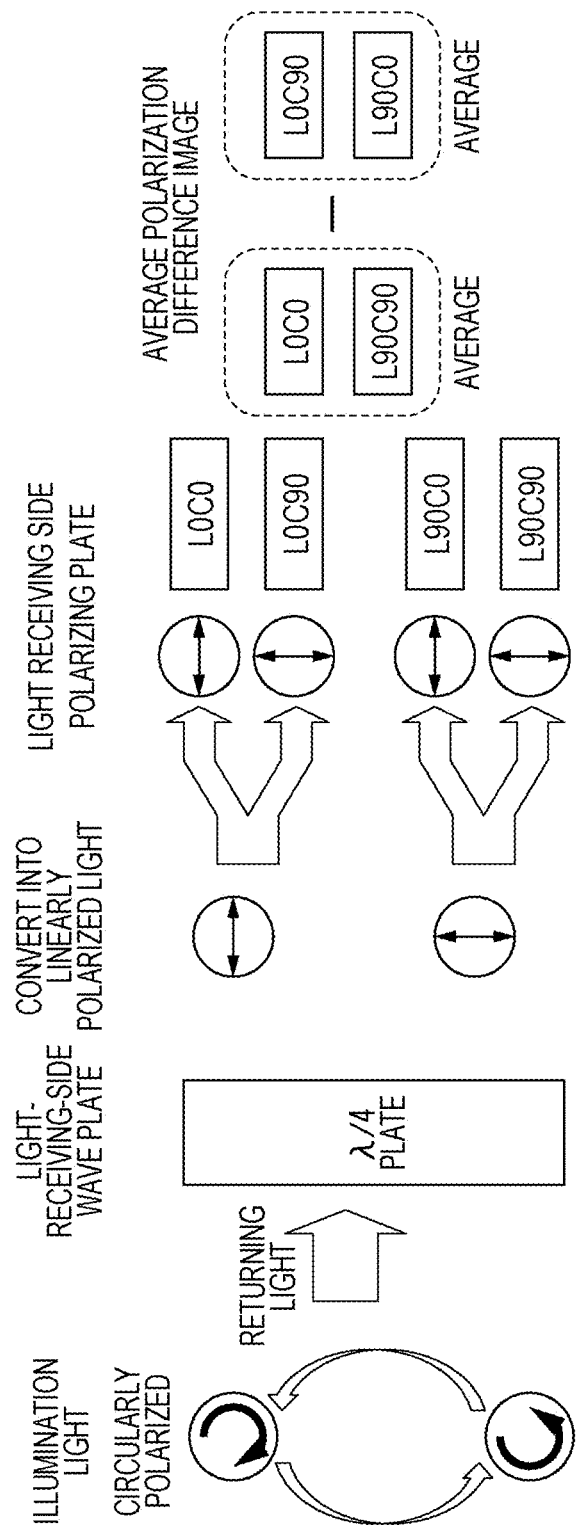
FIG. 15 illustrates a polarization imaging method according to a second embodiment of the present disclosure.

FIG. 15 illustrates a polarization imaging method according to a second embodiment of the present disclosure. In the present embodiment, circularly polarized light is used as illumination light instead of linearly polarized light. By using circularly polarized light, raindrops can be can be evenly detected irrespective of the polarization characteristics in a certain direction on the object surface.

In the present embodiment, an object is illuminated with illumination light L, which is circularly polarized light having an electric field oscillation plane that temporally alternately rotates clockwise and counterclockwise on a plane perpendicular to the travelling direction of the light. Although the direction of circular polarization is normally defined as a direction when viewed in the light travelling direction, in this embodiment, the direction of circular polarization is always defined as a direction when viewed from the camera. In this coordinate system, the direction of circular polarization of the circularly polarized light that is perpendicularly incident on a smooth flat surface does not change even when the light is reflected.

A receiving camera C receives returning light, changes the phase of the light with a $\lambda/4$ plate to convert the light into linearly polarized light, and then divides the linearly polarized light into two light components. Then, two types of polarization imaging processes are performed in parallel by using linear polarizing filters having polarization transmission axes in the directions of 0° (horizontal) and 90° (vertical) along a plane, similar to the illumination light. The $\lambda/4$ plate is an example of a phase shift element that is arranged so as to allow the returning light that returns from the object to pass therethrough, the phase shift element converting clockwise polarized light into light polarized in a first direction and counterclockwise polarized light into light polarized in a second direction that is orthogonal to the first direction. For clockwise circularly polarized illumination light L, a parallel-Nicols image L0C0 and a crossed-Nicols image L0C90 are obtained. For counterclockwise circularly polarized illumination light L, a crossed-Nicols image L90C0 and a parallel-Nicols image L90C90 are obtained.

Figure 17:
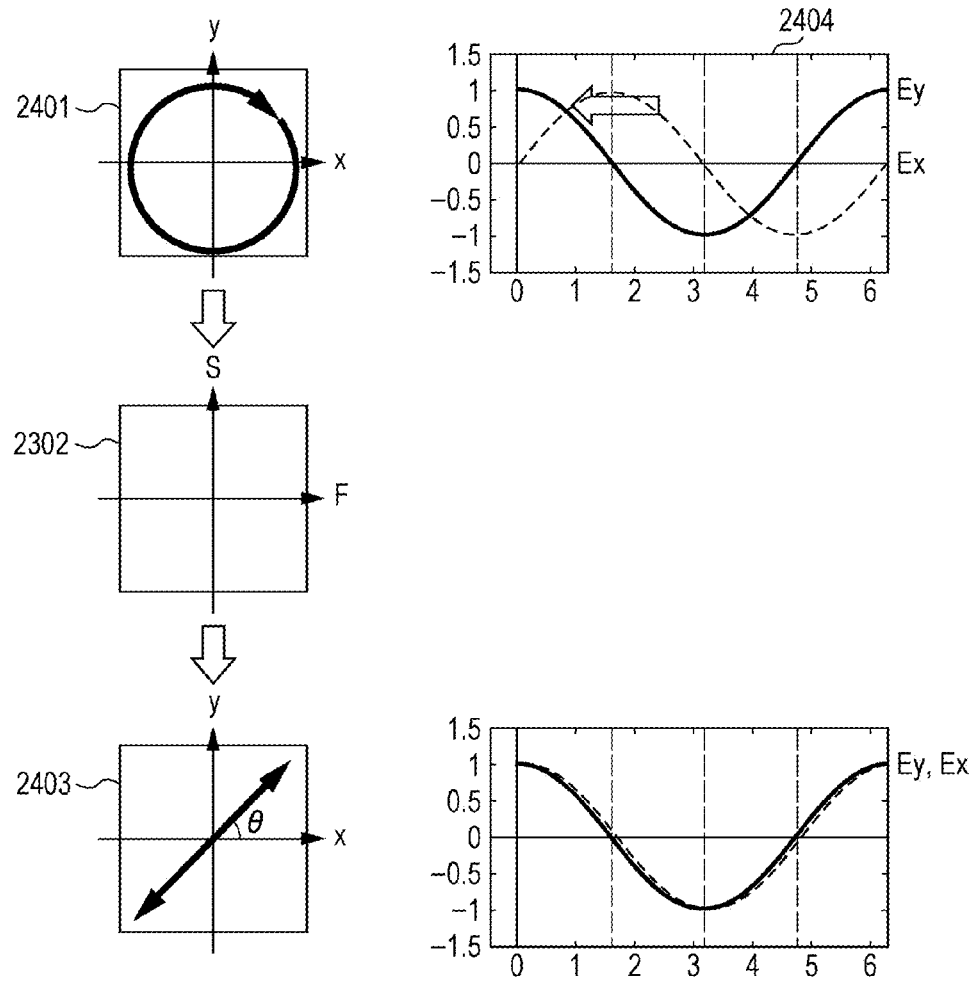
FIG. 17 illustrates the manner in which clockwise circularly polarized returning light is converted into linearly polarized light.

FIGS. 16 and 17 illustrate the manner in which the returning circularly polarized light that is reflected by the object is converted into two types of linearly polarized light having orthogonal polarization directions. FIG. 16 illustrates the manner in which counterclockwise circularly polarized light 2301 passes through the $\lambda/4$ plate as returning light, and is thereby converted into linearly polarized light 2303. In the counterclockwise circularly polarized light 2301, the phase of a Y-axis electric field component Ey is delayed by $\lambda/4$ with respect to the phase of an X-axis electric field component Ex. Accordingly, as in an orientation 2302 of the $\lambda/4$ plate, the X-axis and Y-axis are respectively set to an F-axis (fast or advanced axis) and an S-axis (slow or delayed axis), so that the phase of Ex is further advanced by $\lambda/4$ as shown by the arrow in 2304 and the phase difference between Ex and Ey is changed to $\lambda/2$, that is, $\pi$. As a result, linearly polarized light having an angle of $\theta=135°$ can be obtained as in 2303.

FIG. 17 illustrates the manner in which the clockwise circularly polarized light 2401 passes through the $\lambda/4$ plate as returning light, and is thereby converted into linearly polarized light 2403. In the clockwise circularly polarized light 2401, the phase of the Y-axis electric field component Ey is advanced by $\lambda/4$ with respect to the phase of the X-axis electric field component Ex. Accordingly, as in the orientation 2302 of the $\lambda/4$ plate, the X-axis and Y-axis are respectively set to the F-axis (fast or advanced axis) and the S-axis (slow or delayed axis), so that the phase of Ex is further advanced by $\lambda/4$ as shown by the arrow in 2404 and the phase difference between Ex and Ey is changed to 0. As a result, linearly polarized light having an angle of $\theta=45°$ can be obtained as in 2403.

Figure 18:
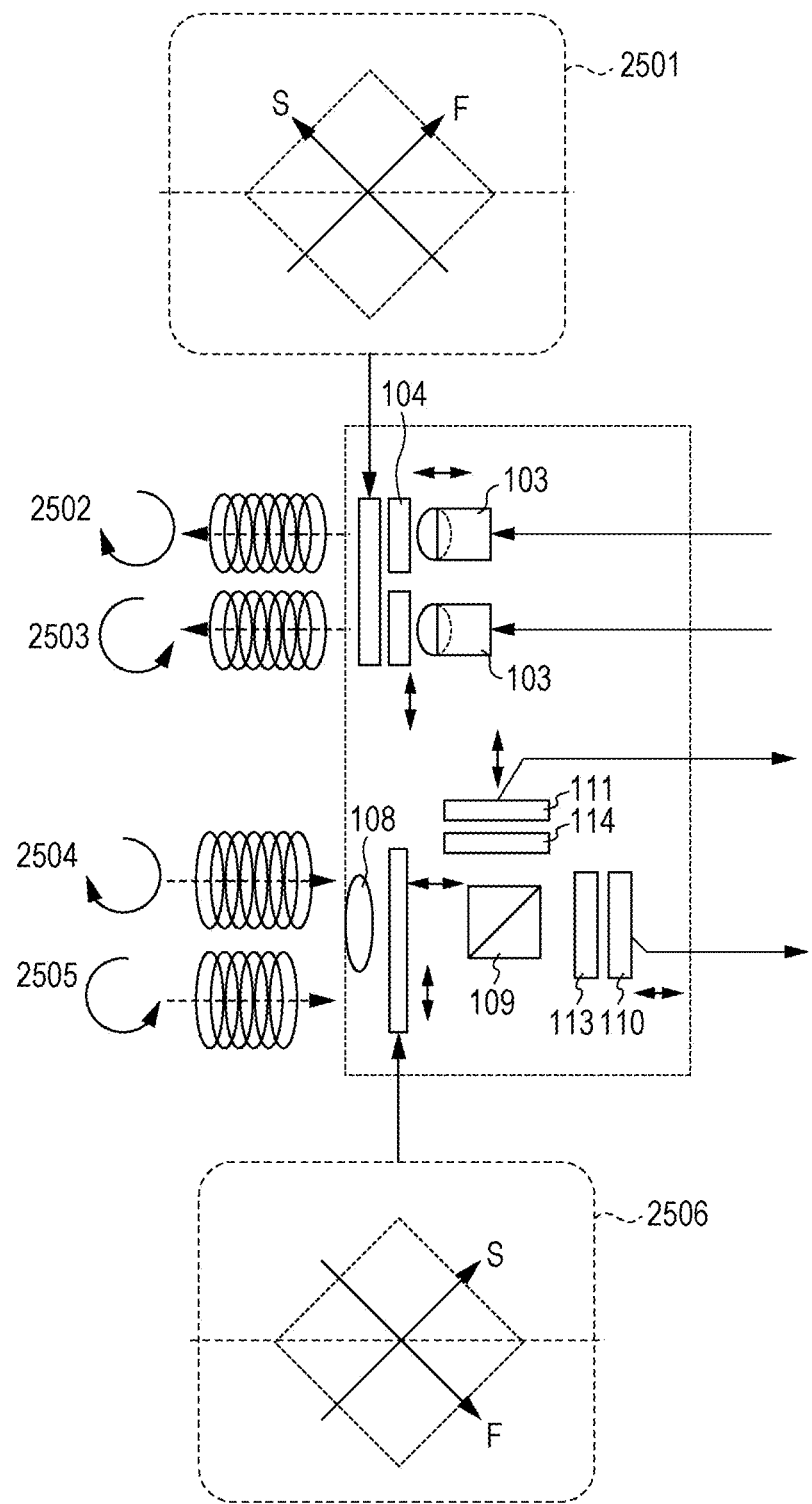
FIG. 18 illustrates the structure of a polarization imaging apparatus according to the second embodiment of the present disclosure.

FIG. 18 is a schematic diagram illustrating the structure of a part of a polarization image processing apparatus according to a second embodiment of the present disclosure. The overall structure of this apparatus is the same as that illustrated in FIG. 4. Therefore, only a portion of an imaging unit 101 which differs from that in the apparatus illustrated in FIG. 4 will be described.

The illumination unit included the apparatus illustrated in FIG. 18 includes a $\lambda/4$ plate 2501, polarizing plates 104, and light sources 103 arranged in that order from the object side. The light sources 103 are structured such that light source elements that emit linearly polarized light having a polarization plane at 0° and light source elements that emit linearly polarized light having a polarization plane at 90° are alternately arranged in a circular pattern. The number of light source elements is, for example, eight. The $\lambda/4$ plate 2501 is arranged such that optical axes, which are an F-axis (fast or advanced axis) and an S-axis (slow or delayed axis), thereof are at an angle of 45° with respect to the polarization plane of the light that is emitted from the light sources 103 and transmitted through the polarizing plates 104, so that the phase can be shifted by $\lambda/4$. Here, the array of light source elements having a polarization plane at 0° and the array of light source elements having a polarization plane at 90° are alternately selected and turned on. Accordingly, the object can be substantially spatially evenly illuminated with illumination light that temporally alternately switches between clockwise circularly polarized illumination light 2502 and counterclockwise circularly polarized illumination light 2503.

The two types of circularly polarized light are emitted toward and reflected by the object, and return to the camera side as partially polarized returning light in which the degree of polarization is reduced. In accordance with the state of circular polarization of the circularly polarized illumination light, clockwise circularly polarized light 2504 and counterclockwise circularly polarized light 2505 alternately return. The returning light passes through an objective lens 108, and is alternately converted into two types of linearly polarized light having orthogonal polarization directions by a $\lambda/4$ plate

2506. The λ/4 plate 2506 is arranged such that optical axes, which are an F-axis (fast or advanced axis) and an S-axis (slow or delayed axis), thereof are at an angle of 45° with respect to the polarizing filters at the imaging device side. Each of the two types of linearly polarized light is divided into two light components by a beam splitter 109 along optical paths. The light components pass through polarizing filters 114 and 113, and reach imaging devices 111 and 110, where polarization imaging is performed.

Third Embodiment

Figure 19:
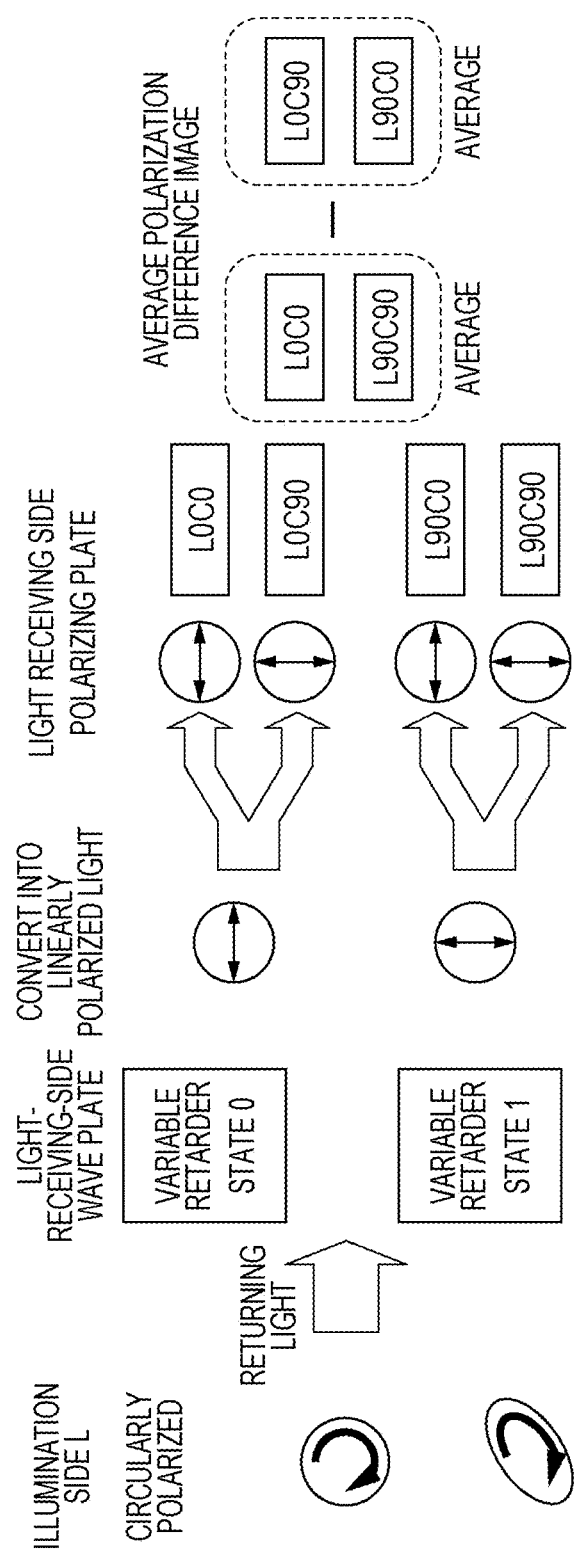
FIG. 19 illustrates a polarization imaging method according to a third embodiment of the present disclosure.

FIG. 19 illustrates an imaging method according to a third embodiment of the present disclosure. Similar to the second embodiment, in the present embodiment, circularly polarized light is used as illumination light. The third embodiment differs from the second embodiment in that only circularly polarized light having a single polarization direction is used as illumination light. Accordingly, the structure of the illumination unit can be simplified, and raindrops can be evenly detected irrespective of the polarization characteristics in a certain direction on the object surface.

An object is illuminated with illumination light L, which is circularly polarized light having an oscillation plane that rotates clockwise or counterclockwise on a plane perpendicular to the travelling direction of the light. Although the direction of circular polarization is not limited, here, it is assumed that the direction of circular polarization is clockwise when viewed from the camera.

A receiving camera C receives returning light, and converts the returning light into linearly polarized light by shifting the phase of an oscillating component of the returning light with a variable retarder (variable phase shift element). After that, the linearly polarized light is divided into two light components, and two types of polarization imaging processes are performed in parallel by using linear polarizing filters having polarization transmission axes in the directions of 0° (horizontal) and 90° (vertical) along a plane. The variable retarder is a so-called phase shifter which uses liquid crystal. By utilizing the technology of, for example, Liquid Crystal Variable Retarders (manufactured by Meadowlark Optics Inc.), the phase of the oscillating component can be changed by an amount of 0 to λ/2 by controlling the applied voltage. Therefore, the circularly polarized light can be converted into two types of linearly polarized light having orthogonal polarization directions. The variable retarder is an example of a variable phase shift element that is arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction. More specifically, in the case where the circularly polarized illumination light L is clockwise, the voltage applied to the variable retarder can be temporally controlled so that, for example, a parallel-Nicols image L0C0 and a crossed-Nicols image L0C90 are obtained when the state of the variable retarder is 0, and a crossed-Nicols image L90C0 and a parallel-Nicols image L90C90 are obtained when the state of the variable retarder is 1.

Figure 20:
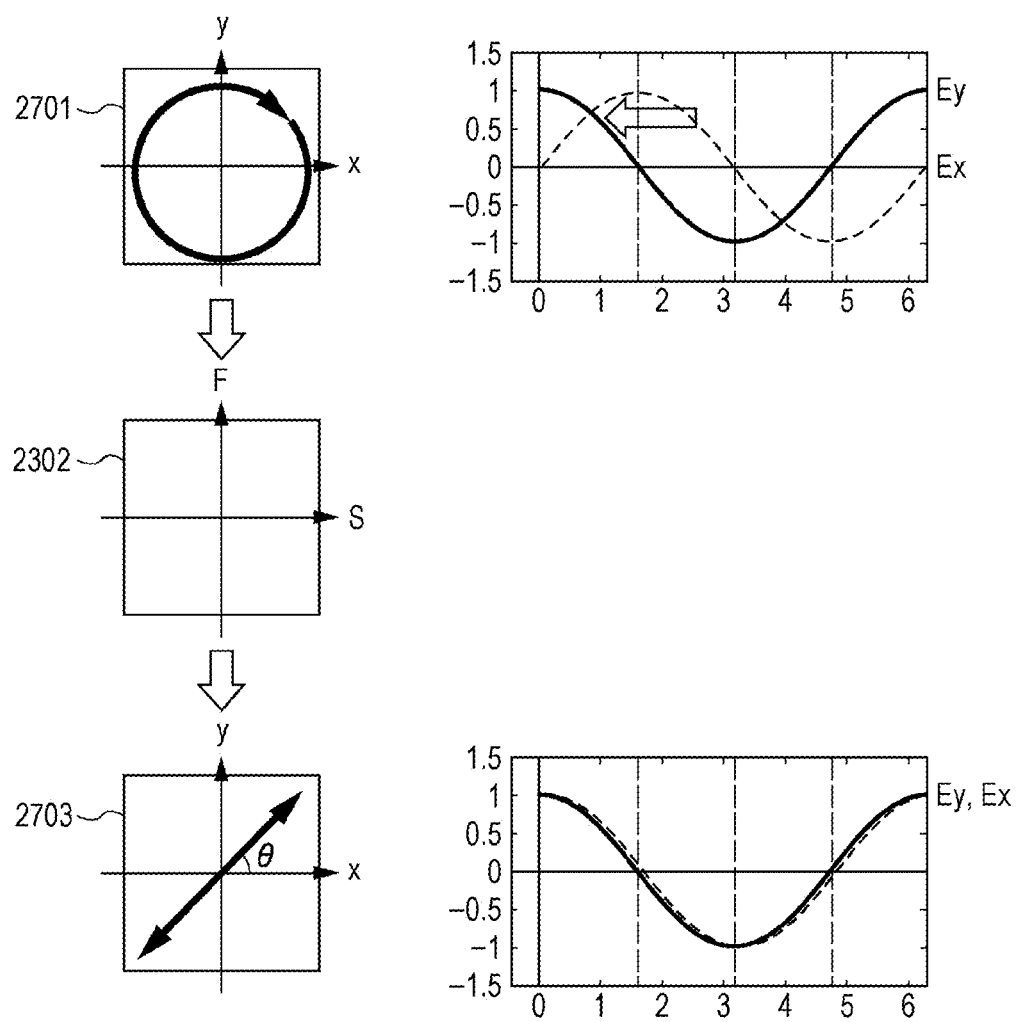
FIG. 20 illustrates the manner in which clockwise circularly polarized returning light is converted into linearly polarized light that is polarized in a direction of 45°.
Figure 21:
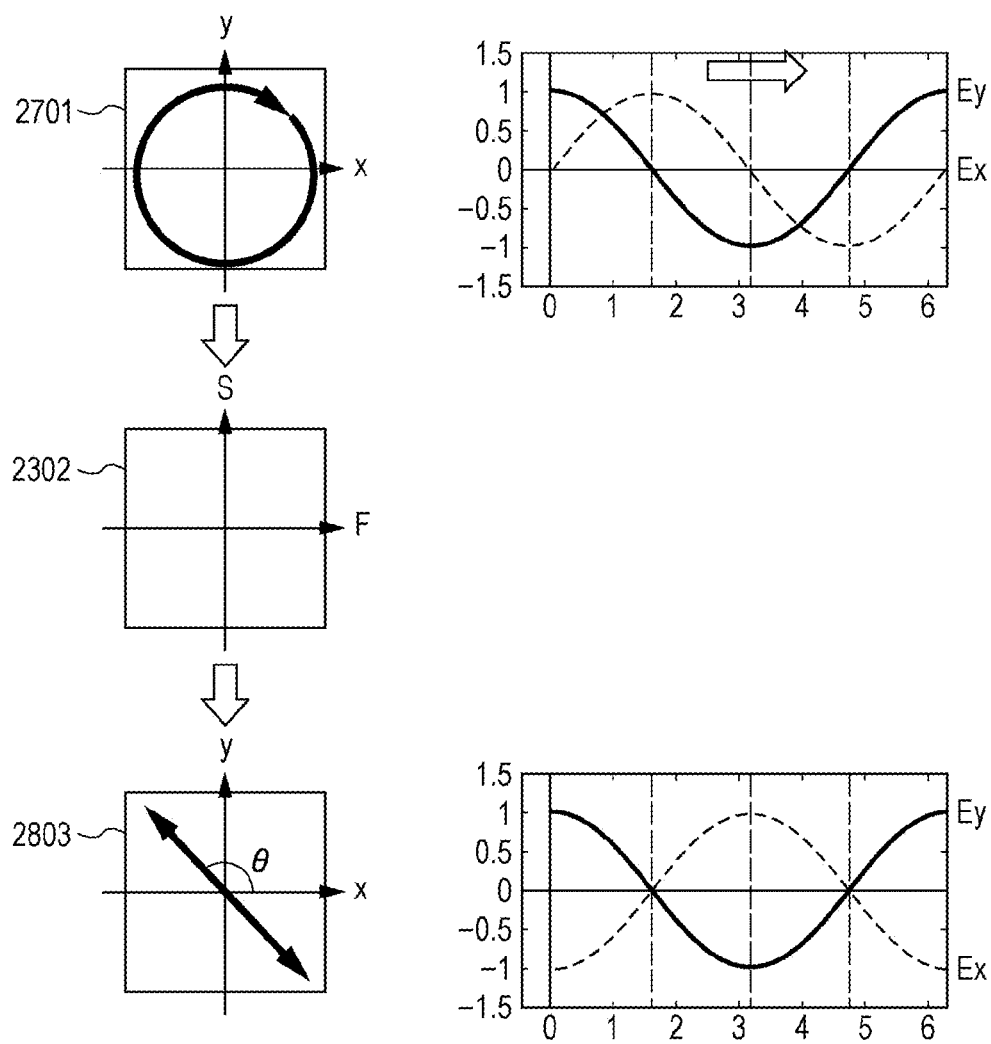
FIG. 21 illustrates the manner in which clockwise circularly polarized returning light is converted into linearly polarized light that is polarized in a direction of 135°.

FIGS. 20 and 21 illustrate the manner in which the returning light, which is the circularly polarized light, is converted into two types of linearly polarized light having orthogonal polarization directions. FIG. 20 illustrates the manner in which clockwise circularly polarized light 2701 passes through the variable retarder as the returning light while the variable retarder is set such that an X-axis is an S-axis (slow or delayed axis), a Y-axis is an F-axis (fast or advanced axis), and a phase shift is λ/4. In this case, the clockwise circularly polarized light 2701 is converted into linearly polarized light 2703 with a polarization angle of θ=45°. FIG. 21 illustrates the manner in which the clockwise circularly polarized light 2701 passes through the variable retarder while the variable retarder is set such that the X-axis is the F-axis (fast or advanced axis), the Y-axis is the S-axis (slow or delayed axis), and the phase shift is λ/4. In this case, the clockwise circularly polarized light 2701 is converted into linearly polarized light 2803 with a polarization angle of θ=135°.

Figure 22:
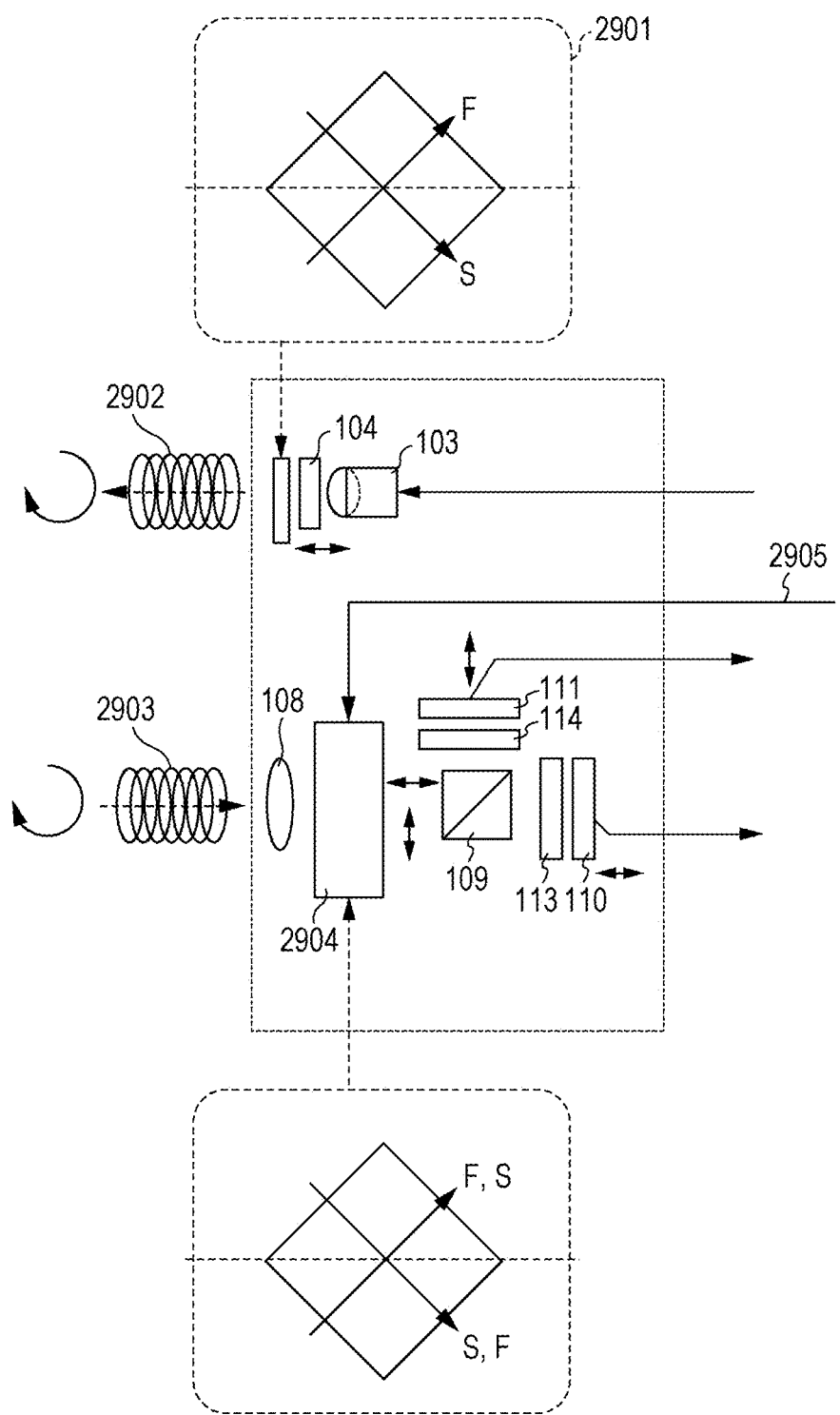
FIG. 22 illustrates the structure of a polarization imaging apparatus according to the third embodiment of the present disclosure.

FIG. 22 is a schematic diagram illustrating the structure of a polarization imaging apparatus according to the third embodiment of the present disclosure. The overall structure of this apparatus is the same as that illustrated in FIG. 4. Therefore, only a portion of an imaging unit 101 which differs from that in the apparatus illustrated in FIG. 4 will be described. The illumination unit according to the present embodiment includes a λ/4 plate 2901, a polarizing plate 104, and a light source 103 arranged in that order from the object side. As shown in FIG. 22, the λ/4 plate 2901 is arranged at an angle of 45° with respect to the direction of the polarizing plate 104, so that an object is illuminated with clockwise circularly polarized illumination light 2902. Returning light that is reflected by the object is clockwise circularly polarized light 2903 in which the degree of polarization is reduced. The clockwise circularly polarized light 2903 passes through an objective lens 108 and is incident on a variable retarder 2904 that is at an angle of 45° with respect to polarizing filter axes at the imaging side. The state of the variable retarder 2904 can be alternately switched between two states in accordance with a voltage applied through a phase control line 2905. Accordingly, the clockwise circularly polarized light 2903 is alternately converted into two types of linearly polarized light having polarization angles of 0° and 90°. Each of the two types of linearly polarized light is divided into two light components by a beam splitter 109 along optical paths. The light components pass through the polarizing filters 114 and 113, and reach imaging devices 111 and 110, where polarization imaging is performed.

In the present embodiment, it is assumed that the illumination light is clockwise circularly polarized light. However, the illumination light may instead be counterclockwise circularly polarized light. In addition, the illumination light may be elliptically polarized light instead of circularly polarized light. In such a case, the variable retarder 2904 may shift the phase of light to be incident on the beam splitter 109 by an appropriate amount instead of λ/4. Thus, effects similar to those of the present embodiment can be obtained.

In the above-described embodiment, multiple polarization imaging processes are performed by using a beam splitter. An embodiment in which no beam splitter is used will now be described.

Fourth Embodiment

Figure 23A:
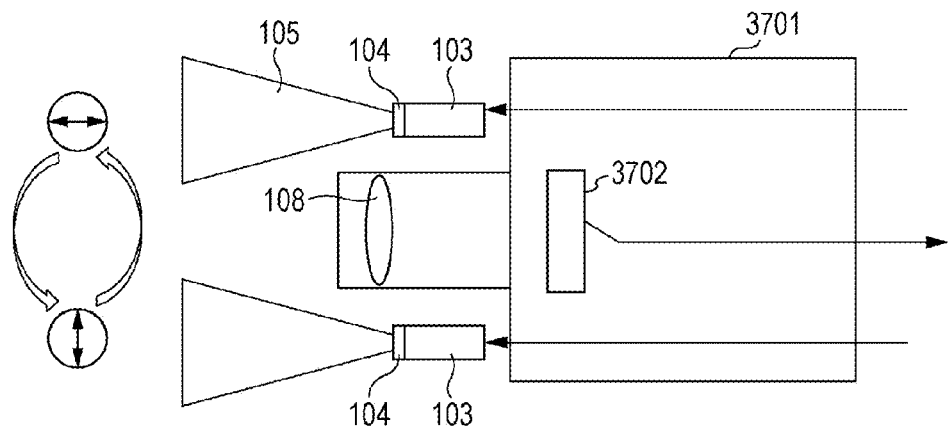
FIGS. 23A to 23C illustrate the structure of a polarization imaging apparatus according to a fourth embodiment of the present disclosure.

FIG. 23A illustrates a polarization imaging apparatus according to a fourth embodiment of the present disclosure.

In the present embodiment, a color polarization image sensor 3702 is provided as an imaging unit 101 having another structure. In the color polarization image sensor 3702, a mosaic polarizing filter having two types of transmission axes in the directions of 0° and 90° is formed on a color imaging device having four wavelength ranges of R, G, B, and IR. An illumination unit, which includes light sources 103 and polarizing filters 104, has the same structure as that of the illumination units according to the above-described embodiments.

Figure 23B:
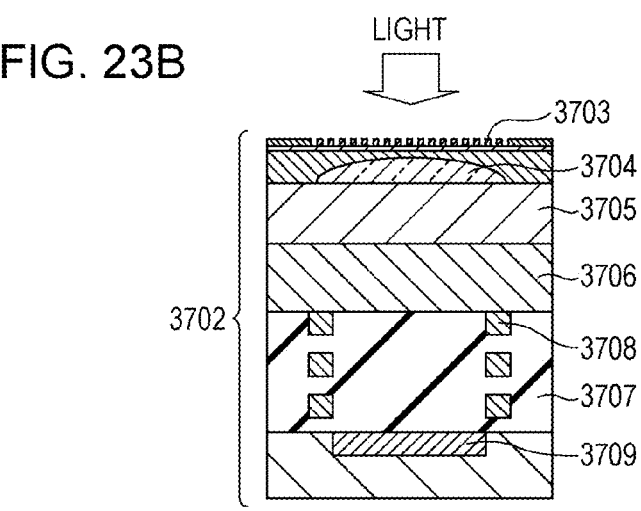

FIG. 23B illustrates the cross sectional structure of the color polarization image sensor 3702.

Incident light reaches an imaging plane through an objective lens 108. A wire grid mosaic 3703 made of a metal is provided at the top, and a microlens 3704 is provided under the wire grid mosaic 3703. The microlens 3704 has a function of efficiently collecting light at a photodiode (PD) 3709. A planarizing layer 3705 and a color filter mosaic 3706 are disposed under the microlens 3704. The color filter mosaic 3706 may be made of an organic material, a metal, or a photonic crystal. A planarizing layer 3707 and a wiring layer 3708 are provided under the color filter mosaic 3706. The wiring layer 3708 is not provided in regions where light is transmitted. Therefore, returning light that returns from the object reaches the PD 3709 without being blocked by the wires.

Figure 23C:
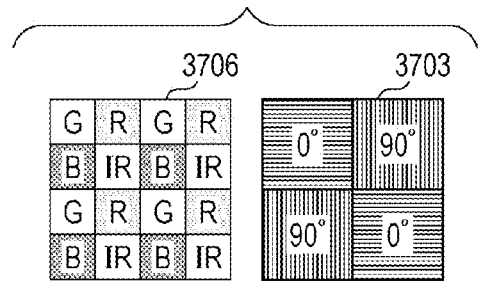

FIG. 23C is a top view of the color polarization image sensor 3702. The planar structures of the color filter mosaic 3706 and the wire grid mosaic 3703, which are arranged in the vertical direction, are illustrated next to each other. Wire grid portions having polarization transmission axes in the directions of 0° and 90° are each allocated to a region of 2×2 pixels. The 2×2 pixels include color pixels corresponding to the four wavelength ranges of R, G, B, and IR. Thus, polarization images corresponding to the four wavelength ranges can be obtained in parallel.

Also in the present embodiment, an operation similar to that performed by the imaging unit 101 illustrated in FIG. 4 can be realized. In other words, the imaging unit 101 captures a first polarization image polarized in a first direction and a second polarization image polarized in a second direction while the object is being illuminated with first illumination light, and captures a third polarization image polarized in the first direction and a fourth polarization image polarized in the second direction while the object is being illuminated with second illumination light. Thus, polarization images similar to the average parallel-Nicols image 3205 and the average crossed-Nicols image 3206 illustrated in FIG. 5 can be obtained. Thus, even when no beam splitter is provided, raindrops on the windshield can be detected by coaxial illumination using polarized light.

Thus, even when no beam splitter is used, when a polarizing plate including at least one first polarizer that transmits light polarized in the first direction and at least one second polarizer that transmits light polarized in the second direction is disposed between an imaging plane of the image sensor and the object, a plurality of polarization images having different polarization directions can be obtained at the same time.

The structure of such a polarization imaging apparatus is not limited to that in the present embodiment, and various structures may be employed. Examples of structures of the polarization imaging apparatus will now be described. Each of polarization imaging apparatuses described below is also capable of capturing polarization images similar to the average parallel-Nicols image 3205 and the average crossed-Nicols image 3206 illustrated in FIG. 5.

Modification of Fourth Embodiment

Figure 24:
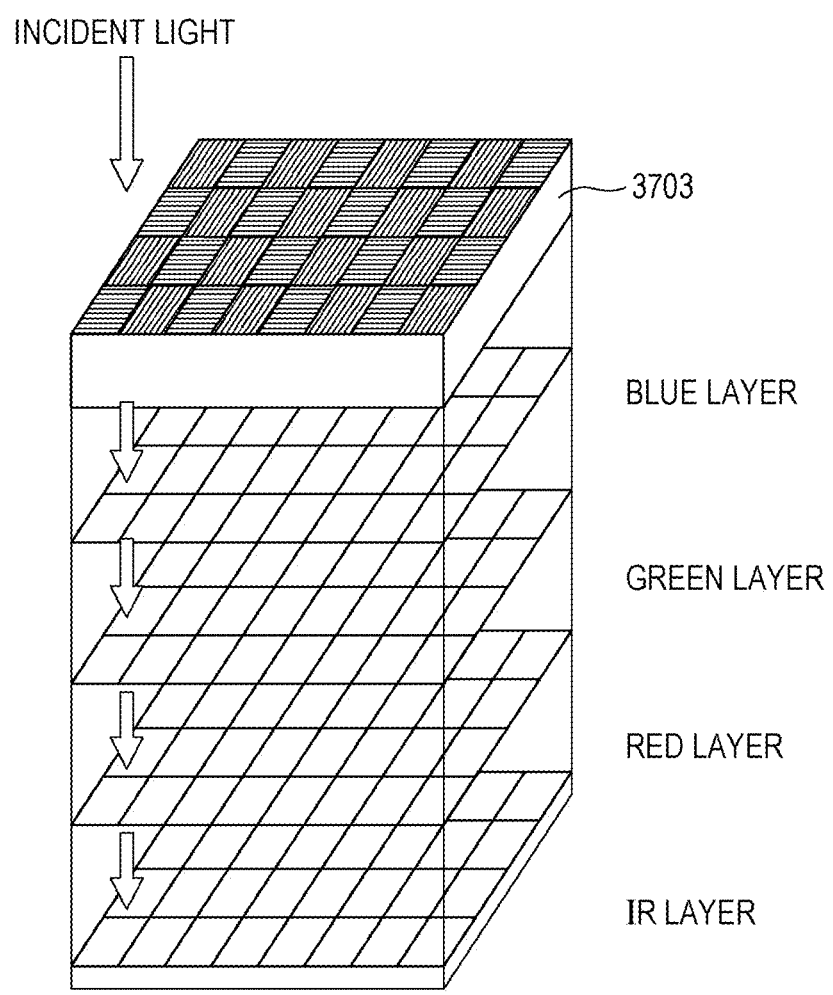
FIG. 24 illustrates a color polarization image sensor having a layered structure included in a polarization imaging apparatus according to a modification of the fourth embodiment of the present disclosure.

FIG. 24 illustrates a polarization imaging apparatus according to a modification of the fourth embodiment. In this modification, a layered color polarization image sensor having a structure different from that of the color polarization image sensor 3702 is provided. In the layered color polarization image sensor, a mosaic polarizing filter having two types of transmission axes in the directions of 0° and 90° is formed on a stack of layers corresponding to four wavelength ranges of R, G, B, and IR. This sensor may be based on, for example, a layered color image sensor described by Meenal Kulkarni and Viktor Gruev in "Integrated Spectral-Polarization Imaging Sensor with Aluminum Nanowire Polarization Filters", Oct. 8, 2012, Vo. 20, No. 21, OPTICS EXPRESS 22997. This structure is characterized in that an IR image is obtained in addition to R, G, and B images. According to this modification, a color image and polarization images can be obtained with high sensitivity and high resolution.

Fifth Embodiment

FIGS. 25A to 25D illustrate a polarization imaging apparatus according to a fifth embodiment of the present disclosure. In this embodiment, color separation into four components having wavelength ranges of R, G, B, and IR is performed by a four-output color separation prism. In a camera 3901 according to the present embodiment, an illumination unit, which includes light sources 103 and polarizing filters 104, has the same structure as that in the above-described embodiments, and description thereof is thus omitted.

Figure 25A:
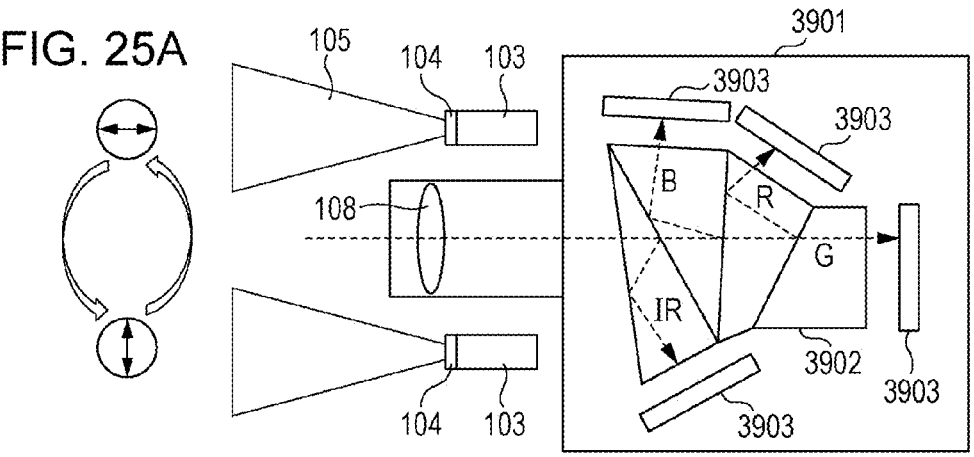
FIGS. 25A to 25D illustrate the structure of an imaging unit that serves as a polarization imaging apparatus according to a fifth embodiment of the present disclosure.

As illustrated in FIG. 25A, an imaging unit according to the present embodiment includes a four-output color separation prism 3902 which divides light incident thereon into four components of respective wavelength ranges, and four monochrome polarization imaging devices 3903 arranged on optical paths of the components into which the incident light is divided. Two types of wide-band polarization mosaic filters having transmission axes in the directions of 0° and 90° are arranged on an imaging plane of each monochrome polarization imaging device 3903.

Figure 25B:
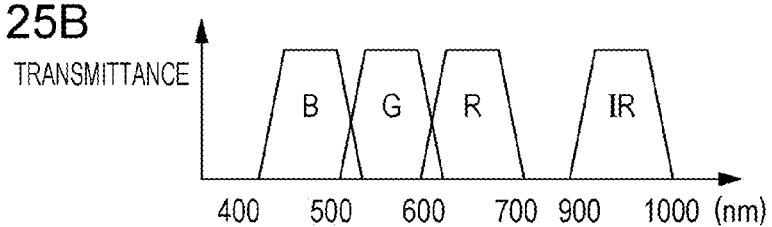

FIG. 25B illustrates the four wavelength ranges R, G, B, and IR of the four-output color separation prism. Typically, the wavelength range B is 400 to 500 nm, the wavelength range G is 500 to 600 nm, the wavelength range R is 600 to 700 nm, and the wavelength range IR is 900 to 1000 nm.

Figure 25C:
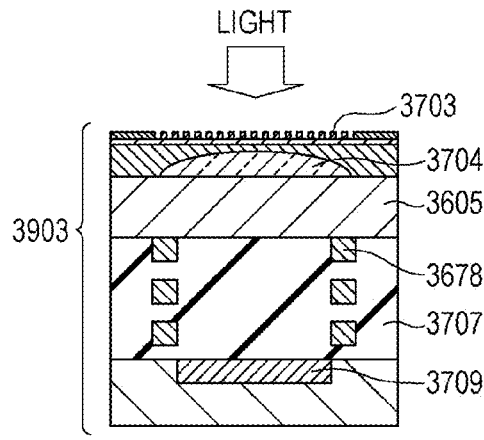

FIG. 25C illustrates an example of a cross-sectional structure of each monochrome polarization image sensor 3903. This structure is substantially the same as the cross-sectional structure illustrated in FIG. 23B, except that no color filter is provided in the present embodiment.

Figure 25D:
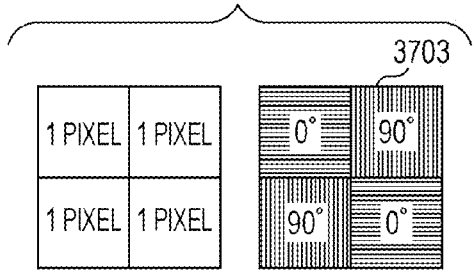

FIG. 25D illustrates the planar structure of an imaging plane. A wire grid mosaic 3703 includes wire grid portions having polarization transmission axes in the directions of 0° and 90°, and the wire grid portions are in one-to-one correspondence with pixels.

According to the present embodiment, a polarization image sensor including monochrome wire grid mosaics may be used.

Sixth Embodiment

Figure 26:
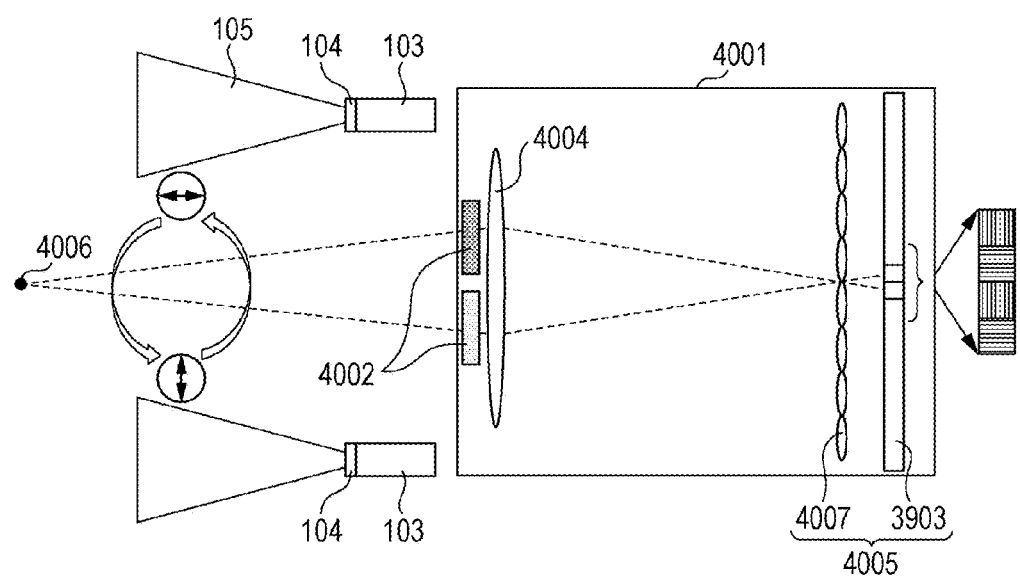
FIG. 26 illustrates the structure of an imaging unit that serves as a polarization imaging apparatus according to a sixth embodiment of the present disclosure.

FIG. 26 illustrates a polarization imaging apparatus according to a sixth embodiment of the present disclosure.

In this embodiment, color separation into four components having wavelength ranges of R, G, B, and IR is not performed by a color separation prism, but is performed by a color filter arranged on an opening of an objective lens 4004.

A camera 4001 illustrated in FIG. 26 performs color separation and polarization imaging by using a microlens-array color image sensor 4005 in which a microlens array 4007 and a monochrome polarization image sensor 3903 are integrated together. An illumination unit, which includes light sources 103 and polarizing filters 104, has the same structure as that in the above-described embodiments.

Divergent light that returns from a single point 4006 on the object passes through two regions 4002 on the objective lens 4004 and the microlens array 4007, and reaches an imaging plane of the monochrome polarization image sensor 3903. At this time, light rays that pass through the two regions 4002 on the objective lens 4004 reach different pixels. Therefore, although an image formed on the image sensor 3903 is an image of the object as a whole, the image includes two parallax images from the two regions 4002 to be precise. The two parallax images can be obtained by separating images that have passed through the two regions 4002 by performing a digital image process for selecting and integrating pixels.

Figure 27A:
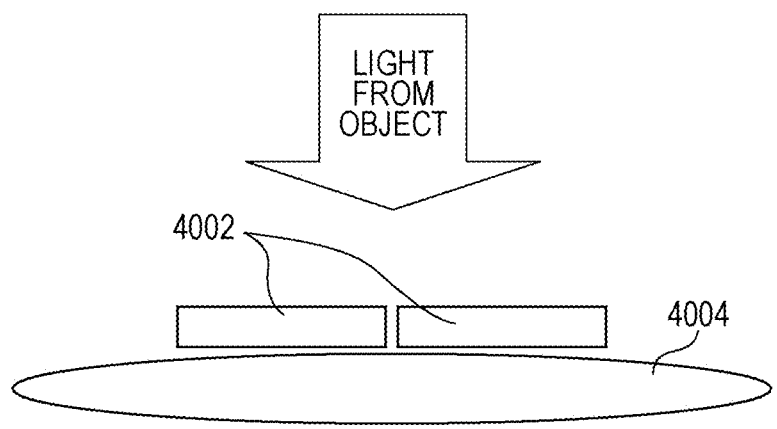
FIGS. 27A and 27B illustrate the structure of an objective lens and a color filter according to the sixth embodiment of the present disclosure.
Figure 27B:
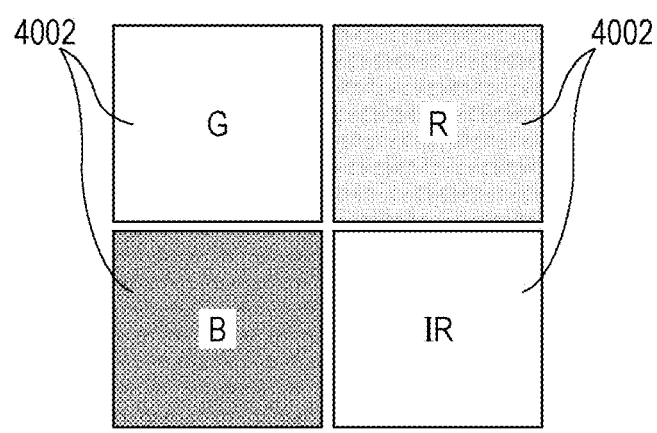

FIG. 27A illustrates the cross sectional structure of the opening of the objective lens 4004 and the color filter regions 4002. As illustrated in FIG. 27B, four different types of color filter portions R, G, B, and IR are arranged in two rows and two columns on the opening of the objective lens. The order in which the color filter regions 4002 and the objective lens 4004 are arranged from the object side may be opposite to that in FIG. 27A.

The arrangement of the color filter regions 4002 is not limited to that illustrated in FIG. 27B. The color filter regions 4002 may be made of an organic material, a photonic crystal, or any other filter material.

Figure 28:
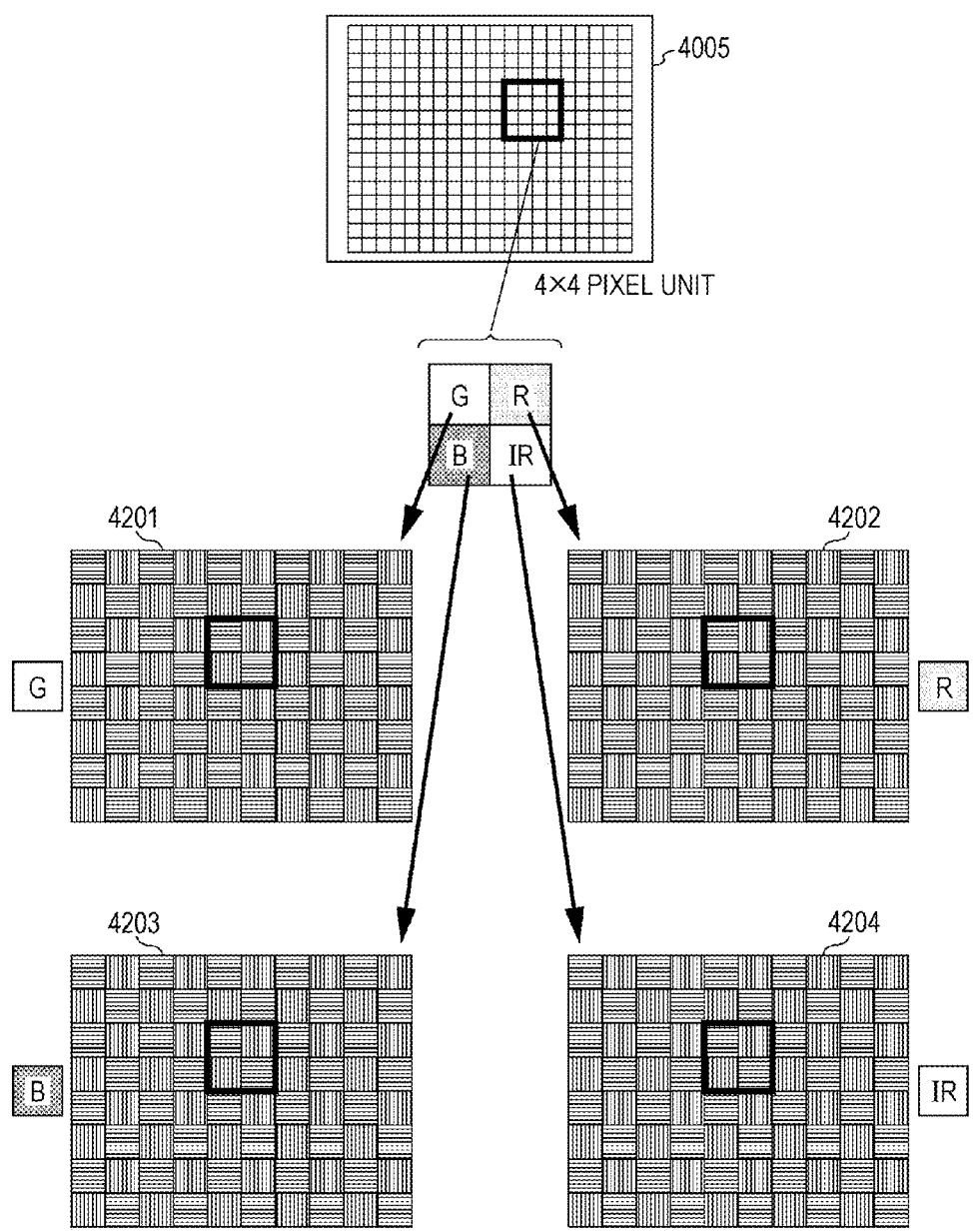
FIG. 28 illustrates a pixel selection-and-reintegration process according to the sixth embodiment of the present disclosure.

FIG. 28 illustrates a pixel selection-and-reintegration process performed to generate polarization images from the image captured by the microlens-array color image sensor 4005. A pixel unit including pixels arranged in four rows and four columns in the image formed on the sensor 4005 corresponds to light rays from four filter regions on the opening of the objective lens. Four pixels arranged in two rows and two columns in each of the upper left, upper right, lower left, and lower right regions are selected and reintegrated over the entire image. Thus, although the resolution is reduced to ¼×¼, a G polarization mosaic image 4201, an R polarization mosaic image 4202, a B polarization mosaic image 4203, and an IR polarization mosaic image 4204 can be separated from each other.

The subsequent processes are the same as those in the above-described embodiments. Also in the present embodiment, polarization images formed by polarized light having polarization transmission axes in the directions of 0° and 90° can be obtained for each of the wavelength ranges of R, G, B, and IR.

In the present embodiment, as illustrated in FIG. 28, the monochrome polarization image sensor includes two types of mosaic polarizers having transmission axes in the directions of 0° (horizontal) and 90° (vertical). Alternatively, however, four types of mosaic polarizers having transmission axes in the directions of 0°, 45°, 90°, and 135° may instead be arranged. When three or more types of polarizers are provided, the main polarization axis and the degree of polarization of any incident light in an ordinary scene can be calculated without using polarized illumination light. Accordingly, the monochrome polarization image sensor is capable of functioning as a polarization camera that operates as follows. That is, when the illumination light sources are turned on, the process for detecting raindrops on the windshield is performed by using only the pixels corresponding to the transmission axes in the directions of 0° and 90° among the pixels corresponding to the transmission axes in the directions of 0°, 45°, 90°, and 135°. When the illumination light sources are turned off, the main polarization axis and the degree of polarization of the reflected light of the external scene can be calculated by using all four types of polarizers, so that the condition of the road surface can be detected and the reflection on the curved windshield can be eliminated.

Seventh Embodiment

Figure 29:
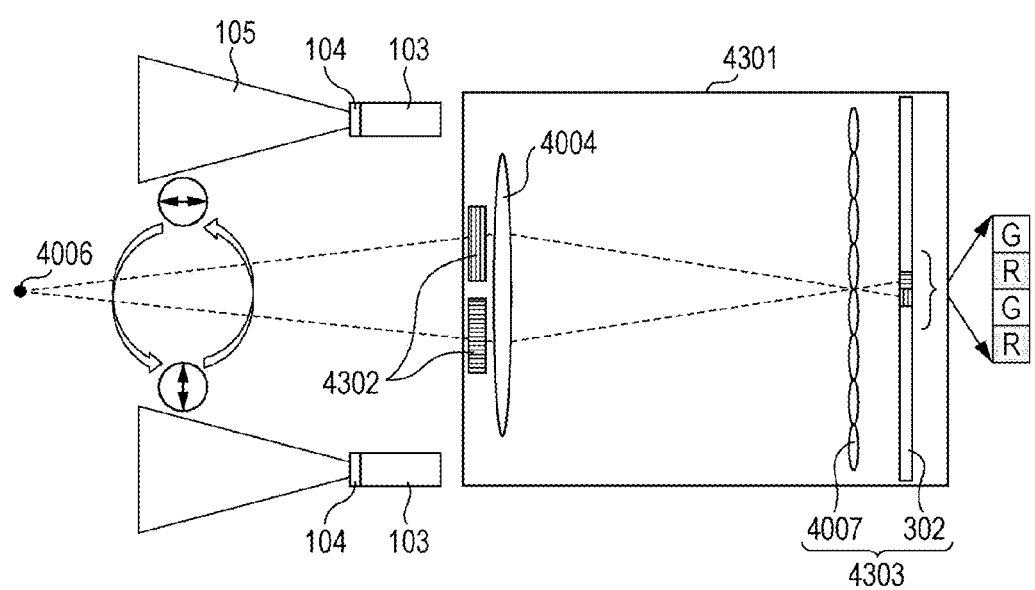
FIG. 29 illustrates the structure of an imaging unit that serves as a polarization imaging apparatus according to a seventh embodiment of the present disclosure.

FIG. 29 illustrates a polarization imaging apparatus according to a seventh embodiment of the present disclosure.

In this embodiment, light is divided into components having polarization transmission axes in the directions of 0° and 90° by using a polarization mosaic filter arranged on an opening of an objective lens 4004.

A camera 4301 illustrated in FIG. 29 performs color separation and polarization imaging by using a microlens-array color image sensor 4303 in which a microlens array 4007 and a single-plate color imaging device 302 having pixels corresponding to four wavelength ranges R, G, B, and IR are integrated together on an imaging plane. An illumination unit, which includes light sources 103 and polarizing filters 104, has the same structure as that in the other embodiments.

Divergent light that returns from a single point 4006 on the object passes through two regions 4302 of the objective lens 4004 and the microlens array 4007, and reaches the color imaging device 302 on which a color mosaic is arranged. Light rays that pass through the two regions 4302 on the objective lens 4004 reach different pixels. Therefore, although an image formed on the color imaging device 302 is an image of the object as a whole, the image includes images from the different regions in which the directions of transmission axes are 0° and 90° to be precise. Each region corresponds to 2×2 pixels in the color mosaic included in the color imaging device 302.

Figure 30A:
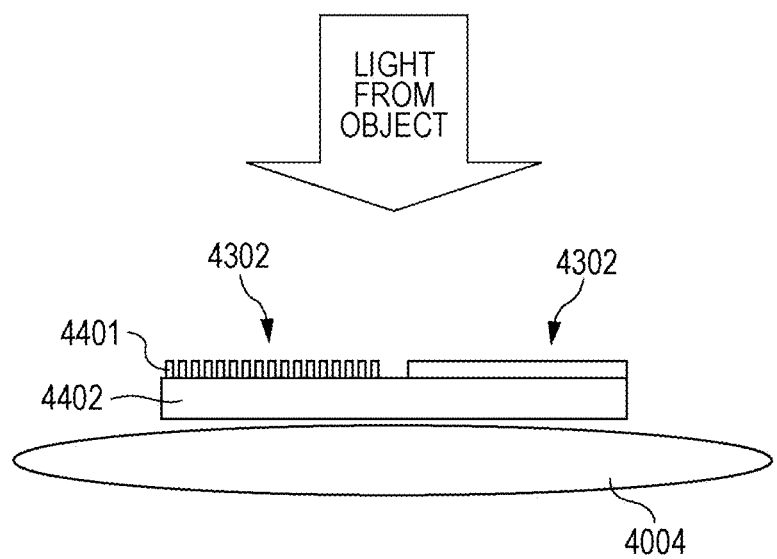
FIGS. 30A and 30B illustrate the structure of a polarizing filter provided at an opening according to the seventh embodiment of the present disclosure.

FIG. 30A illustrates the cross-sectional structure of the polarizing filter regions 4302 on the opening according to the present embodiment. In this example, a metal wire grid layer 4401 is used as the polarizing filter. The wire grid layer 4401 includes metal wires arranged on a transparent substrate 4402 at a pitch of about 100 nm, and a polarizing operation can be performed over a wide range including a visible light range and an infrared light range.

The objective lens 4004 is disposed behind the polarizing filter regions 4302. The order in which the wire grid layer 4401 and the objective lens 4004 are arranged is not limited, and the wire grid layer 4401 and the objective lens 4004 may either be arranged with or without a gap provided therebetween. The polarizing plate is not limited to a wire grid layer as long as the polarizing operation can be performed over a wide range in the visible light range, and a polymer-based polarizing plate may instead be used. The wire grid layer 4401 may be made of various types of metal materials, such as aluminum (Al). The wire grid layer 4401 is not limited to those having a single layer structure, and may instead have a multilayer structure. In such a case, a light absorbing layer may be disposed at the outermost position to suppress reflection of light. Gaps between the wire grids that are stacked may be filled with another material to increase the mechanical strength. Also, the wire grids may be coated to protect the surfaces thereof from chemical reactions.

Figure 30B:
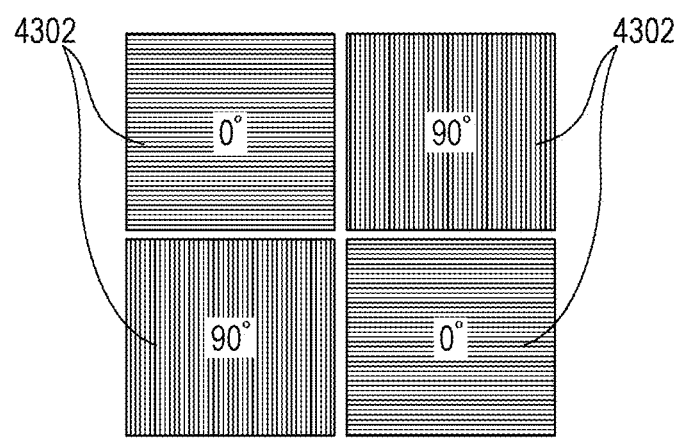

FIG. 30B illustrates the planar structure of the polarizing filter regions 4302. The polarizing filter regions 4302 include four polarizing regions having polarization transmission axes in the directions of 0° and 90° and arranged in two rows and two columns.

Figure 31:
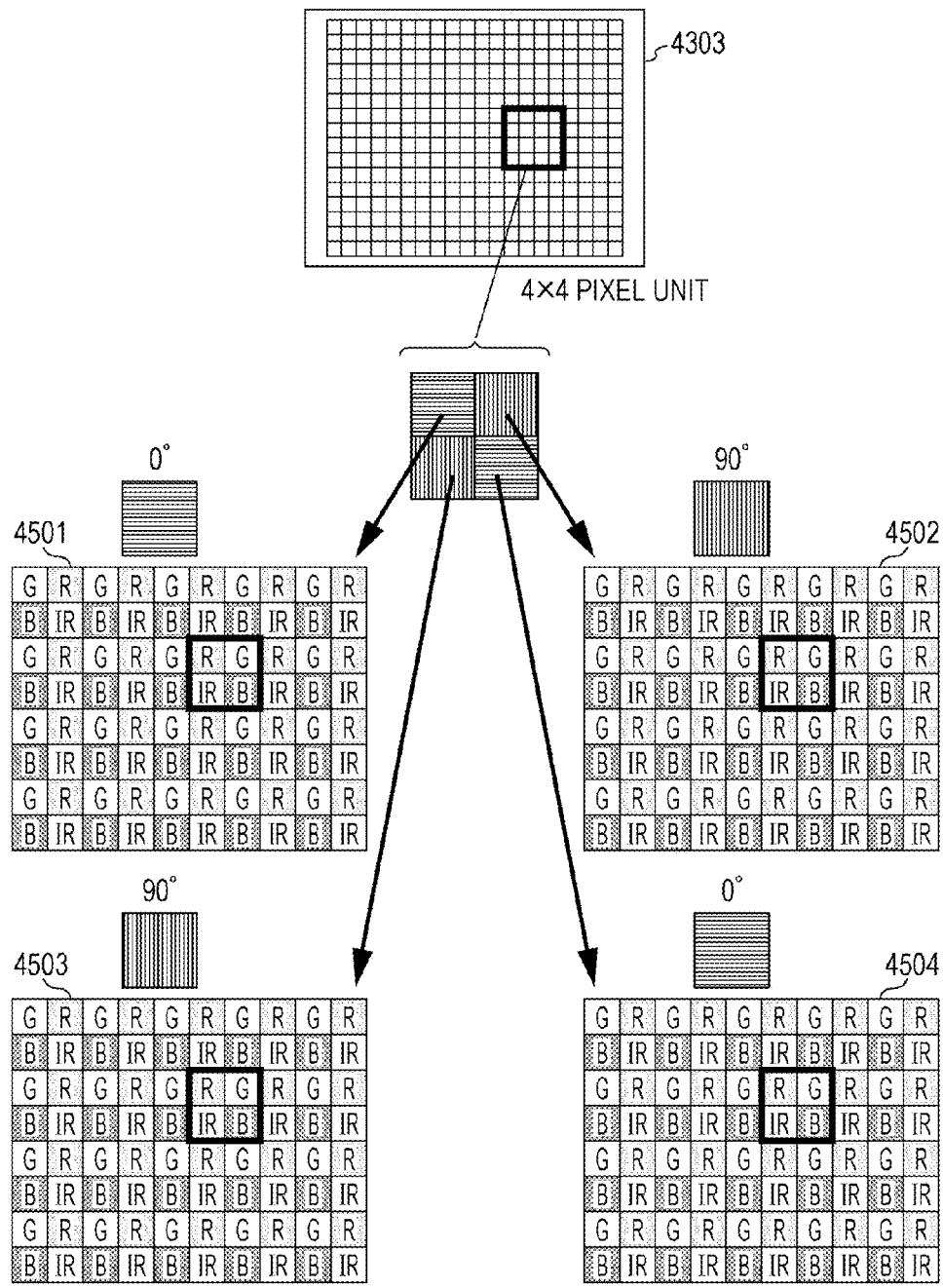
FIG. 31 illustrates a pixel selection-and-reintegration process according to the seventh embodiment of the present disclosure.

FIG. 31 illustrates a pixel selection-and-reintegration process performed to generate polarization images from the image captured by the microlens-array color image sensor 4303. A pixel unit including pixels arranged in four rows and four columns in the image formed on the sensor 4303 corresponds to light rays from the four filter regions on the opening of the objective lens. Pixels arranged in two rows and two columns in the upper left, upper right, lower left, and lower right regions are selected and reintegrated over the entire image. Thus, although the resolution is reduced to ¼×¼, R, G, B, and IR color mosaic images 4501 and 4504 that correspond to the polarization transmission axis in the direction of 0° and R, G, B, and IR color mosaic images 4502 and 4503 that correspond to the polarization transmission axis in the direction of 90° can be separated from each other. By performing a known color mosaic interpolation process, full-color and infrared polarization images corresponding to the polarization transmission axes in the directions of 0° and 90° can be obtained.

According to the present embodiment, since the polarizing plate can be arranged at the opening of the lens, the size of each polarization mosaic element can be increased compared to that in the case where the polarizing plate is disposed on the imaging device. For example, in a polarization-mosaic-type imaging device used in the fifth embodiment, the length of a portion of each metal wire that forms a polarization mosaic unit is the same as the pixel size of the imaging device, and is typically 1 to 3 μm. With such a small size, even when the pitch of the metal wires included in the wire grid is small, the wire grid length and the number of wires are limited. As a result, the optical extinction ratio of the polarizing plate is reduced to about 10:1 or less. In the present embodiment, a relatively large wire grid polarizing plate whose size is about 0.5 mm (=500 μm), which is the size of the opening of the lens, can be used, and a high optical extinction ratio of about 100:1 can be realized. This is extremely advantageous from the viewpoint of performance.

Eighth Embodiment

Figure 32:
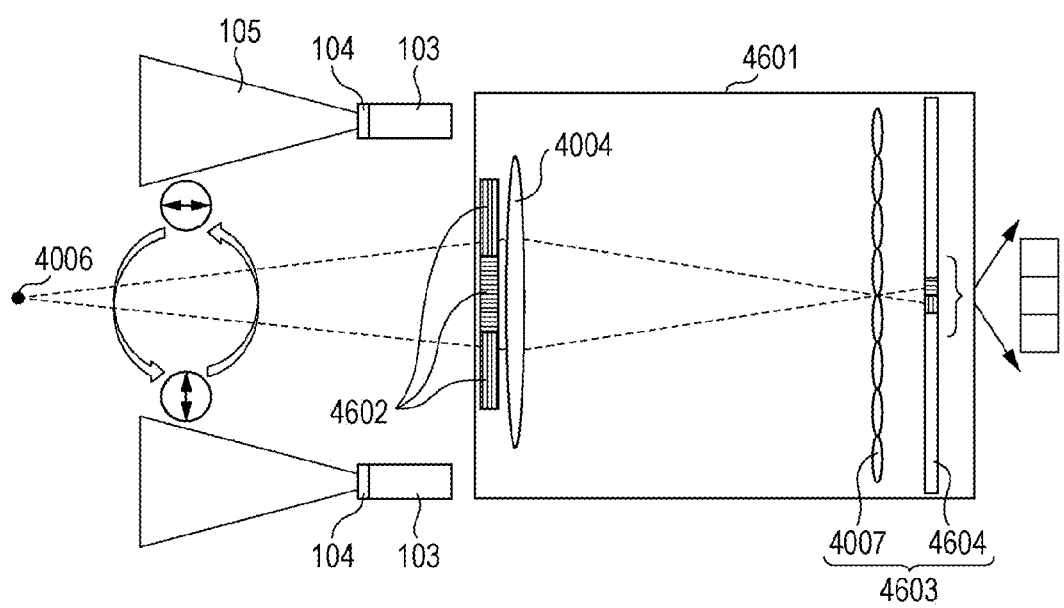
FIG. 32 illustrates the structure of an imaging unit that serves as a polarization imaging apparatus according to an eighth embodiment of the present disclosure.

FIG. 32 illustrates a polarization imaging apparatus according to an eighth embodiment of the present disclosure.

In this embodiment, separation of light into components having polarization transmission axes in the directions of 0° and 90° and separation of light into components having wavelength ranges of R, G, B, and IR are both performed by color-and-polarization composite mosaic filter regions 4602 arranged on an opening of an objective lens 4004. A camera 4601 illustrated in FIG. 32 performs color separation and polarization imaging by using a microlens-array monochrome image sensor 4603 in which a microlens array 4007 and a monochrome imaging device 4604 having a sensitivity over a wide wavelength range are integrated together on an imaging plane. An illumination unit, which includes light sources 103 and polarizing filters 104, has the same structure as that in the other embodiments, and description thereof is thus omitted.

Divergent light that returns from a single point 4006 on the object passes through eight regions 4602 on the objective lens 4004 and the microlens array 4007, and reaches the monochrome imaging device 4604. At this time, images on the respective regions on the objective lens 4004 reach different pixels. Therefore, although an image formed on the monochrome imaging device 4604 is an image of the object as a whole, the image includes the images on the eight regions on the objective lens to be precise.

Figure 33A:
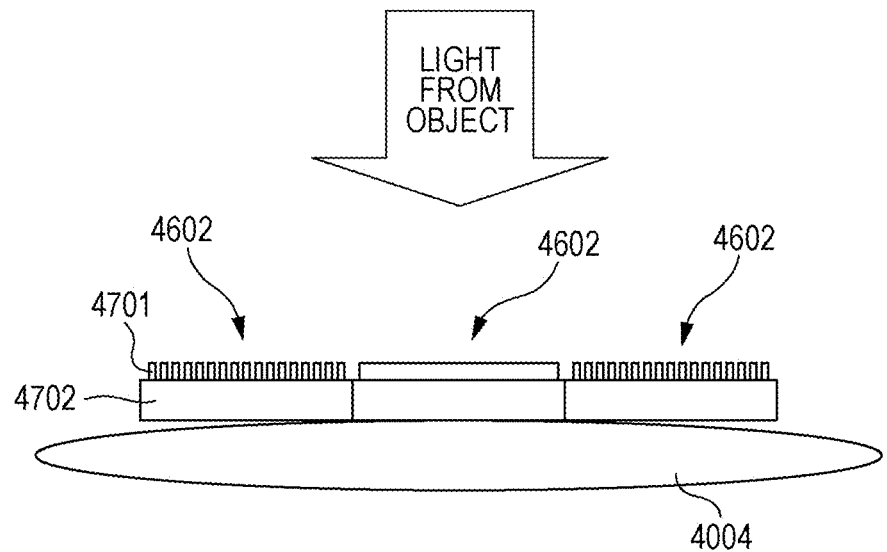
FIGS. 33A and 33B illustrate the structure of a polarizing filter provided at an opening according to the eighth embodiment of the present disclosure.

FIG. 33A illustrates the cross-sectional structure of the polarizing filter regions 4602 on the opening according to the present embodiment. In this example, a metal wire grid layer 4701 is used as the polarizing filter. The wire grid layer 4701 includes metal wires arranged on a color filter layer 4702 at a pitch of about 100 nm, and a polarizing operation can be performed over a wide range including a visible light range and an infrared light range. The objective lens 4004 is disposed under the color filter layer 4702.

Figure 33B:
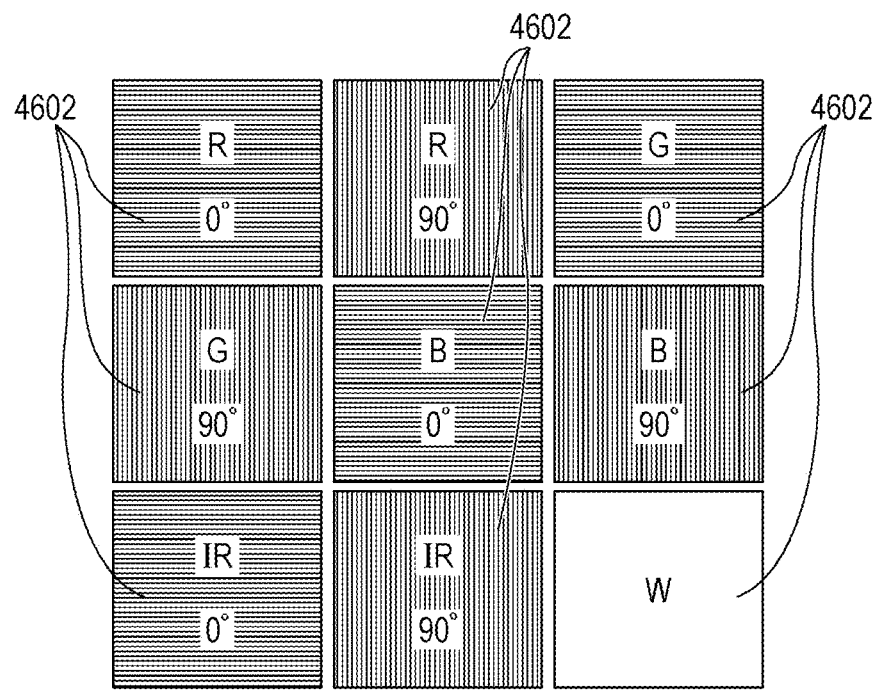

FIG. 33B illustrates the planar structure of the polarizing filter regions 4602. The polarizing filter regions 4602 include nine regions having polarization transmission axes in the directions of 0° and 90° and wavelength transmission ranges of R, G, B, and IR, the nine regions being arranged in three rows and three columns. Among the nine regions, one region that is not used may be a W region in which no color filter or polarizing filter is arranged.

Figure 34:
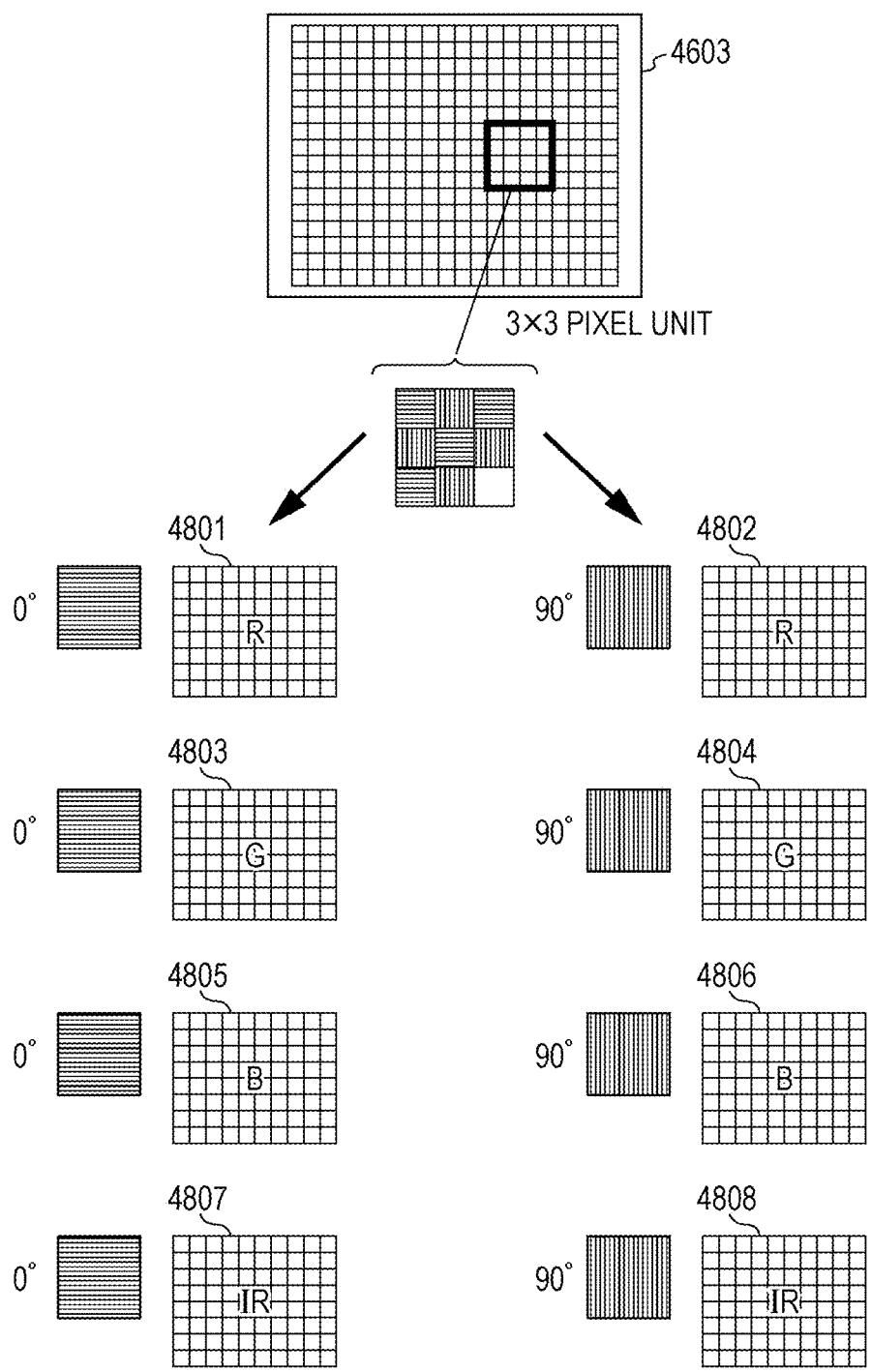
FIG. 34 illustrates a pixel selection-and-reintegration process according to the eighth embodiment of the present disclosure.

FIG. 34 illustrates a pixel selection-and-reintegration process performed to generate polarization images from the image captured by the microlens-array monochrome image sensor 4603. A pixel unit including pixels arranged in three rows and three columns in the image formed on the sensor 4603 corresponds to light rays from the nine regions on the opening of the objective lens. The pixels arranged in three rows and three columns are selected and reintegrated over the entire image. Thus, although the resolution is reduced to ⅓×⅓, R, G, B, and IR color mosaic images 4801, 4804, 4805, and 4807 that correspond to the polarization transmission axis in the direction of 0° and R, G, B, and IR color mosaic images 4802, 4804, 4806, and 4808 that correspond to the polarization transmission axis in the direction of 90° can be separated from each other. Although not illustrated, the image in the W region is also separated in a similar manner. Thus, full-color and infrared polarization images corresponding to the polarization transmission axes in the directions of 0° and 90° can be obtained.

The present embodiment is advantageous in that the wire length of the wire grid polarizing plate can be increased so that the optical extinction ratio can be increased, and the reduction in resolution is as small as ⅓×⅓.

Ninth Embodiment

Figure 35A:
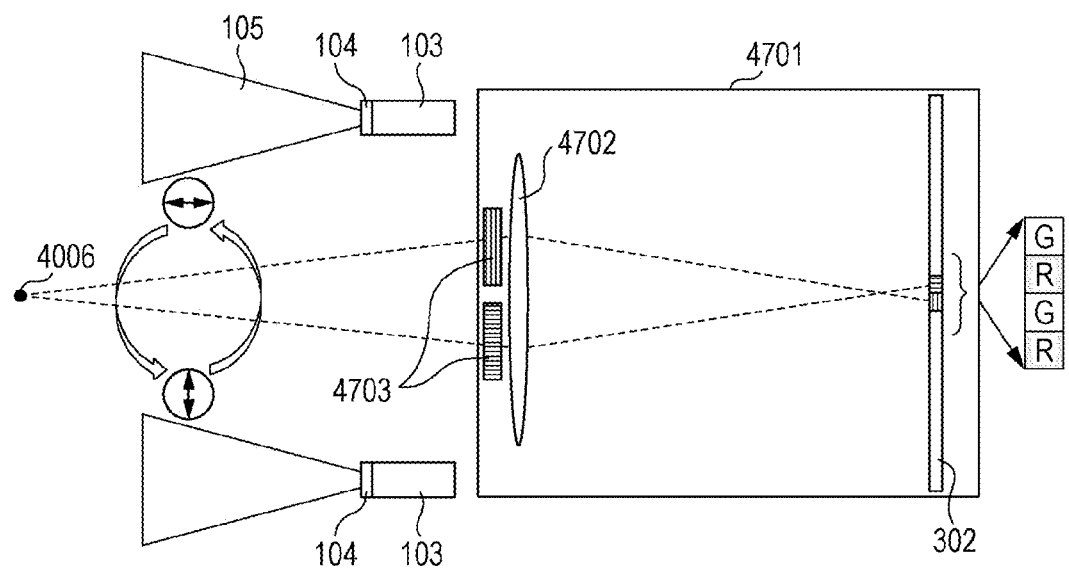
FIGS. 35A and 35B illustrate the structure of an imaging unit that serves as a polarization imaging apparatus according to a ninth embodiment of the present disclosure.

FIG. 35A illustrates a polarization imaging apparatus according to a ninth embodiment of the present disclosure.

In this embodiment, light is divided into components having polarization transmission axes in the directions of 0° and 90° by using a polarization mosaic filter arranged on openings of a plurality of objective lenses 4602. A multiple-lens color camera 4701 includes a color imaging device 302 including pixels corresponding to four wavelength ranges R, G, B, and IR on an imaging plane. An illumination unit, which includes light sources 103 and polarizing filters 104, has the same structure as that in the other embodiments.

Divergent light that returns from a single point 4006 on the object passes through polarizing filter regions 4703 provided on four objective lenses 4702 arranged in two rows and two columns, and reaches the color imaging device 302 on which a color mosaic is arranged. Images in the respective regions of the objective lenses are formed on the imaging plane as different images.

Figure 35B:
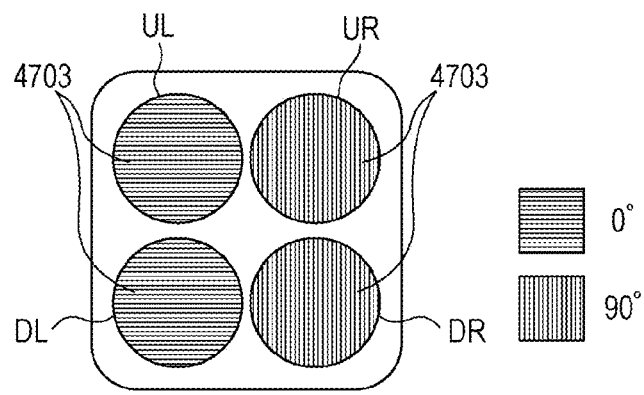

FIG. 35B illustrates polarization axes of the polarizing filter regions 4703 corresponding to the openings (UL), (UR), (DL), and (DR) of the four objective lenses. The openings (UL) and (UL) correspond to the polarization axis in the direction of 0°, and the openings (UL) and (UL) correspond to the polarization axis in the direction of 90°.

Figure 36:
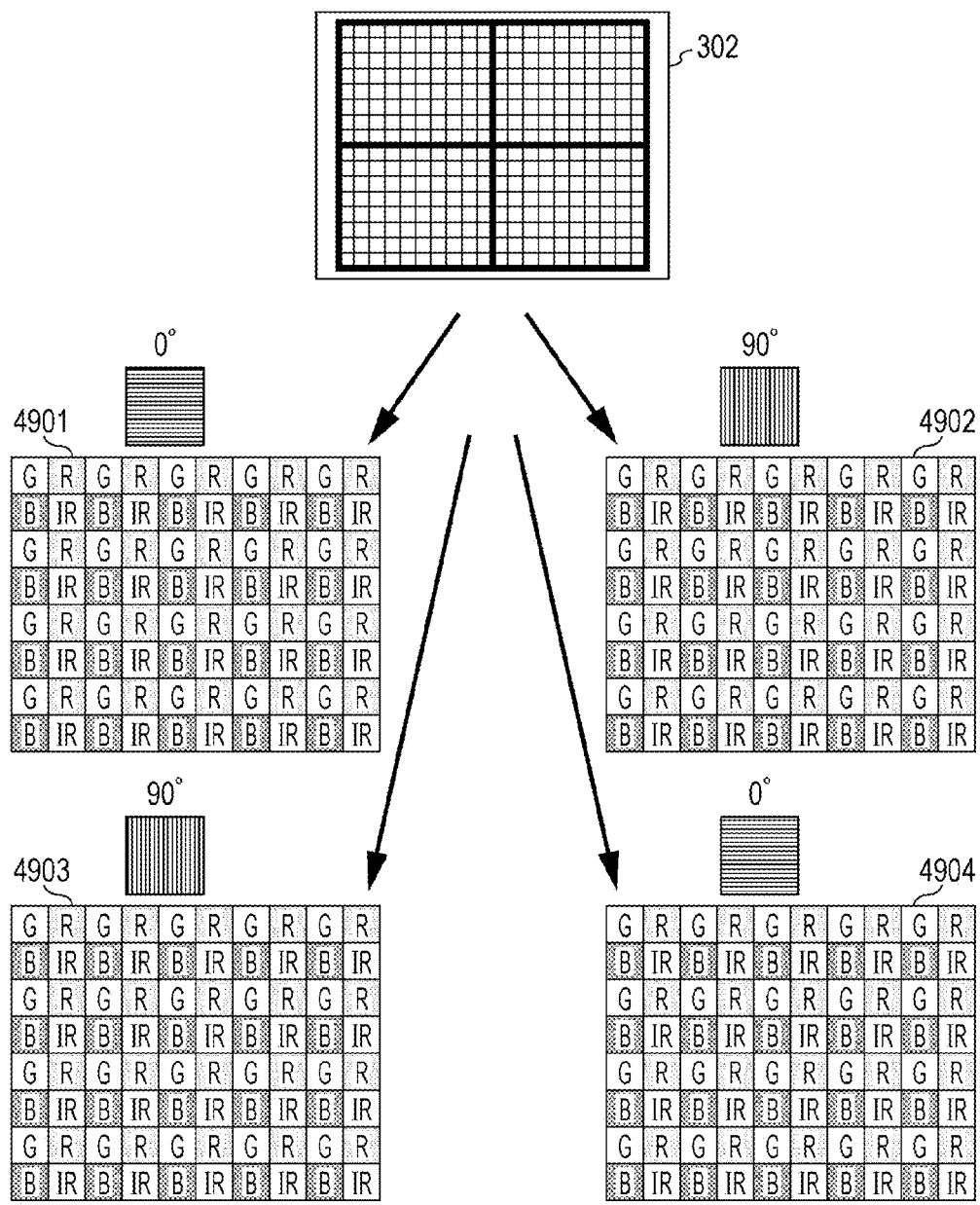
FIG. 36 illustrates a pixel selection process according to the ninth embodiment of the present disclosure.

FIG. 36 illustrates a pixel selection-and-reintegration process performed to generate polarization images from the image captured by the multiple-lens color camera 4701. The images that have passed through four regions on the openings of the four objective lenses are arranged next to each other in upper left, upper right, lower left, and lower right regions on the color imaging device 302. When the captured images are separated from each other, although the resolution is reduced to ¼×¼, R, G, B, and IR color mosaic images 4901 and 4904 that correspond to the polarization transmission axis in the direction of 0° and R, G, B, and IR color mosaic images 4902 and 4903 that correspond to the polarization transmission axis in the direction of 90° can be separated from each other. By performing a known color mosaic interpolation process, full-color and infrared polarization images corresponding to the polarization transmission axes in the directions of 0° and 90° can be obtained.

According to the present embodiment, since the polarizing plate is arranged on the openings of the lenses, the size of each polarization mosaic element can be increased compared to the case where the polarizing plate is disposed on the imaging device, and the optical extinction ratio can be increased accordingly.

Tenth Embodiment

Figure 37:
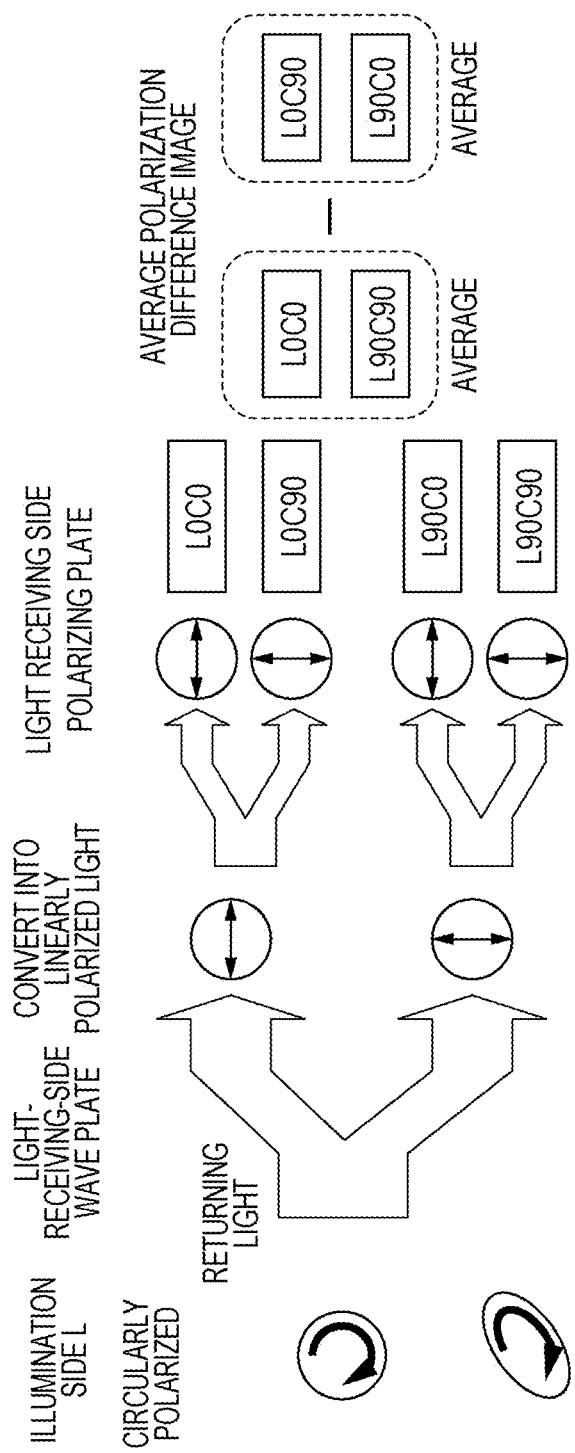
FIG. 37 illustrates a polarization imaging method according to a tenth embodiment of the present disclosure.

FIG. 37 illustrates the principle of a tenth embodiment of the present disclosure. According to the present embodiment, image processing similar to that in the case where two types of linearly polarized light are alternately emitted can be performed by using circularly polarized light having an oscillation plane that rotates in a certain direction as illumination light. In addition, the structure of the illumination unit can be simplified, and image processing can be performed in real time within a single frame by simultaneously capturing four polarization images in different states.

In the present embodiment, illumination light L emitted toward the object is circularly polarized light having an oscillation plane that rotates on a plane perpendicular to the travelling direction of the light. Although the rotational direction is not limited, here, it is assumed that the rotational direction is clockwise when viewed from the camera side. A camera C at the light receiving side divides returning light into two types of linearly polarized light that are polarized in the directions of 0° and 90° by changing the phases of the oscillation components of the returning light in two ways. Then, the camera C performs two types of polarization imaging processes for each type of light by using linear polarizing filters having transmission planes in the directions of 0° and 90°.

Here, 0° and 90° are angles determined when a camera coordinate system is appropriately set, and do not necessarily match the horizontal and vertical directions with respect to the ground or the vehicle. The horizontal and vertical directions of the imaging device of the camera are also not limited to 0° and 90°, respectively. When the camera coordinate system is set at a certain angle θ with respect to the imaging device of the camera, the angles 0° and 90° are determined in that coordinate system. This also applies to other embodiments.

The circularly polarized light can be regarded as light obtained by combining two types of linearly polarized light that are polarized in the directions of 0° and 90° and whose phases are shifted from each other by λ/4. Since it can be assumed that the object is illuminated with the two types of linearly polarized light having phases that are shifted from each other, effects similar those in the case where the two types of linearly polarized light are temporally alternately emitted can be obtained. In the description of the principle of the present disclosure, it is assumed that the returning light that is reflected by a medium when the medium is illuminated with linearly polarized light is converted into linearly polarized light and non-polarized light (random light) and is not converted into circularly polarized light. This means it is assumed that no phase modulation occurs when the polarized illumination light is reflected by the medium of the object. Therefore, in the case where the illumination light is circularly polarized light, the returning light includes two types of linearly polarized light that are polarized in the directions of 0° and 90° and whose phases remain shifted from each other by λ/4. Therefore, by dividing the returning light and shifting the phase thereof, the two types of linearly polarized light polarized in the directions of 0° and 90° included in the circularly polarized light can be simultaneously extracted. Accordingly, by observing the two types of linearly polarized light polarized in the directions of 0° and 90°, the four types of polarization images according to the present disclosure can be obtained simultaneously. More specifically, in the case where the direction of polarization of the circularly polarized illumination light L is clockwise, light L0 corresponding to the polarization direction of 0° can be obtained by dividing the returning light and shifting the phase thereof, and the parallel-Nicols image L0C0 and the crossed-Nicols image L0C90 can be obtained from the light L0. At the same time, light L90 polarized in the direction of 90° can also be obtained by dividing the returning light and shifting the phase thereof, and the crossed-Nicols image L90C0 and the parallel-Nicols image L90C90 can be obtained from the light L90. The average polarization difference image is generated from the four images that are obtained simultaneously, and is subjected to image processing. As a result, emission of the illumination light and generation of the image can be simultaneously performed within a time for a single frame.

Figure 38A:
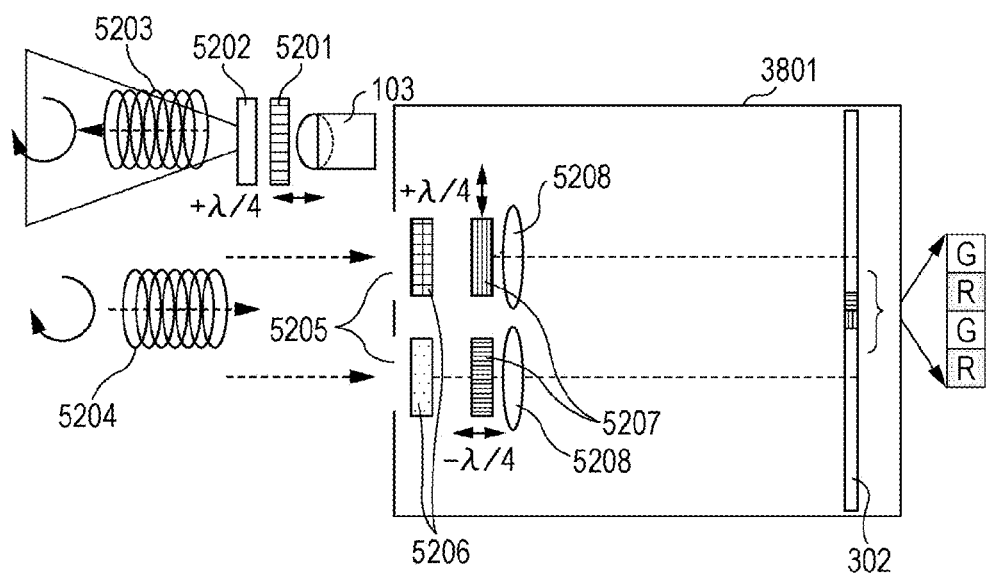
FIGS. 38A and 38B illustrate the structure of an imaging unit that serves as a polarization imaging apparatus according to the tenth embodiment of the present disclosure.

FIG. 38A is a schematic diagram illustrating the structure of a polarization imaging apparatus according to a tenth embodiment based on the above-described principle. A multiple-lens color camera 3801, which includes a circularly-polarized-light illumination unit that is substantially coaxial with an imaging system, is illustrated as an on-board camera having another structure. In the multiple-lens color camera 3801, light is caused to pass through λ/4 plates, which are phase modulators, and polarizing plates arranged on openings of a plurality of objective lenses, and a color imaging device 302 including pixels corresponding to four wavelength ranges R, G, B, and IR is disposed on an imaging plane.

The circularly-polarized-light illumination unit is positioned such that the optical axis thereof substantially coincides with an imaging axis of the imaging camera, and includes an optical element including a light source 103, a polarizing plate 5201, and a λ/4 plate 5202. The illumination light source emits circularly polarized illumination light 5203. Returning light 5204 that has been reflected by the object passes through four openings 5205, four λ/4 plates 5206, four polarizing plates 5207, and four objective lenses 5208 (only two of each component are shown in FIG. 38A), and form four images on the single-plate color imaging device 302. The single-plate color imaging device 302 may include, for example, a Bayer mosaic color filter having four wavelength ranges of R, G, B, and IR. Only two mosaic elements (G and R) are illustrated in FIG. 38A.

Figure 38B:
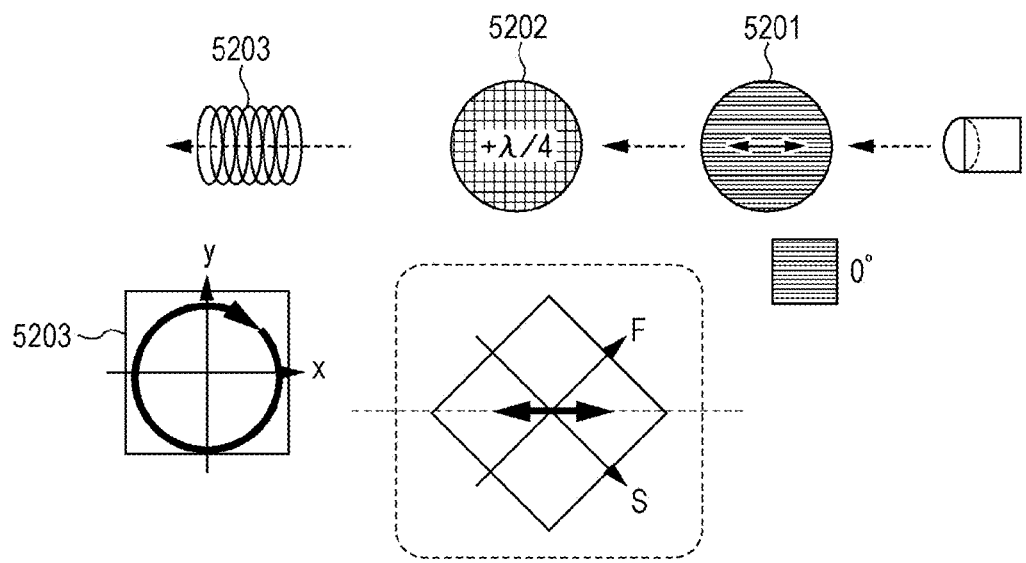

FIG. 38B illustrates the details of the process in which the circularly polarized light is generated by the illumination unit. In the illumination unit, the λ/4 plate 5202, the polarizing plate 5201, and the light source 103 are arranged in that order from the object side. The λ/4 plate 5202 is arranged at an angle of 45° with respect to the direction of the polarizing plate 5201, which transmits light having an oscillation plane in the axial direction of 0°, and X and Y axes are set to S-axis (slow axis) and F-axis (fast axis), respectively. Accordingly, the object is illuminated with clockwise circularly polarized illumination light in the camera coordinate system X-Y. This is defined as a phase modulation of $+\lambda/4$ on the linearly polarized light polarized in the direction of 0°, and "$+\lambda/4$" on the $\lambda/4$ plate 5202 denotes this phase modulation.

The $\lambda/4$ plates 5206, the polarizing plates 5207, and the objective lenses 5208 are arranged in that order from the object side in the openings 5205 of the multiple-lens camera illustrated in FIG. 38A. These components overlap each other on the optical axes. The order in which the objective lenses 5208 and the optical elements 5206 and 5207 are arranged may be opposite to the above-mentioned order. However, the order in which the $\lambda/4$ plates 5206 and the polarizing plates 5207 are arranged is fixed.

Figure 39A:
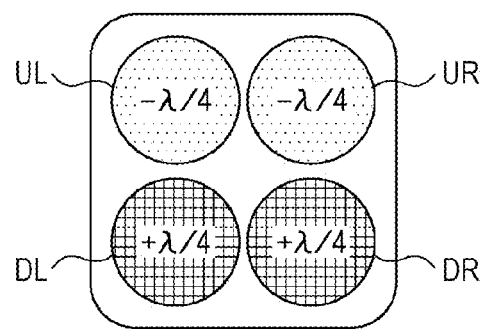
FIGS. 39A and 39B illustrate the structure of the imaging unit that serves as the polarization imaging apparatus according to the tenth embodiment of the present disclosure.

FIG. 39A illustrates the planar arrangement of the four optical elements arranged in the openings 5205. When viewed in a direction toward the camera, $\lambda/4$ plates that cause a phase modulation of $-\lambda/4$ are arranged in the upper left (UL) and upper right (UR) regions, and $\lambda/4$ plates that cause a phase modulation of $+\lambda/4$ are arranged in the lower left (DL) and lower right (DR) regions.

Figure 39B:
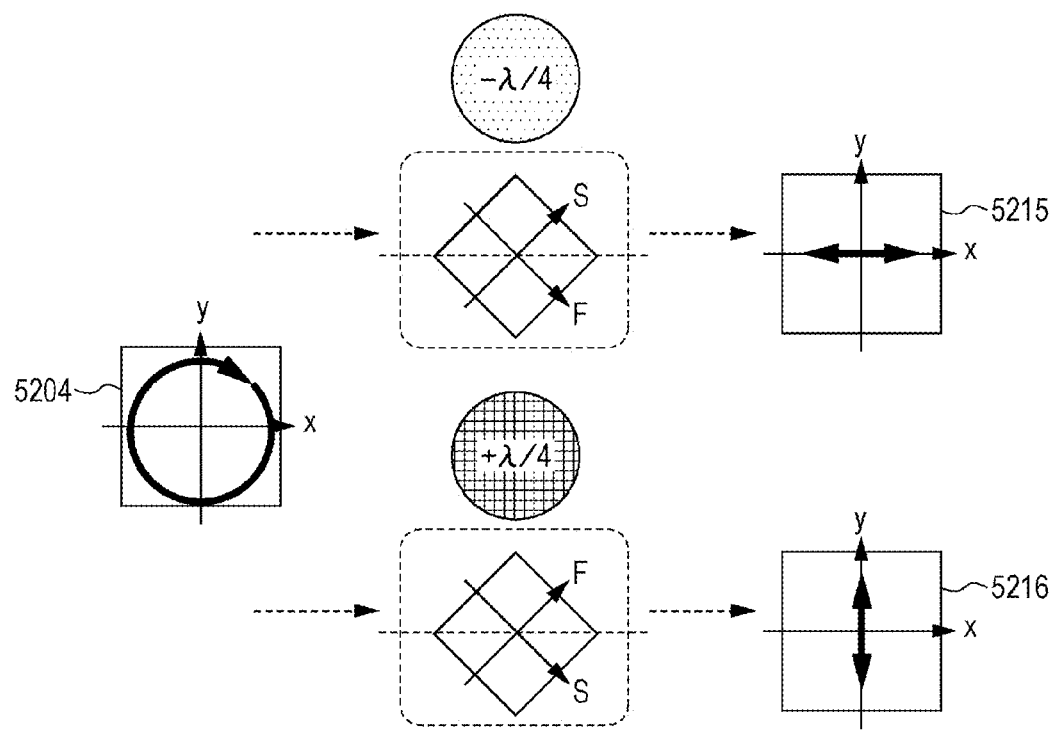

FIG. 39B illustrates the details of phase modulation of the above-described four optical elements. When the returning light, which is clockwise circularly polarized light, is incident on $\lambda/4$ plates that are arranged such that the F-axis (fast axis) and S-axis (slow axis) thereof are at an angle of 45° with respect to the X and Y axes in different manners, the $\lambda/4$ plates perform phase modulations of $-\lambda/4$ and $+\lambda/4$. When the returning light is subjected to the phase modulation of $-\lambda/4$, the returning light, which is the circularly polarized light, is converted into linearly polarized light 5215 that is polarized in the direction of 0°, similar to the light that has passed through the polarizing plate 5201 in the illumination-light generating process. When the returning light is subjected to the phase modulation of $+\lambda/4$, the phase of the circularly polarized light is further shifted so that the circularly polarized light is converted into linearly polarized light 5216 that is polarized in the direction of 90°. The two types of polarized light pass through two types of polarizing plates having the transmission axes in the directions of 0° and 90°.

Figure 40A:
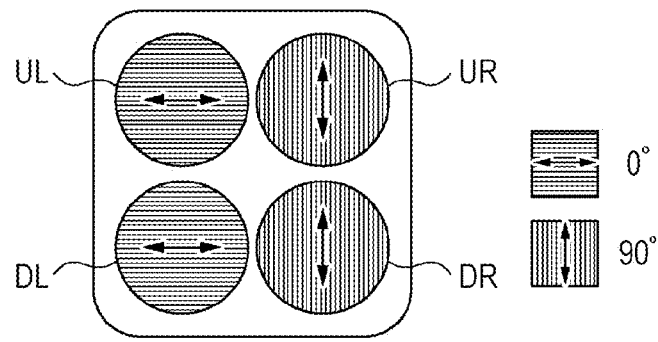
FIGS. 40A and 40B illustrate the polarization imaging apparatus according to the tenth embodiment of the present disclosure.

FIG. 40A illustrates the arrangement of the two types of polarizing plates that overlap the four openings. Linear polarizing plates having a transmission axis in the direction of 0° are arranged in the upper left (UL) and lower left (DL) regions, and linear polarizing plates having a transmission axis in the direction of 90° are arranged in the upper right (UR) and lower right (DR) regions.

Figure 40B:
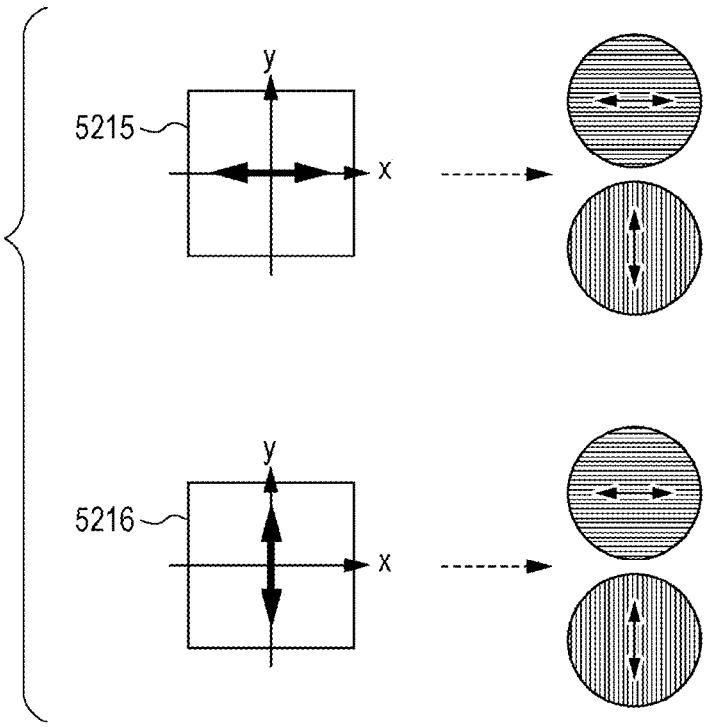

FIG. 40B illustrates the details of transmission of light through the above-described polarizing plates. A linearly polarized returning light component polarized in the direction of 0° is observed through polarizing plates having transmission axes in the directions of 0° and 90°, and a linearly polarized returning light component polarized in the direction of 90° is also observed through polarizing plates having transmission axes in the directions of 0° and 90°. Then, the returning light components are converted into brightness values by the imaging device. Although only the linearly polarized returning light components are illustrated in FIG. 40B, in practice, mixture of linearly polarized light components that have been attenuated and non-polarized (randomly polarized) light components is observed.

In the present embodiment, since the multiple-lens camera is used, the images formed by the four objective lenses are arranged next to each other on the imaging plane.

Figure 41:
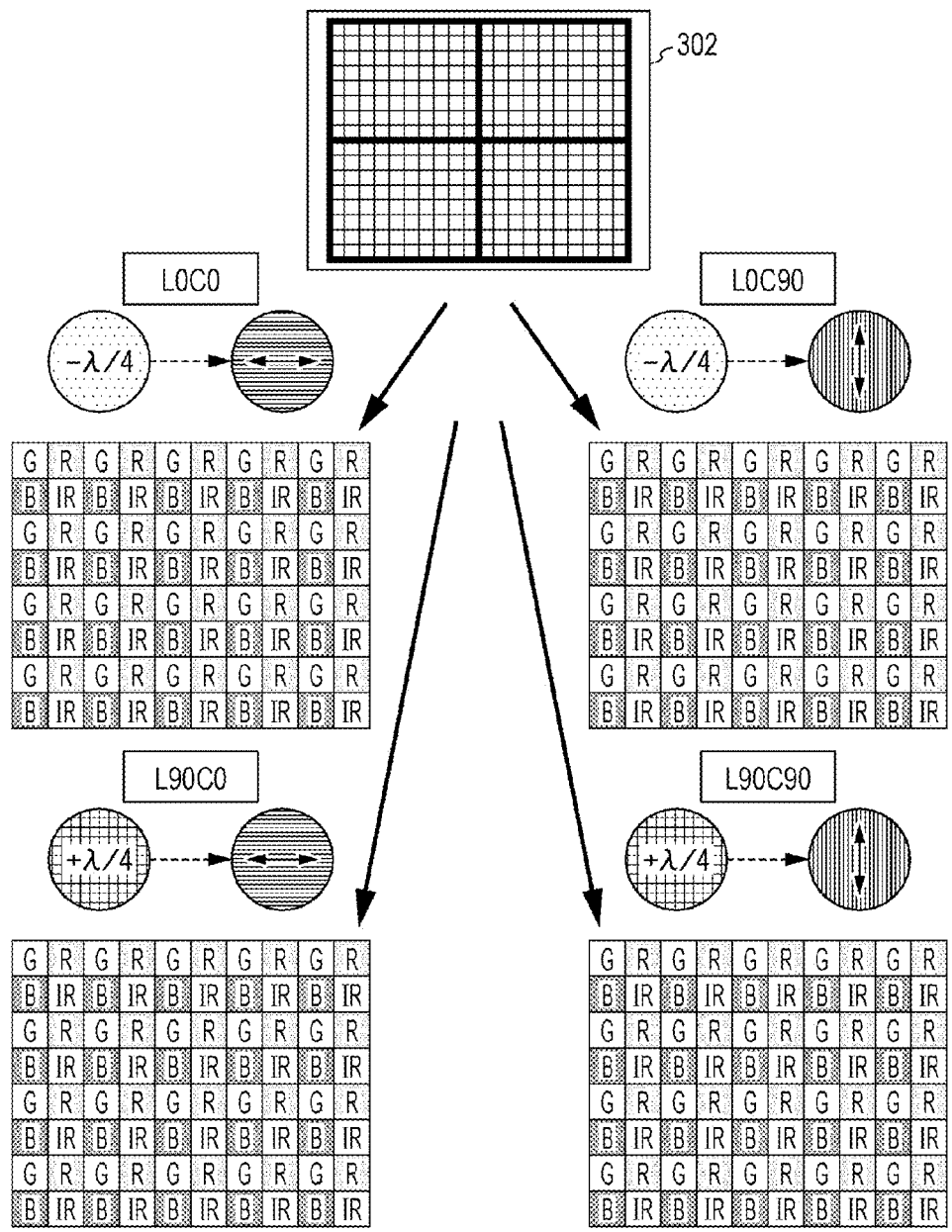
FIG. 41 illustrates a pixel selection process performed by the polarization imaging apparatus according to the tenth embodiment of the present disclosure.

FIG. 41 illustrates a pixel selection process performed to generate polarization images from the four images captured by the multiple-lens color camera while the images are arranged next to each other. The images that have passed through four regions on the openings of the four objective lenses are arranged next to each other in the upper left, upper right, lower left, and lower right regions on the single-plate color imaging device 302. When the captured images are separated from each other, although the resolution is reduced to $\frac{1}{4} \times \frac{1}{4}$, R, G, B, and IR color mosaic images can be separated from each other. By performing a known color mosaic interpolation process, four polarization images, which are full-color and infrared polarization images, can be obtained.

In the above-described temporally sequential method, the object is alternately illuminated with two types of linearly polarized light that are polarized in the directions of 0° and 90°, and four images in total are captured by performing polarization imaging at 0° and 90° on the returning light. Then, the average polarization difference image is generated from the captured four images. In contrast, according to the present embodiment, these processes are simultaneously performed in parallel. Therefore, when the present embodiment is applied to an on-board camera, the real-time performance of the camera can be improved. In addition, since it is not necessary to emit two types of light alternately, the structure of the polarized-light illumination unit can be simplified. In addition, compared to the case where separate light sources are used to emit two types of light alternately, the amount of light can be increased.

In the present embodiment, it is assumed that the illumination light is clockwise circularly polarized light. However, the illumination light may instead be counterclockwise circularly polarized light. In addition, the illumination light may be elliptically polarized light instead of circularly polarized light. In such a case, effects that are the same as those of the present embodiment can be obtained by shifting the phase by an appropriate amount instead of $\lambda/4$.

Eleventh Embodiment

Figure 42A:
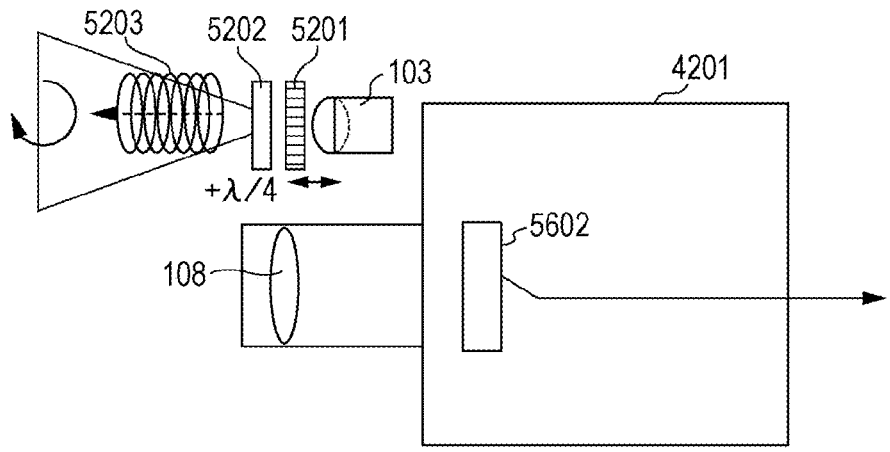
FIGS. 42A to 42C illustrate the structure of an imaging unit that serves as a polarization imaging apparatus according to an eleventh embodiment of the present disclosure.
Figure 42B:
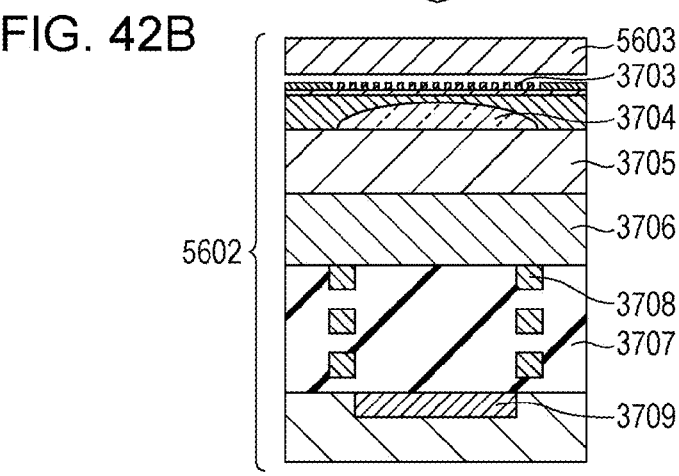
Figure 42C:
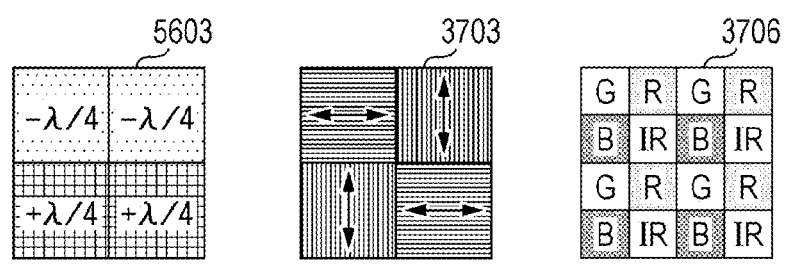

FIGS. 42A to 42C illustrate a polarization imaging apparatus according to an eleventh embodiment of the present disclosure. Similar to the tenth embodiment, the polarization imaging apparatus includes a camera 4201 capable of performing image processing similar to that in the case where two types of linearly polarized light are alternately emitted, by using circularly polarized light having an oscillation plane that rotates in a certain direction as illumination light. The camera 4201 includes an illumination unit having a simple structure, and is capable of performing image processing in real time within a single frame by simultaneously capturing four polarization images in different states. The eleventh embodiment differs from the tenth embodiment in that the camera 4201 includes a color polarization image sensor 5602 in which a phase modulation filter including $\lambda/4$ plates and a mosaic polarizing filter including two types of regions having transmission axes in the directions of 0° and 90° are arranged on a color imaging device having four wavelength ranges R, G, B, and IR. The structure of the illumination unit is the same as that in the tenth embodiment, and description thereof is thus omitted.

FIG. 42B illustrates the cross sectional structure of the color polarization image sensor 5602. The incident light reaches an imaging plane through an objective lens 108. Components will be described in the order in which the light reaches. First, an optical filter 5603, which functions as $\lambda/4$ plates, is provided at the top. Next, a wire grid mosaic 3703 made of a metal and a microlens 3704 are arranged in that order.

The optical filter 5603 includes optical elements called phase shifters, which are made of a birefringent medium such as crystal or liquid crystal.

The microlens 3704 has a function of efficiently collecting light at a photodiode (PD) 3709. A planarizing layer 3705 and a color filter mosaic 3706 are disposed under the microlens 3704. The color filter mosaic 3706 may be made of an organic material, a photonic crystal, or a metal. A planarizing layer 3707 and a wiring layer 3708 are provided under the color filter mosaic 3706. Wires are not provided in regions where light is transmitted, so that the light reaches the photodiode (PD) 3709 under the planarizing layer 3707 and the wiring layer 3708 without being blocked.

FIG. 42C illustrates the planar arrangement of the color polarization image sensor 5602. The planar structures of the phase modulation filter 5603, which includes λ/4 plates, the color filter mosaic 3706, and the wire grid mosaic 3703 are illustrated. Owing to the manner in which the phase modulation filter 5603 and the wire grid mosaic 3703 overlap, four types of polarization images L0C0, L0C90, L90C0, and C90C90 similar to those illustrated in FIG. 15 are simultaneously captured in a region of 2×2 pixels. Each of these four pixels includes four color pixels corresponding to the wavelength ranges of R, G, B, and IR. Thus, four types of polarization images can be captured for each of the four wavelength ranges in parallel.

Twelfth Embodiment

Figure 43A:
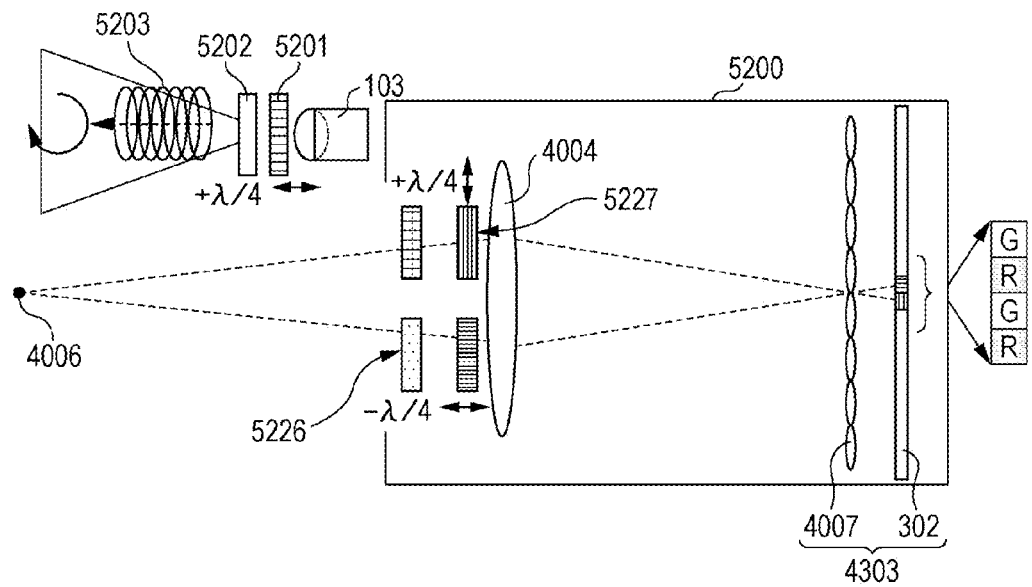
FIGS. 43A to 43C illustrate the structure of an imaging unit that serves as a polarization imaging apparatus according to a twelfth embodiment of the present disclosure.

FIG. 43A illustrates a polarization imaging apparatus according to a twelfth embodiment of the present disclosure. Similar to the tenth embodiment, the polarization imaging apparatus includes a camera 5200 capable of performing image processing similar to that in the case where two types of linearly polarized light are alternately emitted, by using circularly polarized light having an oscillation plane that rotates in a certain direction as illumination light. The camera 5200 includes an illumination unit having a simple structure, and is capable of performing image processing in real time within a single frame by simultaneously capturing four polarization images in different states. The twelfth embodiment differs from the tenth embodiment in that a phase modulation filter 5226 including λ/4 plates and a mosaic polarizing filter 5227 including two types of regions having transmission axes in the directions of 0° and 90° are arranged on openings of an objective lens 4004, and color separation and polarization imaging are performed by using a microlens-array color image sensor 4303 in which a microlens array 4007 and a color imaging device 302 having four types of pixels corresponding to the wavelength ranges of R, G, B, and IR are provided on an imaging plane. The structure of the circularly-polarized-light illumination unit is the same as that in the above-described embodiments, and description thereof is thus omitted. Divergent light that returns from a single point 4006 on the object passes through four regions of the objective lens 4004. In FIG. 43A, only two regions are illustrated. The light that has passed through the objective lens 4004 passes through the microlens array 4007 and reaches the color imaging device 302 on which a color mosaic is arranged. Images that have passed through different regions of the objective lens 4004 reach different pixels. Therefore, although an image formed on the color imaging device 302 is an image of the object as a whole, the image includes images of four different regions to be precise. Each region corresponds to 2×2 pixels in the color mosaic included in the color imaging device 302.

Figure 43B:
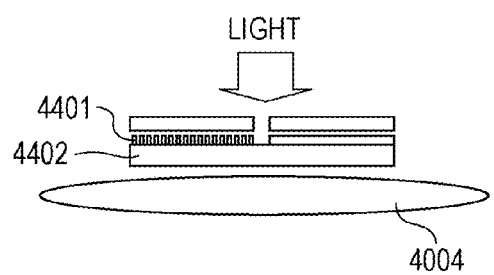

FIG. 43B illustrates the cross-sectional structure of a region around the objective lens according to the present embodiment. In this example, a metal wire grid layer 4401 is used as the polarizing filter. The wire grid layer 4401 includes metal wires arranged on a transparent substrate 4402 at a pitch of about 100 nm, and a polarizing operation can be performed over a wide range including a visible light range and an infrared light range. The objective lens 4004 is disposed behind the transparent substrate 4402. The order in which the wire grid layer and the objective lens are arranged is not limited, and the wire grid layer and the objective lens may either be arranged with or without a gap provided therebetween. The polarizing plate may be a polymer-based polarizing plate instead of a wire grid polarizing plate as long as the polarizing operation can be performed over a wide range in the visible light range. The wire grid layer may be made of various types of materials, such as aluminum (Al). The wire grid may have a multilayer structure in which the outermost layer is a light absorbing layer that suppresses reflection of light. Gaps between the wire grids may be filled with another material to increase the mechanical strength. Also, the wire grids may be coated to protect the surfaces thereof from chemical reactions.

Figure 43C:
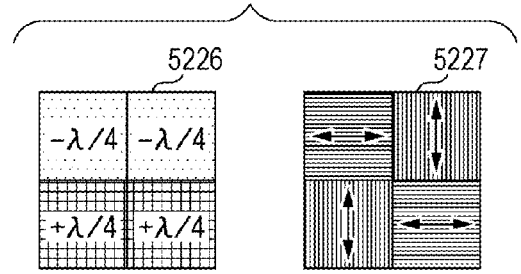

FIG. 43C illustrates the planar structure of the polarizing filter regions 4302. The polarizing filter regions 4302 include four polarizing filter regions having polarization transmission axes in the directions of 0° and 90° and arranged in two rows and two columns.

Figure 44:
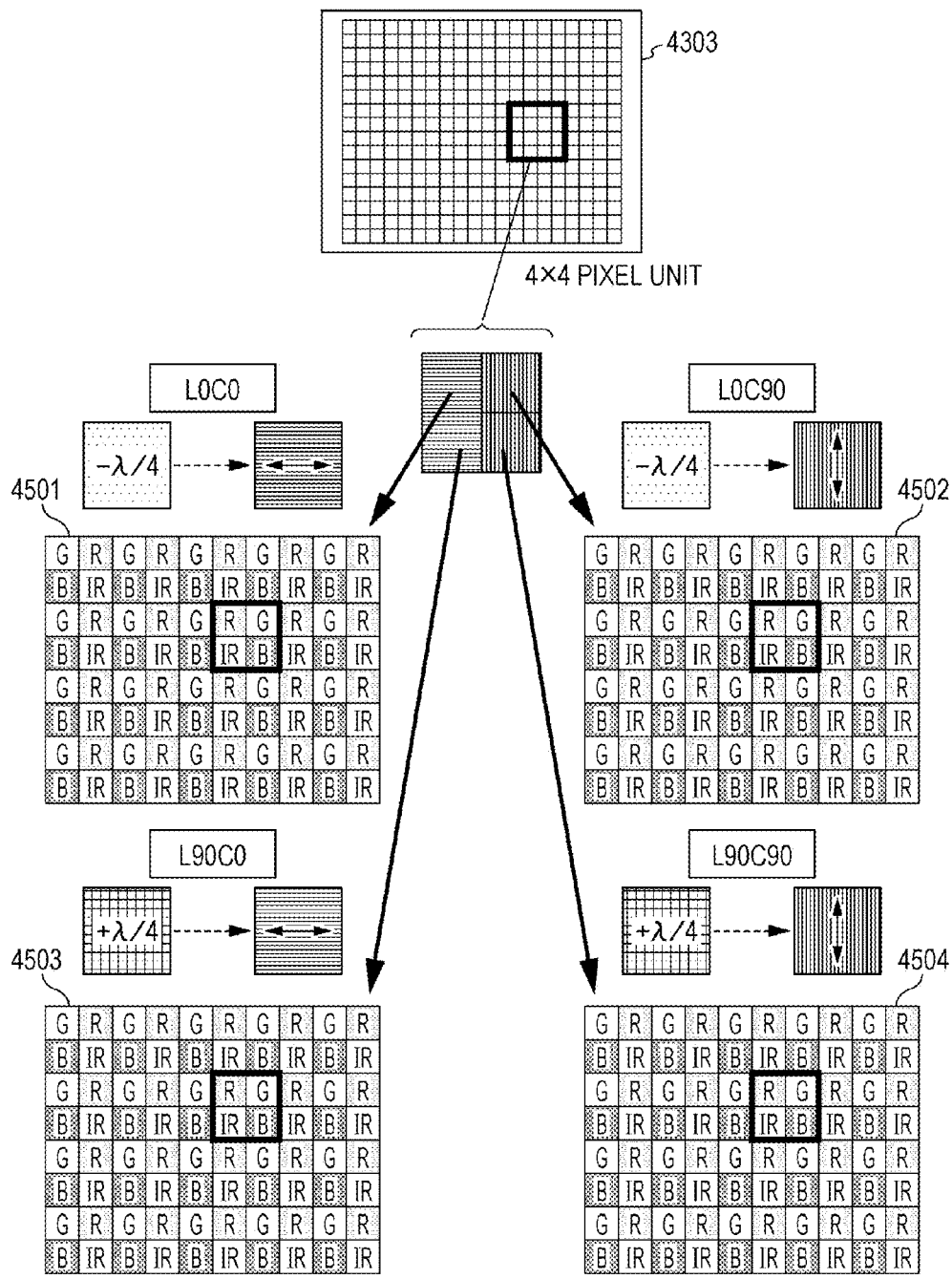
FIG. 44 illustrates a pixel selection-and-reintegration process performed by the polarization imaging apparatus according to the twelfth embodiment of the present disclosure.

FIG. 44 illustrates a pixel selection-and-reintegration process performed to generate polarization images from the image captured by the microlens-array color image sensor 4303. A pixel unit including pixels arranged in four rows and four columns in the image formed on the sensor 4303 corresponds to light rays from the four filter regions on the opening of the objective lens. Pixels arranged in two rows and two columns in the upper left, upper right, lower left, and lower right regions are selected and reintegrated over the entire image. Thus, although the resolution is reduced to ¼×¼, R, G, B, and IR color mosaic images 4501 and 4504 that correspond to the polarization transmission axis in the direction of 0° and R, G, B, and IR color mosaic images 4502 and 4503 that correspond to the polarization transmission axis in the direction of 90° can be separated from each other. By performing a known color mosaic interpolation process, full-color and infrared polarization images corresponding to the polarization transmission axes in the directions of 0° and 90° can be obtained.

According to the present embodiment, since the polarizing plate can be arranged at the opening of the lens, the size of each polarization mosaic element can be increased compared to that in the case where the polarizing plate is disposed on the imaging device. For example, in a polarization-mosaic-type imaging device used in the ninth embodiment, the length of a portion of each metal wire that forms a polarization mosaic unit is the same as the pixel size of the imaging device, and is typically 1 to 3 μm. With such a small size, even when the pitch of the metal wires included in the wire grid is small, the wire grid length and the number of wires are limited. As a result, the optical extinction ratio of the polarizing plate is reduced to about 10:1 or less. In the present embodiment, a relatively large wire grid polarizing plate whose size is about 0.5 mm (=500 μm), which is the size of the opening of the lens, can be used, and a high optical extinction ratio of about 100:1 can be realized. This is extremely advantageous from the viewpoint of performance.

Thirteenth Embodiment

Figure 45A:
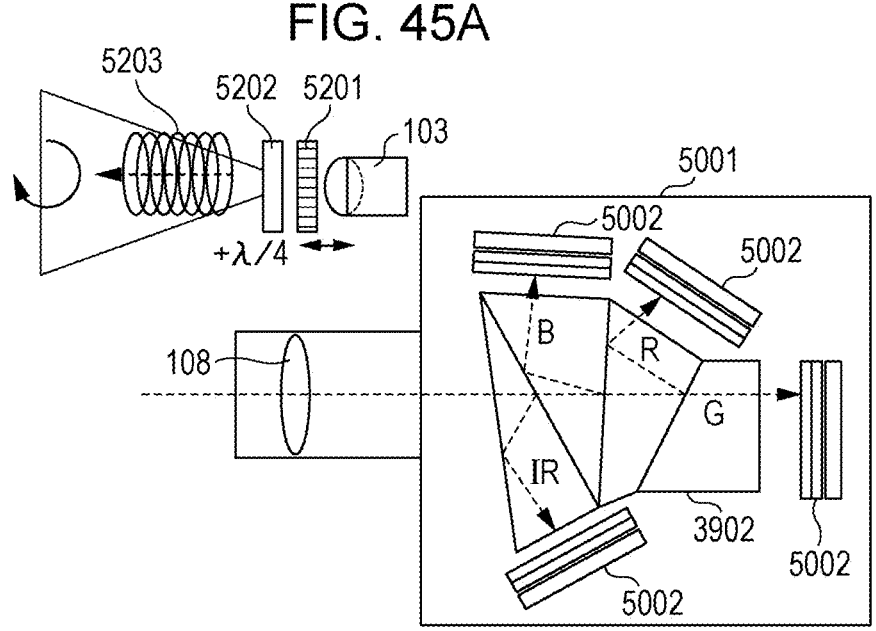
FIGS. 45A to 45C illustrate the structure of an imaging unit that serves as a polarization imaging apparatus according to a thirteenth embodiment of the present disclosure.
Figure 45B:
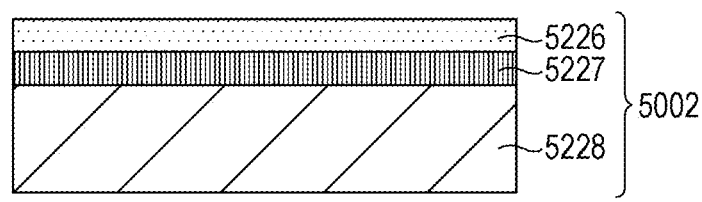
Figure 45C:
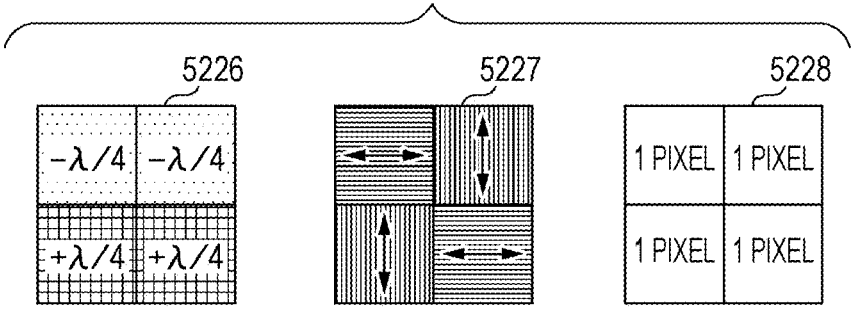

FIG. 45A illustrates a polarization imaging apparatus according to a thirteenth embodiment of the present disclosure. Similar to the tenth embodiment, the polarization imaging apparatus includes a camera 5001 capable of performing image processing similar to that in the case where two types of linearly polarized light are alternately emitted, by using circularly polarized light having an oscillation plane that rotates in a certain direction as illumination light. The camera 5001 includes an illumination unit having a simple structure, and is capable of performing image processing in real time within a single frame by simultaneously capturing four polarization images in different states. The thirteenth embodiment differs from the tenth embodiment in that the camera 5001 includes a four-color separation prism 3902 which divides light incident thereon into four types of light components having the wavelength ranges of R, G, B, and IR, and color separation and polarization imaging for the light components of the respective colors are performed by using monochrome polarization image sensors 5002. Referring to FIG. 45B, in each monochrome polarization image sensor 5002, a phase modulation filter mosaic 5226 including $\lambda/4$ plates, a mosaic polarizing filter 5227 including two types of regions having transmission axes in the directions of 0° and 90°, and a monochrome imaging device 5228 are stacked together. As illustrated in FIG. 45C, since four types of polarizing filter regions overlap 2×2 pixel regions of the monochrome imaging device 5228, four types of polarization images can be simultaneously obtained by reintegration of the pixels. The structure of the circularly-polarized-light illumination unit is the same as that in the above-described embodiments, and description thereof is thus omitted. The four types of polarization images obtained by the four types of image sensors are the same as those in the twelfth embodiment, and description thereof is thus omitted.

In the present embodiment, the four-color separation prism is used since light is divided into four types of light components having the wavelength ranges of R, G, B, and IR. However, in the case where the light is divided into three types of light components having the wavelength ranges of R, G, and B, a three-color separation prism, such as an ordinary dichroic prism, may be used and the structure can be simplified. This structure is, of course, included in the present embodiment.

Modification of Thirteenth Embodiment

Figure 46A:
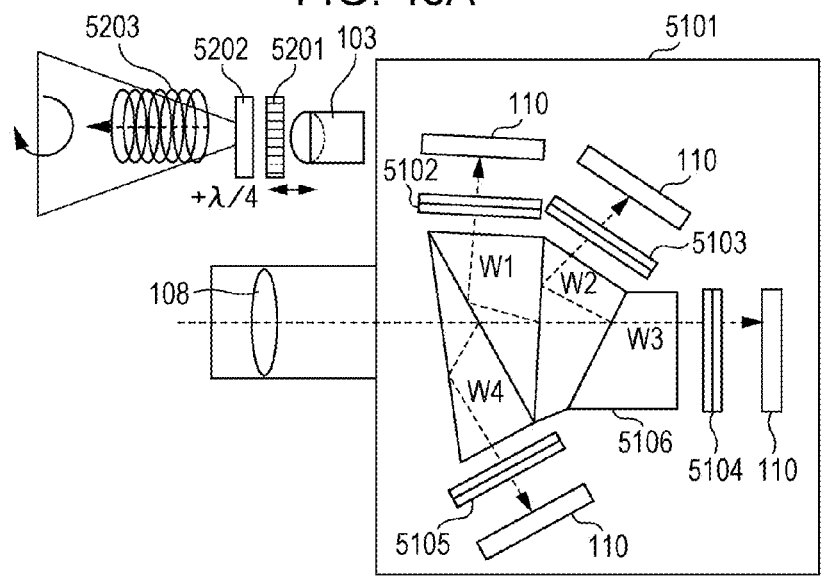
FIGS. 46A to 46C illustrate a polarization imaging apparatus according to a modification of the thirteenth embodiment of the present disclosure.
Figure 46B:
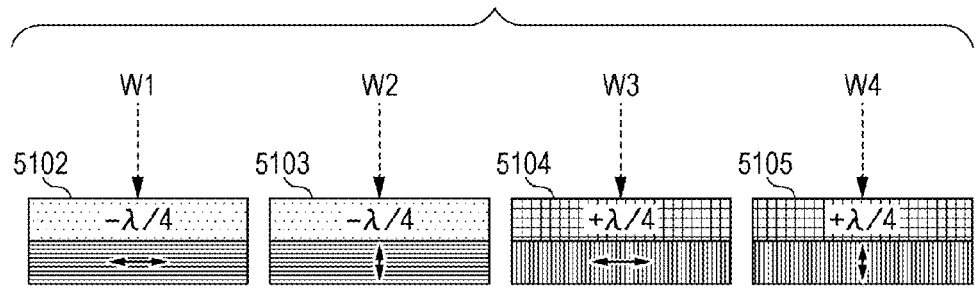
Figure 46C:
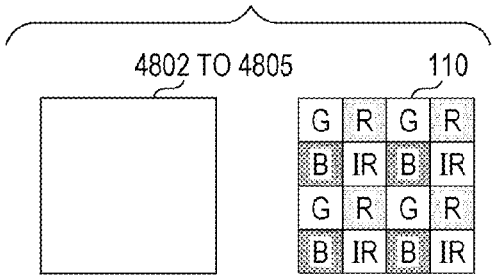

FIG. 46A illustrates a polarization imaging apparatus according to an eleventh embodiment of the present disclosure. Similar to the tenth embodiment, the polarization imaging apparatus includes a camera 5101 capable of performing image processing similar to that in the case where two types of linearly polarized light are alternately emitted, by using circularly polarized light having an oscillation plane that rotates in a certain direction as illumination light. The camera 5101 includes an illumination unit having a simple structure, and is capable of performing image processing in real time within a single frame by simultaneously capturing four polarization images in different states. This modification differs from the tenth embodiment in that the roles of the prism and the polarizing filter are switched, and a prism 5106 divides light incident thereon into four types of light components W1, W2, W3, and W4 having the same wavelength distribution. Referring to FIG. 46B, the light components W1, W2, W3, and W4 are caused to pass through filters 5102 to 5105 in which phase modulation filters including $\lambda/4$ plates and two types of mosaic polarizing filters having transmission axes in the directions of 0° and 90° are stacked. Color separation and polarization imaging are performed by using single-panel color image sensors 110 including mosaic filters having four types of wavelength ranges R, G, B, and IR. As illustrated in FIG. 46C, since the different types of polarization filter regions overlap the corresponding single-panel color image sensors over the entire region thereof, four types of polarization filter images can be simultaneously obtained.

The four types of images output from the four types of color image sensors and the subsequent processes are the same as those in other embodiments, and description thereof is thus omitted.

According to the apparatuses of the present disclosure, irregularities on the surface of a transparent or translucent object can be detected. Therefore, the apparatuses may be widely applied to detection of droplets or raindrops with on-board cameras or surveillance cameras used to observe scenes through transparent glass.

What is claimed is:

1. A polarization image processing apparatus comprising:
    an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus;
    a splitter that splits returning light that returns from the object into at least two returning light components;
    a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light;
    a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and
    a processing unit that receives the first, second, third, and fourth polarization images from the first and second polarization imaging devices and detects a condition of a second surface of the object on the basis of a difference between a sum of the first polarization image and the fourth polarization image and a sum of the second polarization image and the third polarization image, the second surface being at a side opposite to a side of the first surface.

2. The polarization image processing apparatus according to claim 1, wherein the processing unit performs
    a first process of taking an average of the first polarization image and the fourth polarization image to generate an average parallel-Nicols image,
    a second process of taking an average of the second polarization image and the third polarization image to generate an average crossed-Nicols image, and
    a third process of determining the difference by performing a subtraction between the average parallel-Nicols image and the average crossed-Nicols image.

3. The polarization image processing apparatus according to claim 2, wherein the processing unit generates a brightness image by adding the first, second, third, and fourth polarization images.

4. The polarization image processing apparatus according to claim 3, wherein the illumination unit includes a plurality of the first light sources that emit the first illumination light and a plurality of the second light sources that emit the second illumination light.

5. The polarization image processing apparatus according to claim 4, comprising an imaging unit including the illumination unit, the splitter, and the first and second polarization imaging devices,
wherein the processing unit is connected to the imaging unit.

6. The polarization image processing apparatus according to claim 5, wherein the processing unit includes a droplet detecting unit that detects a droplet on the second surface of the object.

7. A polarization image processing apparatus comprising:
an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus;
a splitter that splits returning light that returns from the object into first, second, and third light components;
a first polarization imaging device that receives the first light component, the first polarization imaging device obtaining a first polarization image polarized in the first direction while the object is being illuminated with the first illumination light and obtaining a second polarization image polarized in the first direction while the object is being illuminated with the second illumination light;
a second polarization imaging device that receives the second light component, the second polarization imaging device obtaining a third polarization image polarized in the second direction while the object is being illuminated with the first illumination light and obtaining a fourth polarization image polarized in the second direction while the object is being illuminated with the second illumination light;
a third polarization imaging device that receives the third light component, the third polarization imaging device obtaining a fifth polarization image polarized in a third direction, which differs from the first and second directions, while the object is being illuminated with the first illumination light and obtaining a sixth polarization image polarized in the third direction while the object is being illuminated with the second illumination light; and
a processing unit that receives the second, third, fifth, and sixth polarization images from the first, second, and third polarization imaging devices and detects a condition of a second surface the object on the basis of a difference between a sum of the fifth polarization image and the sixth polarization image and a sum of the second polarization image and the third polarization image, the second surface being at a side opposite to a side of the first surface.

8. The polarization image processing apparatus according to claim 7,
wherein the first direction and the second direction are orthogonal to each other, and
wherein the third direction is at an angle in the range of 10 degrees or more and 60 degrees or less with respect to the first direction.

9. The polarization image processing apparatus according to claim 8, wherein the processing unit performs
a first process of taking an average of the fifth polarization image and the sixth polarization image to generate an average oblique-Nicols image,
a second process of taking an average of the second polarization image and the third polarization image to generate an average crossed-Nicols image, and
a third process of determining the difference by performing a subtraction between the average oblique-Nicols image and the average crossed-Nicols image.

10. The polarization image processing apparatus according to claim 9, wherein the processing unit generates a brightness image by adding the first, second, third, and fourth polarization images.

11. The polarization image processing apparatus according to claim 10, wherein the illumination unit includes a plurality of the first light sources that emit the first illumination light and a plurality of the second light sources that emit the second illumination light.

12. The polarization image processing apparatus according to claim 11, comprising an imaging unit including the illumination unit, the splitter, and the first and second polarization imaging devices,
wherein the processing unit is connected to the imaging unit.

13. The polarization image processing apparatus according to claim 12, wherein the processing unit includes a droplet detecting unit that detects a droplet on the second surface of the object.

14. A polarization image processing apparatus comprising:
an illumination unit that illuminates a first surface of a transparent or translucent object with first illumination light and second illumination light alternately, the first illumination light being in a first state of polarization and the second illumination light being in a second state of polarization that differs from the first state of polarization, an illumination axis of the first illumination light and an illumination axis of the second illumination light substantially coinciding with an imaging axis of the polarization image processing apparatus;
a splitter that splits returning light that returns from the object into at least two returning light components;
a phase shift element arranged so as to allow the returning light that returns from the object to pass therethrough, the phase shift element converting clockwise polarized light into light polarized in a first direction and counterclockwise polarized light into light polarized in a second direction that is orthogonal to the first direction;
a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light;
a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of a second surface of the object on the basis of a difference between a sum of the first polarization image and the fourth polarization image and a sum of the second polarization image and the third polarization image, the second surface being at a side opposite to a side of the first surface.

15. The polarization image processing apparatus according to claim 14, wherein one of the first state of polarization and the second state of polarization is clockwise circular or elliptical polarization, and the other one of the first state of polarization and the second state of polarization is counterclockwise circular or elliptical polarization.

16. The polarization image processing apparatus according to claim 15, wherein the phase shift element is a quarter wave plate.

17. A polarization image processing apparatus comprising:
an illumination unit that illuminates a first surface of a transparent or translucent object with circularly polarized light or elliptically polarized light, an illumination axis of the circularly polarized light or elliptically polarized light substantially coinciding with an imaging axis of the polarization image processing apparatus;
a splitter that splits returning light that returns from the object into at least two returning light components;
a variable phase shift element arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction;
a first polarization imaging device that receives one of the at least two returning light components, the first polarization imaging device obtaining a first polarization image polarized in the first direction while the variable phase shift element is operating in the first mode and obtaining a second polarization image polarized in the first direction while the variable phase shift element is operating in the second mode;
a second polarization imaging device that receives another one of the at least two returning light components, the second polarization imaging device obtaining a third polarization image polarized in the second direction while the variable phase shift element is operating in the first mode and obtaining a fourth polarization image polarized in the second direction while the variable phase shift element is operating in the second mode; and
a processing unit that receives the first, second, third, and fourth polarization images from the first and second polarization imaging devices and detects a condition a second surface of the object on the basis of a difference between a sum of the first polarization image and the fourth polarization image and a sum of the second polarization image and the third polarization image, the second surface being at a side opposite to a side of the first surface.

18. A polarization image processing apparatus comprising:
an illumination unit that illuminates a first surface of a transparent or translucent object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the polarization image processing apparatus;
a polarization imaging device that receives returning light that returns from the object, the polarization imaging device obtaining a first polarization image polarized in the first direction and a second polarization image polarized in a second direction while the object is being illuminated with the first illumination light and obtaining a third polarization image polarized in the first direction and a fourth polarization image polarized in the second direction while the object is being illuminated with the second illumination light; and
a processing unit that receives the first, second, third, and fourth polarization images from the polarization imaging device and detects a condition of a second surface of the object on the basis of a difference between a sum of the first polarization image and the fourth polarization image and a sum of the second polarization image and the third polarization image, the second surface being at a side opposite to a side of the first surface.

19. The polarization image processing apparatus according to claim 18, wherein the processing unit includes a droplet detecting unit that detects a droplet on the second surface of the object.

20. The polarization image processing apparatus according to claim 19,
wherein the polarization imaging device includes
an image sensor, and
a polarizing plate disposed between an imaging plane of the image sensor and the object, the polarizing plate including at least one first polarizer that transmits light polarized in the first direction and at least one second polarizer that transmits light polarized in the second direction.

21. A polarization image processing apparatus comprising:
an illumination unit disposed such that an illumination axis substantially coincides with an imaging axis, the illumination unit illuminating an object with circularly polarized illumination light obtained by combining first linearly polarized light and second linearly polarized light with a phase difference provided therebetween, the first linearly polarized light and the second linearly polarized light being respectively polarized in a first direction and a second direction orthogonal to the first direction;
a polarization imaging device that receives returning light including circularly polarized light reflected by the object, the polarization imaging device including a light dividing unit that divides the returning light into four light components, the polarization imaging device simultaneously obtaining a first polarization image, a second polarization image, a third polarization image, and a fourth polarization image, the first polarization image being obtained by causing the returning light to successively pass through a phase shifter that causes a phase shift for changing a state of the returning light to a state of linear polarization in the first direction and a polarizer whose direction of polarization is the first direction, the second polarization image being obtained by causing the returning light to successively pass through a phase shifter that causes a phase shift for changing a state of the returning light to a state of linear polarization in the first direction and a polarizer whose direction of polarization is the second direction, the third polarization image being obtained by causing the returning light to successively pass through a phase shifter that causes a phase shift for changing a state of the returning light to a state of linear polarization in the second direction and a polarizer whose direction of polarization is the first direction, and the fourth polarization image being obtained by causing the returning light to successively pass through a phase shifter that causes a phase shift for changing a state of the returning light to a state of linear polarization in the second direction and a polarizer whose direction of polarization is the second direction; and a processing unit that performs image processing on the basis of a difference between a sum of the first polarization image and the fourth polarization image and a sum of the second polarization image and the third polarization image.

* * * * *